(12) United States Patent
Sellars

(10) Patent No.: US 10,192,639 B2
(45) Date of Patent: Jan. 29, 2019

(54) METHOD AND SYSTEM FOR MEDICAL SUGGESTION SEARCH

(71) Applicant: DrFirst.com, Inc., Rockville, MD (US)

(72) Inventor: David Andrew Sellars, Zanesfield, OH (US)

(73) Assignee: DrFirst.com, Inc., Rockville, MD (US)

( * ) Notice: Subject to any disclaimer, the term of this patent is extended or adjusted under 35 U.S.C. 154(b) by 869 days.

(21) Appl. No.: 14/613,174

(22) Filed: Feb. 3, 2015

(65) Prior Publication Data

US 2016/0055302 A1   Feb. 25, 2016

Related U.S. Application Data

(63) Continuation-in-part of application No. 14/466,663, filed on Aug. 22, 2014, now abandoned.

(51) Int. Cl.
*G06F 19/00*   (2018.01)
*G06F 17/30*   (2006.01)
*G16H 50/20*   (2018.01)

(52) U.S. Cl.
CPC ............. *G16H 50/20* (2018.01); *G06F 19/00* (2013.01)

(58) Field of Classification Search
CPC .......... G06F 17/3053; G06F 17/30985; G06F 19/326; G06Q 50/24; G16H 10/60; G16H 50/20; G16H 50/30; G16H 50/50
See application file for complete search history.

(56) References Cited

U.S. PATENT DOCUMENTS

| | | |
|---|---|---|
| 6,697,783 B1 | 2/2004 | Brinkman et al. |
| 7,664,660 B2 | 2/2010 | Korpman et al. |
| 7,860,925 B1 | 12/2010 | Gheorghe et al. |
| 8,239,213 B1 | 8/2012 | Paul et al. |
| 8,473,310 B2 | 6/2013 | Hasan et al. |
| 2003/0046114 A1 | 3/2003 | Davies et al. |
| 2006/0025657 A1 | 2/2006 | Rosenfeld et al. |
| 2006/0218012 A1 | 9/2006 | Hernandez et al. |
| 2006/0275844 A1 | 12/2006 | Linke et al. |
| 2006/0278241 A1 | 12/2006 | Ruano |
| 2008/0133275 A1 | 6/2008 | Huag |
| 2008/0162352 A1 | 7/2008 | Gizewski |

(Continued)

FOREIGN PATENT DOCUMENTS

WO   02/095650 A2   11/2002

OTHER PUBLICATIONS

International Search Report and Written Opinion dated Apr. 8, 2016 in PCT/US2016/016128.
Office Action dated Dec. 30, 2016 in U.S. Appl. No. 14/466,663.

*Primary Examiner* — Maroun P Kanaan
(74) *Attorney, Agent, or Firm* — Brake Hughes Bellermann LLP

(57) ABSTRACT

The present teaching relates to medical suggestion searching. In one example, data related to a medication drug are obtained. One or more candidate prescription strings are identified from the obtained data. Each of the candidate prescription strings is associated with a plurality of attributes. Each of the one or more candidate prescription strings is automatically processed based on at least one model to generate one or more prescription strings each with an associated ranking. At least some of the generated one or more prescription strings and the associated rankings are stored for future use.

20 Claims, 53 Drawing Sheets

(56) References Cited

U.S. PATENT DOCUMENTS

| | | |
|---|---|---|
| 2011/0105852 A1* | 5/2011 | Morris .................. G06Q 10/10 600/300 |
| 2011/0246240 A1 | 10/2011 | Hasan et al. |
| 2012/0041789 A1 | 2/2012 | Sweeney |
| 2012/0179481 A1 | 7/2012 | Patel |
| 2014/0046889 A1 | 2/2014 | Biem et al. |
| 2014/0136226 A1 | 5/2014 | Dittmer et al. |
| 2015/0066539 A1 | 3/2015 | Sheffer et al. |
| 2015/0073828 A1* | 3/2015 | Mortara .............. G06F 19/3487 705/3 |
| 2015/0081321 A1 | 3/2015 | Jain |
| 2015/0294069 A1 | 10/2015 | Shah |
| 2016/0019346 A1 | 1/2016 | Boston et al. |

\* cited by examiner

| Dimension – Specialty | Cardiology | Neurosurgery | Psychiatry |
|---|---|---|---|
| Medical Suggestion 1 | Score | Score | Score |
| Medical Suggestion 2 | Score | Score | Score |
| Medical Suggestion 3 | Score | Score | Score |
| Medical Suggestion 4 | Score | Score | Score |
| Medical Suggestion 5 | Score | Score | Score |
| Medical Suggestion 6 | Score | Score | Score |
| Medical Suggestion 7 | Score | Score | Score |

FIG. 20

| 4402 | 4404 | 4406 | 4408 | 4410 | 4412 | 4414 | 4416 | 4418 | 4420 | 4422 |
|---|---|---|---|---|---|---|---|---|---|---|
| Drug ID | Action | Dose | Unit | Route | Timing | Duration | Dispense | Dispense Quantity | Related Disease | Others |

METHOD AND SYSTEM FOR MEDICAL SUGGESTION SEARCH

CROSS-REFERENCE TO RELATED APPLICATIONS

The present application is a continuation-in-part of U.S. patent application Ser. No. 14/466,663, filed Aug. 22, 2014, entitled "Method and System for Recommending Prescription Strings," which is incorporated herein by reference in its entirety.

BACKGROUND

Technical Field

The present teaching relates to methods, systems and programming for health care. More specifically, the present teaching relates to methods, systems, and programming for medical suggestion search.

Discussion of Technical Background

Users of traditional e-prescription systems have to sort through a large number of possible drugs when they are doing e-prescribing or medication reconciliation. This introduces many additional keystrokes and clicks into the user workflow on a per-patient, per medication level. For example, on a typical patient, users of the traditional e-prescription systems have to make over 20 clicks in order to sort through possible drugs in the systems for e-prescribing or medication reconciliation when the patient leaves from the hospital or clinic. Users ordering laboratory tests and radiology procedures face the similar issues with inhibited workflow and potential for error.

Some e-prescription systems allow users to create favorite drug lists instead of going through all the available drugs in the systems. However, each user of those e-prescription systems has to spend a considerable amount of time on manually creating their own favorite lists and modifying the favorite lists every time new drugs are added into the systems. The initial setup of the favorite lists for a heath care organization, e.g., a hospital, may take up to several months. In addition, mistakes occur during the manual creation of the favorite lists by users and may be multiplied for the lifetime of the users in the traditional e-prescription systems with no practical way to identify and correct them. Many Lab/Radiology systems have limited user favorite abilities as well.

SUMMARY

The present teaching relates to methods, systems and programming for health care. More specifically, the present teaching relates to methods, systems, and programming for medical suggestion search.

In one example, a method, implemented on at least one computing device each of which has at least one processor, storage, and a communication platform connected to a network for generating prescription strings is presented. Data related to a medication drug are obtained. One or more candidate prescription strings are identified from the obtained data. Each of the candidate prescription strings is associated with a plurality of attributes. Each of the one or more candidate prescription strings is automatically processed based on at least one model to generate one or more prescription strings each with an associated ranking. At least some of the generated one or more prescription strings and the associated rankings are stored for future use.

In another example, a method, implemented on at least one computing device each of which has at least one processor, storage, and a communication platform connected to a network for recommending prescription strings is presented. A request is received for recommending a prescription string. The request is resulted from a single action of a user and associated with a least one parameter. At least one prescription string stored previously is identified. Each of the at least one prescription string has a plurality of attributes that match with the at least one parameter. The at least one prescription string is provided as recommendation for the request.

In yet another example, a system having at least one processor, storage, and a communication platform for generating prescription strings is presented. The system includes a data analyzer, an analytic engine, and a re-contextualizing unit. The data analyzer is configured to obtain data related to a medication drug and identify one or more candidate prescription strings from the obtained data. Each of the candidate prescription strings is associated with a plurality of attributes. The analytic engine is configured to automatically process each of the one or more candidate prescription strings based on at least one model to generate one or more prescription strings each with an associated ranking. The re-contextualizing unit is configured to store at least some of the generated one or more prescription strings and the associated rankings for future use.

In a different example, a system having at least one processor, storage, and a communication platform for recommending prescription strings is presented. The at least one processor is configured to receive a request for recommending a prescription string. The request is resulted from a single action of a user and associated with a least one parameter. The at least one processor is configured to identify at least one prescription string stored previously. Each of which has a plurality of attributes that match with the at least one parameter. The at least one processor is configured to provide the at least one prescription string as recommendation for the request.

Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF THE DRAWINGS

The methods, systems and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 20 illustrates an exemplary medical suggestion data map in a patient care dimension, according to an embodiment of the present teaching;

FIG. 44 illustrates an exemplary prescription string, according to an embodiment of the present teaching;

DETAILED DESCRIPTION

Figure 1:
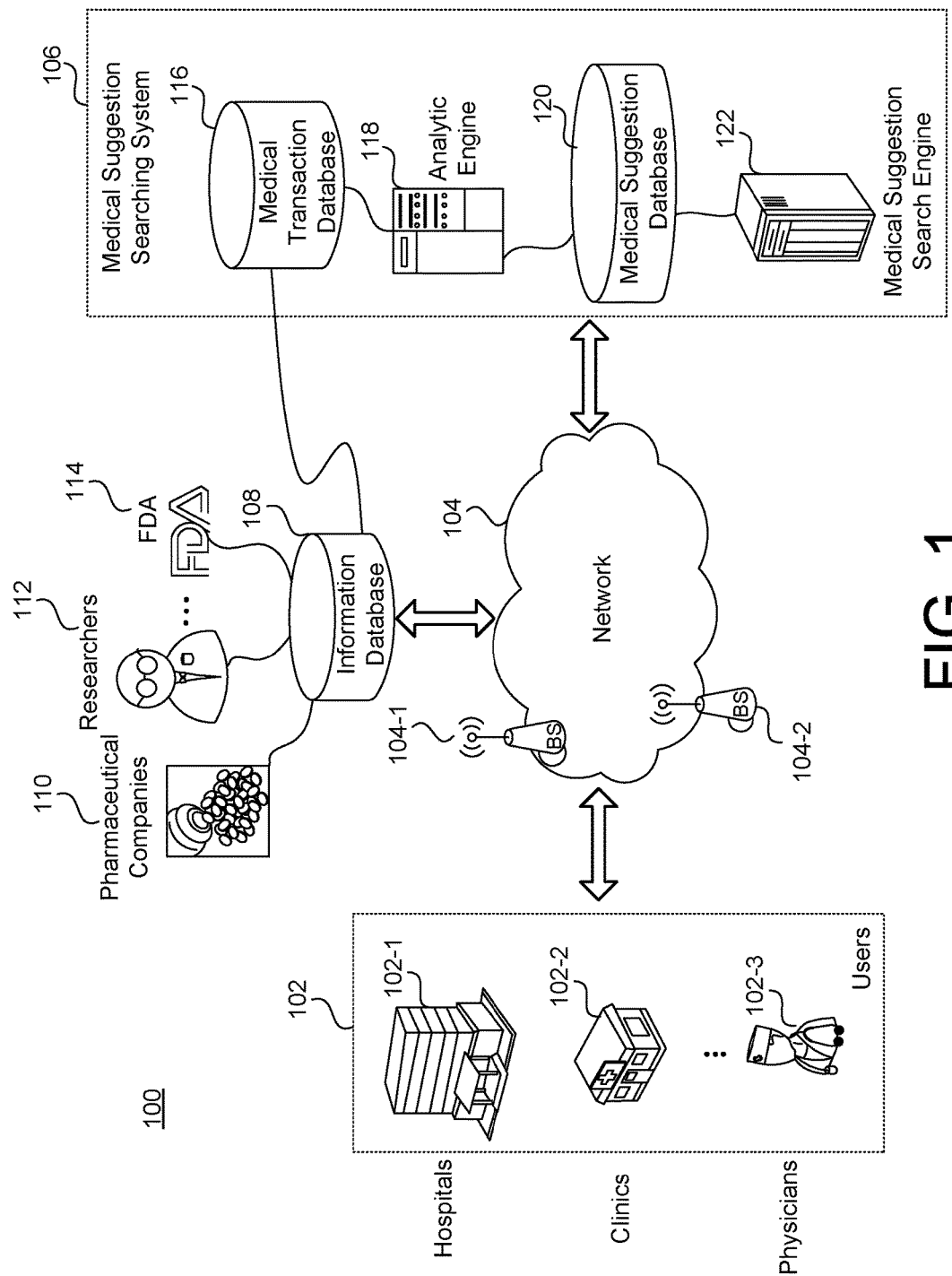
FIG. 1 is a high level depiction of an exemplary networked environment for providing medical suggestions, according to an embodiment of the present teaching.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The present teaching describes methods, systems, and programming aspects of automatically generating medical suggestions and searching appropriate medical suggestions for users based on medical information in various patient care dimensions, such as doctor specialty, patient profile, disease diagnosis, synonyms, etc. The users may include personnel in hospitals, clinics, and/or other health care facilities who are authorized to prescribe medication drugs, make other medical suggestions (e.g., physical therapies, diets, lab tests, radiology tests, etc.) to patients, or perform medication reconciliation.

According to various embodiments of the present teaching, medical suggestion searching method and system are disclosed. The disclosed method and system are capable of collecting any medical data from different sources, including internal medical transaction database and external medical information database such as database from pharmaceutical companies, researchers, and Food and Drug Administration (FDA). The disclosed medical suggestion searching method and system can identify candidate medical suggestions from the collected data and automatically process the candidate medical suggestions, e.g., based on statistical analytics, to generate confidence scores for each candidate medical suggestion. The candidate medical suggestions and their confidence scores may be processed and stored with respect to each patient care dimension, e.g., doctor specialty, patient profile, disease diagnosis, and synonyms. Based on the patient care setting, e.g., medical information in one or more dimensions received with a search request, the medical suggestion searching method and system can apply a mathematical approach to determine the medical suggestions that are suitable for the particular patient care setting.

The search can be performed based on any information in the patient care setting. That is, the medical suggestion searching method and system as disclosed in the present teaching allow very light search terms to be inputted by the user, thereby reducing time and typographic errors in making the medical suggestion search. The search results are not limited to medication drugs, but can also include non-drug medical suggestions, such as but not limited to, physical therapies, diets, lab tests, radiology procedures, or any other suitable modalities.

In addition, the medical suggestion searching method and system may obtain feedbacks with respect to the medication suggestions from, e.g., physician. As such, the feedback information can be used to dynamically evaluate the stored medical suggestions and/or their associated confidence scores so that information feedback from the actual usages of medical suggestions can be utilized to continuously improve the effectiveness of the medical suggestion searching method and system.

FIG. 1 is a high level depiction of an exemplary networked environment for providing medical suggestions, according to an embodiment of the present teaching. In FIG. 1, the networked environment 100 includes one or more users 102, a network 104, a medical suggestion searching system 106, an information database 108, and one or more sources 110, 112, 114 of the information database 108. The medical suggestion searching system 106 further includes a medical transaction database 116, an analytic engine 118, a medical suggestion database 120, and a medical suggestion search engine 122.

The network 104 may be a single network or a combination of different networks. For example, the network 104 may be a local area network (LAN), a wide area network (WAN), a public network, a private network, a proprietary network, a Public Telephone Switched Network (PSTN), the Internet, a wireless network, a virtual network, or any combination thereof. The network 104 may also include various network access points, e.g., wired or wireless access points such as base stations or Internet exchange points 104-1, . . . , 104-2, through which a data source may connect to the network 104 in order to transmit information via the network 104.

Users 102 may be of different types such as users connected to the network 104 via hospitals 102-1, clinics 102-2, or individual physicians 102-3. A user 102 may send search requests with information in any patient care dimensions and receive medical suggestions as search results from the medical suggestion search engine 122 of the medical suggestion searching system 106 via the network 104. The user 102 may perform any medical transactions based on the medical suggestions, such as prescribing medication drugs, recommending physical therapies and diets, and ordering lab and radiology tests. The medical transaction information, including the adopted medical suggestions, can be sent back to the medical suggestion searching system 106 and stored in the medical transaction database 116 via the network 104.

The medical suggestion searching system 106 may provide different medical suggestions to the users 102 and collect feedbacks related to medical transactions from the users 102. Medical suggestions returned by the medical suggestion searching system 106 are generated based, at least in part, on medical transaction data in the medical transaction database 116. The medical transaction database 116 may store different types of information. For example, it may store information related to prescription transactions received from the users 102. It may also store any drug-related information, which may be retrieved from, e.g., the information database 108. The medical transaction database 116 may also store information about prescriptions accumulated over time by the medical suggestion searching system 106. The information database 108 may store various types of knowledge about different drugs. For example, it may store information related to the composition or characteristics of different medication drugs and information related to medication reconciliation, provided by, e.g., pharmaceutical companies 110, research institutions 112, and/or FDA 114. As mentioned above, the medical suggestion searching system 106 can provide non-drug related medical suggestions as well. In some embodiments, the information database 108 may include information related to non-drug related medical transactions made by the users 102, such as physical therapy and diet recommendations and lab and radiology test orders. Knowledge about non-drug related medical suggestions may be included in the information database 108 as well.

The analytic engine 118 in the medical suggestion searching system 106 may analyze the information stored in the medical transaction database 116 and generate ranked candidate medical suggestions in each patient care dimension. In some embodiments, the candidate medical suggestions with their confidence scores are first stored in the medical suggestion database 120. A confidence score in this embodiment is indicative of a degree of match between the medical suggestion and medical information of a patient care dimension. A confidence score may be determined based on the total number of occurrence, frequency of occurrence, and/or recency of occurrence of a particular medical suggestion in the collected medical transaction data. Upon receiving a search request with medical information of one or more dimensions from a user 102, the medical suggestion search suggestion engine 122 may automatically identify medical suggestions based on the received information of each patient care dimension and select one or more medical suggestions as search results based on aggregated confidence scores for each medical suggestion. In some embodiments, the aggregated confidence score for each medical suggestion is calculated by applying a weighted summation approach or an un-weighted summation approach based on each confidence score of the medical suggestion with respect to each dimension.

Figure 2:
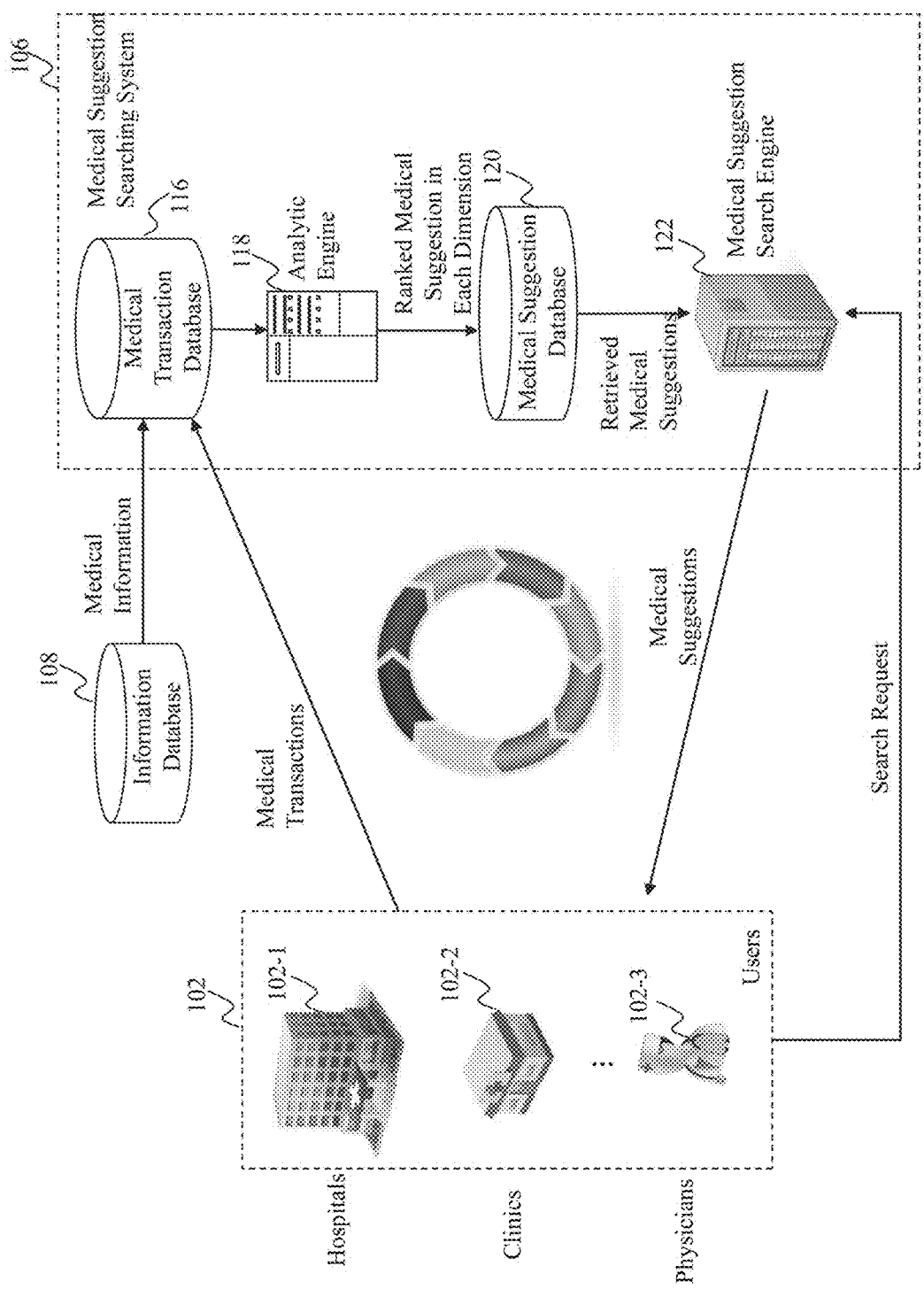
FIG. 2 is a high level diagram illustrating a feedback loop between users and a system for medical suggestion searching, according to an embodiment of the present teaching.

FIG. 2 is a high level diagram illustrating a feedback loop between users and the medical suggestion searching system 106, according to an embodiment of the present teaching. As shown in FIG. 2, medical transactions made by the users 102 and medical information from the information database 108 (e.g., knowledge about drugs and non-drug medical treatments and diagnostic procedures) may be fed into the medical transaction database 116 of the medical suggestion searching system 106. This can be performed periodically according to a schedule, e.g. every night, or in a continuous manner. The information stored in the medical transaction database 116 is automatically processed by the analytic engine 118 to generate medical suggestions with confidence scores with respect to each patient care dimension, which are in turn stored in the medical suggestion database 120. Some of the medical suggestions with their confidence scores stored in the medical suggestion database 120 can be retrieved by the medical suggestion search engine 122 as candidates of the medical suggestions made to the users 102. Upon receiving a search request from a user 102, the medical suggestion search engine 122 selects medical suggestions based on the overall degree of match between the medical suggestions and the received information of patient care dimensions, e.g., doctor specialty, patient profile, etc.

After receiving the medical suggestions made by the medical suggestion searching system 106 as search results, the users 102 may decide whether to adopt any of the medical suggestions and provide them to their patient. The medical transactions based on the adopted medical suggestions may be recorded in the medical transaction database 116 as an indication of effectiveness of the medical suggestions. Thus, a feedback loop is established so that the medical suggestion searching system 106 may use such continuously-fed medical transaction data to dynamically update the stored medical suggestions and/or their associated confidence scores.

Figure 3:
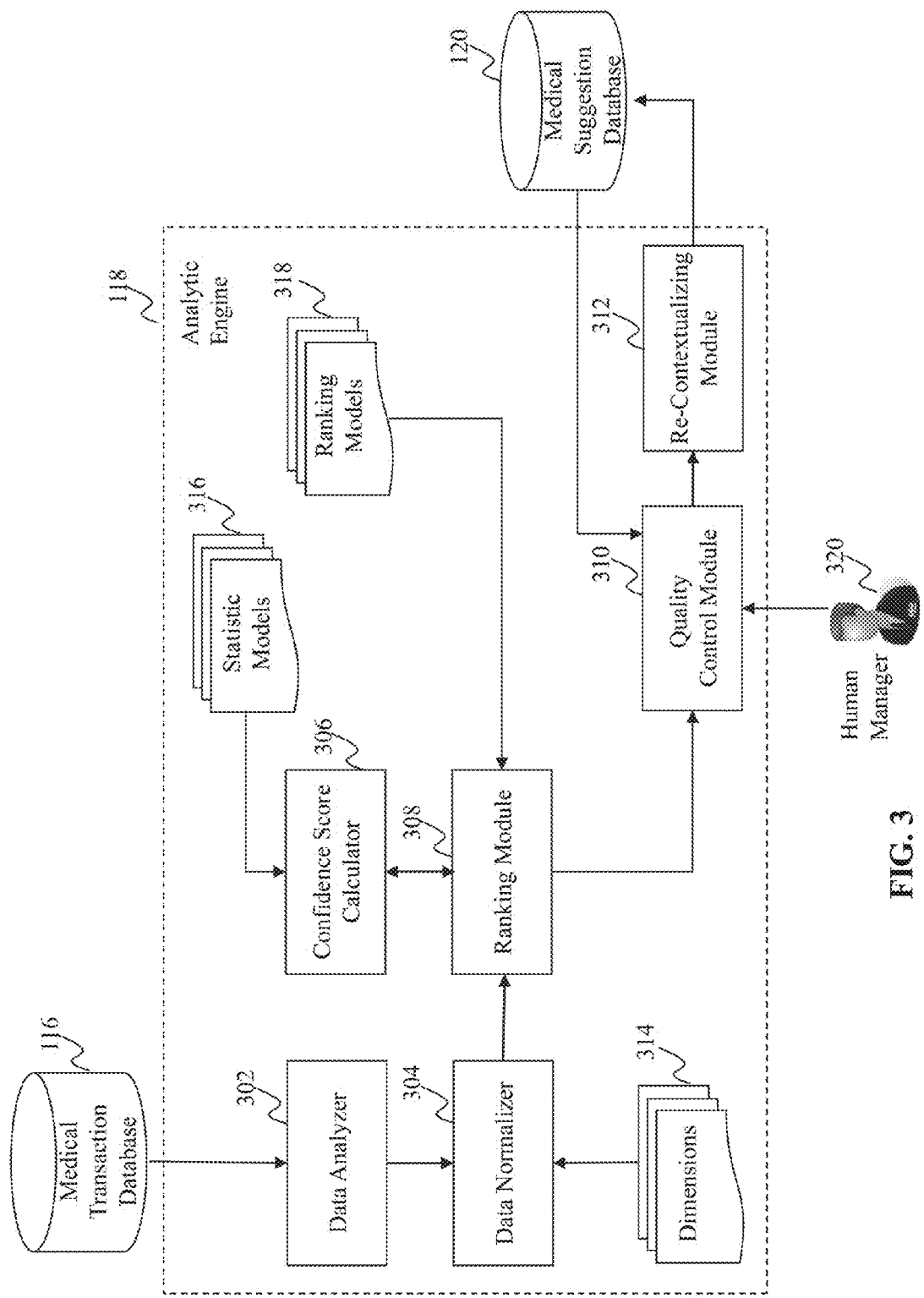
FIG. 3 illustrates an exemplary diagram of an analytic engine for providing medical suggestions, according to an embodiment of the present teaching.

FIG. 3 illustrates an exemplary diagram of the analytic engine 118 for medical suggestion generation, according to an embodiment of the present teaching. The analytic engine 118 is part of the medical suggestion searching system 106 (as shown in FIG. 1). In this embodiment, the analytic engine 118 includes a data analyzer 302, a data normalizer 304, a confidence score calculator 306, a ranking module 308, a quality control unit module 310, and a re-contextualizing module 312. The analytic engine 118 in this example receives information about medical transactions from the medical transaction database 116, generates medical suggestions with their confidence scores in each patient care dimension, and stores them in the medical suggestion database 120.

In this exemplary embodiment, the data analyzer 302 retrieves information from the medical transaction database 116. As discussed before, the information in the medical transaction database 116 may include data related to one or more medication drugs and/or information related to previous prescription transactions made by the users 102. The information may further include any non-drug related medical data from either the users 102 or any general medical knowledge sources. The data analyzer 302 analyzes the retrieved information to identify candidate medical suggestions. Each of the candidate medical suggestions may be with respect to multiple patient care dimensions, such as doctor specialty, patient profile, disease diagnosis, synonyms, etc. For example, a drug prescription may include a breast cancer drug prescribed by an oncologist (doctor specialty) to a female patient at the age of 55 (patient profile), who have been diagnosed as having stage 1 breast cancer (diseases diagnosis). By the data analyzer 302, this breast cancer drug is identified as a candidate medical suggestion with respect to each of the above-mentioned patient care dimensions (doctor specialty, patient profile, disease diagnosis).

In some embodiments, the data normalizer 304 automatically processes each of the identified candidate medical suggestions with respect to each patient care dimension 314 and generates normalized medical suggestion data. For example, based on some normalization model, the data normalizer 304 may identify new entries from the candidate medical suggestions and generate a fuzzy map to match new entries. Other normalization models may also be employed. For example, the data normalizer 304 may identify and remove duplicated candidate medical suggestions. The normalization models may be pre-configured in the analytic engine 118 for data normalization. Each configuration may also be dynamically adjusted, e.g. based on feedbacks from the users 102. The data normalizer 304 may determine which type of data (e.g., drug, diet, physical therapy, test, etc.) should be applied with what kind of normalization scheme. For each type of medical suggestion data to be normalized, appropriate normalization models are determined and applied accordingly. In some embodiments, the data normalizer 304 may receive existing medical suggestion data from the medical suggestion database 120 as well in order to identify new data entries and remove duplicated data entries.

In this embodiment, the confidence score calculator 306 calculates confidence scores of a medical suggestion with respect to a dimension based on some given model, e.g., statistic models 316. A confidence score is indicative of a degree of match between the medical suggestion and the medical information of the dimension. The statistic models 316 may be selected or determined based on a variety of considerations, such as the type of the medical suggestion data, the source of the medical suggestion data, the feedback associated with the medical suggestion data, and the likelihood that a medical suggestion will be provided to a user. The statistic models 316 may consider statistic information such as the total number of occurrence of a medical suggestion in the medical transaction database 116. For example; drug A has appeared 1,000 times in all the prescriptions stored in the medical transaction database 116. The statistic models 316 may consider the frequency of occurrence of a medical suggestion in the medical transaction database 116. For example, drug A appears 100 times per month in the prescriptions stored in the medical transaction database 116 in last year. The statistic models 316 may further consider the recency of occurrence of a medical suggestion in the medical transaction database 116. For example, the last time that drug A appeared in a prescription stored in the medical transaction database 116 is 35 days ago. It is understood that any other statistic information and combination thereof may be considered in the statistic models 316 for calculating confidence scores.

In addition to statistics information, other factors may be taken into consideration in calculating confidence scores in some embodiments. For example, a candidate medical suggestion that has been provided to users before and adopted by the users (positive feedback) may have a higher confidence score than another medical suggestion that has never been provided or adopted before (negative feedback). Confidence scores can also be higher when candidate medical suggestions pass checks for factors of rationality from FDA. Moreover, a confidence score is specific to a particular dimension, and each medical suggestion may have multiple confidence scores associated with different dimensions. Based on the statistic models 316, the confidence score calculator 306 calculates confidence scores for each candidate medical suggestion with respect to each dimension and sends the confidence scores to the ranking module 308.

In some embodiments, the ranking module 308 may rank the medical suggestions based on their confidence scores and a ranking model 318. The ranking model may be selected by the ranking module 308 from the ranking models 318, e.g. based on feedbacks from users. For example, according to one ranking model, a medical suggestion that has been more frequently adopted by users (positive feedback) is ranked higher than medical suggestions with negative feedback. In another example, a ranking model may include a cutoff threshold so that only medical suggestions with confidence scores above the threshold remain in the ranking Based on the ranking model and the confidence scores, the ranking module 308 generates a list of ranked medical suggestions with respect to each dimension.

The quality control module 310 in this embodiment controls quality of the medical suggestions and their confidence scoring before they can be stored in the medical suggestion database 120. The quality control module 310 may automatically compare each medical suggestion with previously qualified medical suggestions stored in the medical suggestion database 120. If a match can be found by the comparison, the matched medical suggestion is automatically qualified. Otherwise, a human review may be requested for the unmatched medical suggestions. As shown in FIG. 3, a human manager 320 can perform a human review for each unmatched prescription string to determine whether the unmatched medical suggestions should be qualified. In one example, the human manager 320 is an expert of the medical suggestions and is associated with the medical suggestion searching system 106. The quality control module 310 receives human reviews from the human manager 320 and determines whether to qualify each unmatched medical suggestion based on the human review result. The quality control module 310 then sends the qualified medical suggestions to the re-contextualizing module 312.

The re-contextualizing module 312 in this embodiment re-contextualizes the qualified medical suggestions, for example, drugs, and saves the re-contextualized medical suggestions into the medical suggestion database 120. The re-contextualization may include re-connecting each drug with a drug code, e.g. the national drug code (NDC). The re-contextualization may also include generating a nomenclature map having the qualified medical suggestions with confidence scores in each dimension (dimension maps) that is consistent with the stored dimension maps in the medical suggestion database 120.

Figure 4:
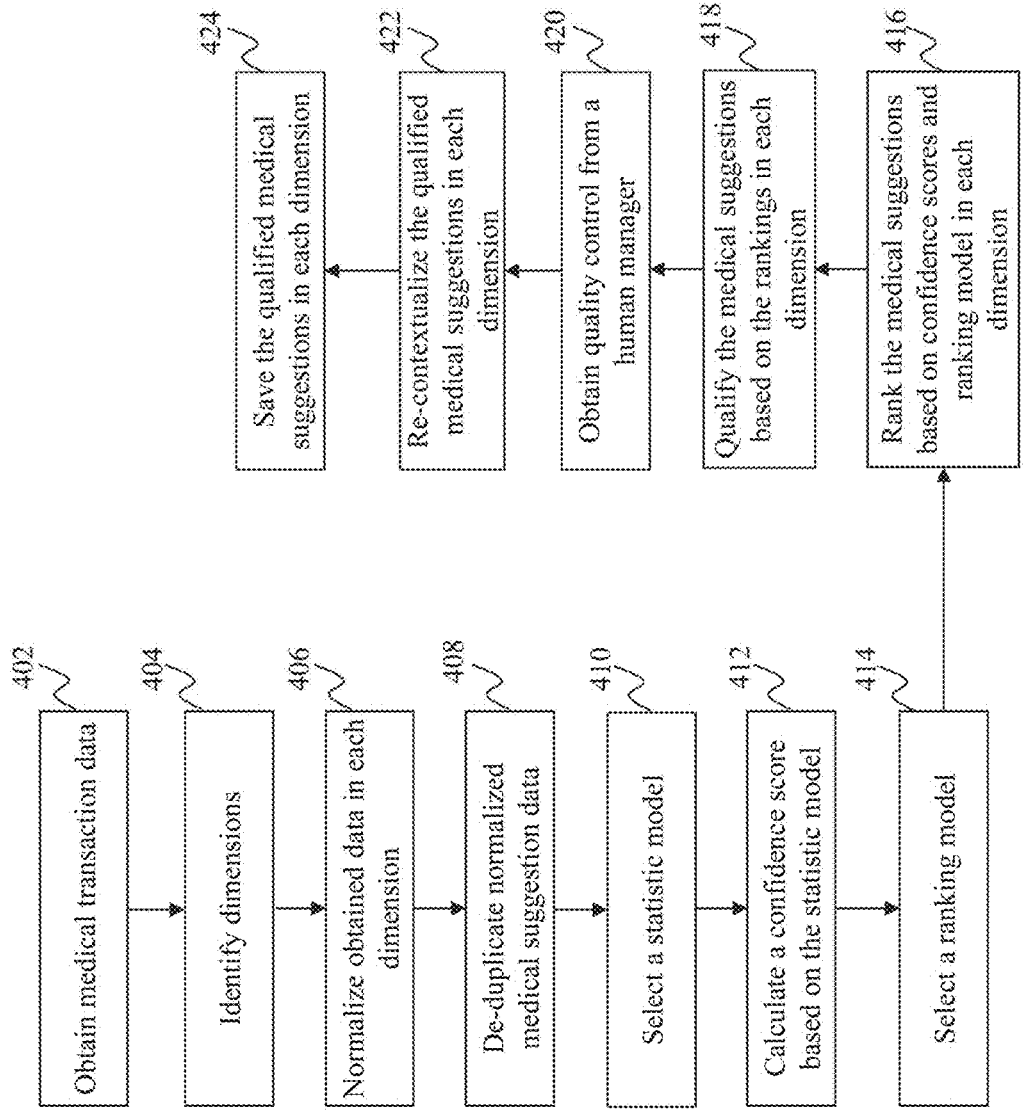
FIG. 4 is a flowchart of an exemplary process performed by the analytic engine for providing medical suggestions, according to an embodiment of the present teaching.

FIG. 4 is a flowchart of an exemplary process performed by an analytic engine, e.g. the analytic engine 118 shown in FIG. 3, for medical suggestion generation, according to an embodiment of the present teaching. Starting at 402, medical transaction data is obtained. At 404, patient care dimensions of interest are identified. At 406, the obtained data is normalized in each of the identified dimensions. At 408, the normalized medical suggestions are de-duplicated. At 410, a statistic model is selected for calculating confidence scores. At 412, confidence scores are calculated for each medical suggestion in each identified dimension based on the statistic model. At 414, a ranking model is selected. At 416, the medical suggestions are filtered and ranked based on their confidence scores and the ranking model in each dimension. At 418, some medical suggestions are automatically qualified based on their confidence scores and/or comparison between each medical suggestion and pre-qualified or pre-approved medical suggestions. At 420, quality control is performed by a human manager, which may happen when some medical suggestions cannot be matched with any pre-qualified medical suggestions based on the comparison at 418. At 422, the qualified medical suggestions are re-contextualized. At 424, the qualified and re-contextualized medical suggestions and their confidence scores in each dimension are stored into a medical suggestion database.

Figure 5:
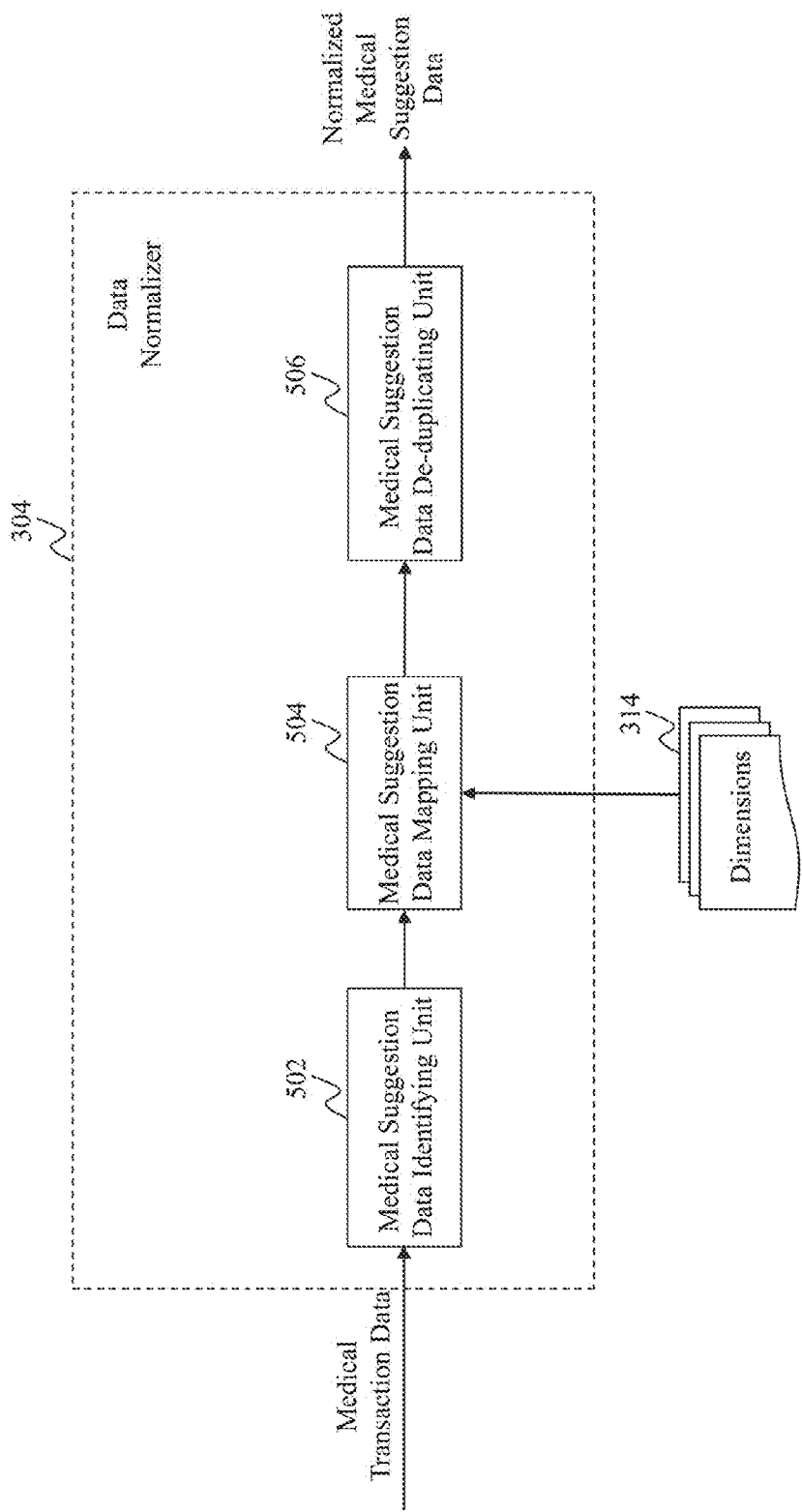
FIG. 5 illustrates an exemplary diagram of a data normalizer in the analytic engine, according to an embodiment of the present teaching.

FIG. 5 illustrates an exemplary diagram of the data normalizer 304 in the analytic engine 118, according to an embodiment of the present teaching. The data normalizer 304 in this example includes a medical suggestion data identifying unit 502, a medical suggestion data mapping unit 504, and a medical suggestion data de-duplicating unit 506.

The medical suggestion data identifying unit 502 identifies various types of medical suggestions from the collected medical transaction data. For example, medication drugs can be identified from drug prescriptions and newly approved drug list from FDA; lab and radiology tests may be identified from test order and result sheets. Each medical suggestion is identified with additional information related to any patient care dimension, such as the doctor specialty, patient's age, gender, diagnosis, etc. In some embodiments, the medical suggestion data identifying unit 502 also identifies whether a medical suggestion is a new entry by comparing it with the existing medical suggestion data (e.g., dimension maps) stored in the medical suggestion database 120.

The medical suggestion data mapping unit 504 in this embodiment maps each of the identified medical suggestions into the corresponding dimensions 314 based on the dimensional information associated with the medical suggestion. For example, if the doctor specialty and the patient's age can be identified from a drug prescription, then the drug, as a new medical suggestion entry, can be mapped into both the doctor specialty and patient age dimensions by the medical suggestion data mapping unit 504. The medical suggestion data de-duplicating unit 506 in this embodiment removes and/or consolidates duplicated medical suggestion entries. For example, the same drug may have different aliases, which can be consolidated as a single medical suggestion entry.

Figure 6:
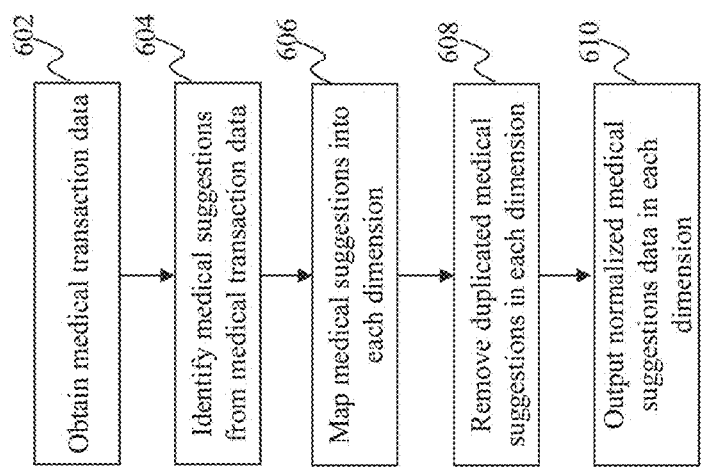
FIG. 6 is a flowchart of an exemplary process performed by the data normalizer, according to an embodiment of the present teaching.

FIG. 6 is a flowchart of an exemplary process performed by a data normalizer, e.g. the data normalizer 304 in FIG. 3, according to an embodiment of the present teaching. Starting at 602, medical transaction data is obtained, such as drug prescriptions and test order and result sheets. At 604, medical suggestions are identified from the medical transaction data. The medical information of patient care dimension may be identified as well. At 606, medical suggestions are mapped into each dimension based on the identified medical information. At 608, duplicated medical suggestions are removed and/or consolidated in each dimension. At 610, the normalized medical suggestions in each dimension are outputted.

Figure 7:
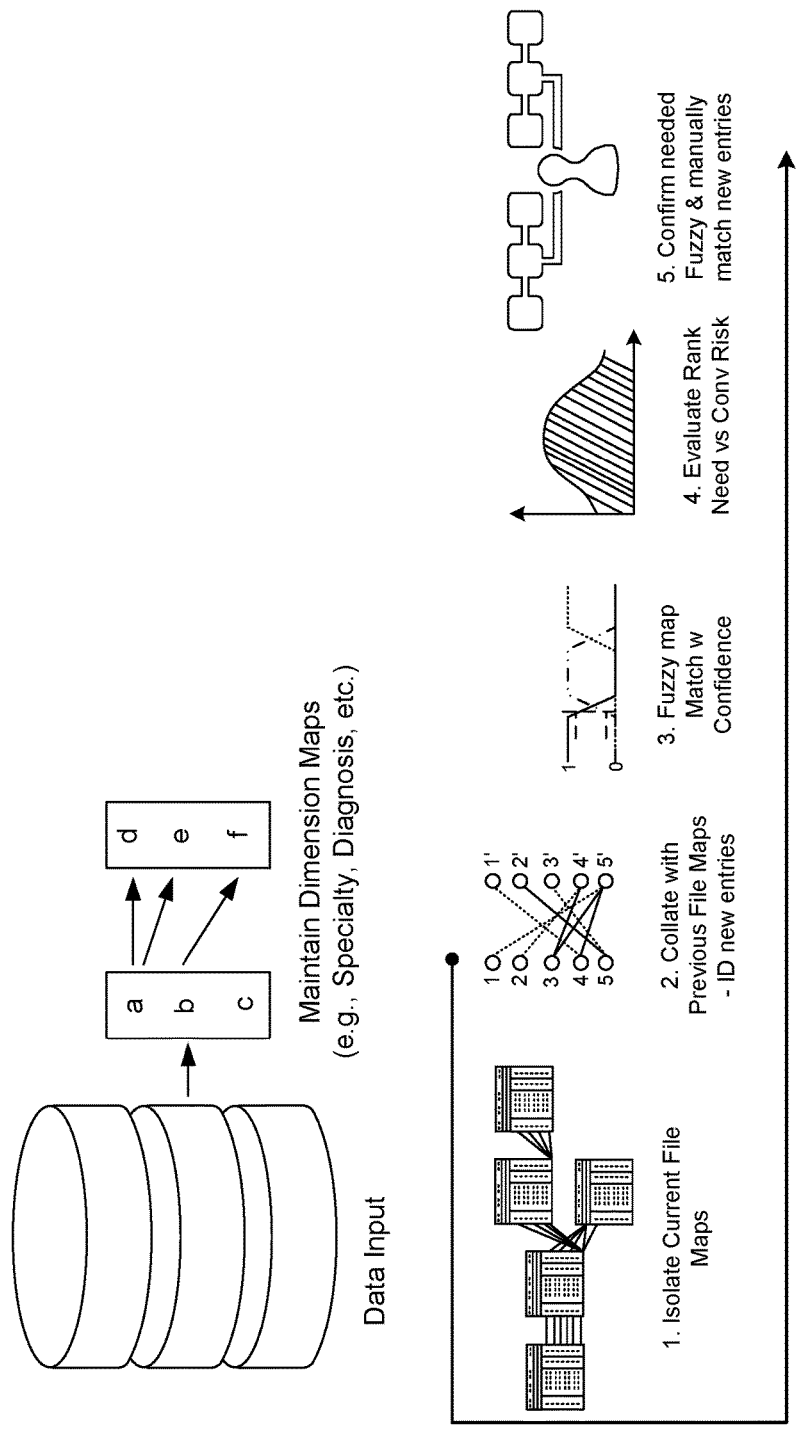
FIGS. 7-8 illustrate exemplary functions performed by the data normalizer, according to various embodiments of the present teaching.
Figure 8:
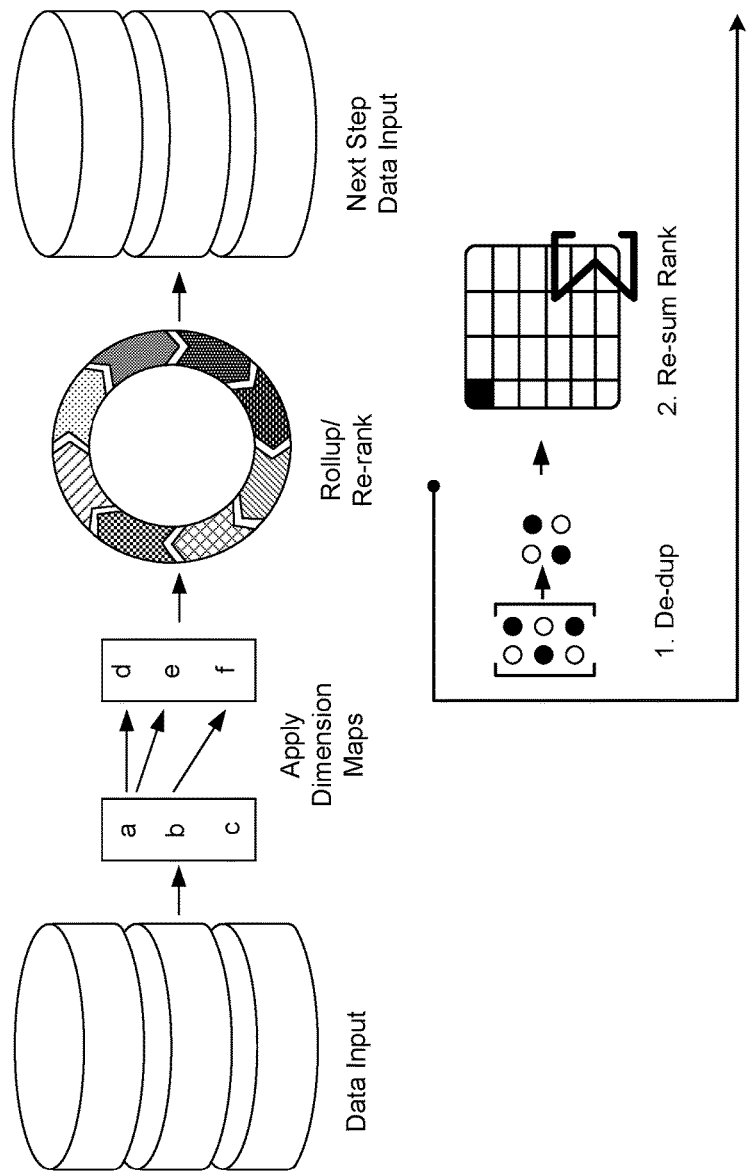

FIGS. 7-8 illustrate exemplary functions performed by the data normalizer 304, according to various embodiments of the present teaching. As shown in FIG. 7, a plurality of functions related to maintaining dimension maps may be performed, e.g., by the data normalizer 304. The first function relates to isolating current file maps. That is, the newly received medical transaction data may be separated based on dimensions and/or types of the medical suggestions. The second function relates to collating the current file maps with previous file maps to identify new entries, i.e. the medical suggestions that have not been stored in the medical suggestion database. The third function relates to generating a fuzzy map to characterize relations between the new entries and/or relations between the new entries and the existing entries. Each relation may be associated with a confidence score representing a confidence about such relation. The fourth function relates to evaluating rank need versus conversion risk. The fifth function relates to confirming fuzzy relations generated by the third function and manually matching the new entries based on the fuzzy map if needed. The fifth function may be performed together by the data normalizer 304 and a human manager. In this example, the data normalizer 304 may retrieve data from the medical suggestion database 120 directly. As shown in FIG. 8, a plurality of functions related to rolling up/re-ranking may be performed, e.g., by the data normalizer 304. The first function relates to de-duplication, and the second function relates to re-sum rank after de-duplication.

Figure 9:
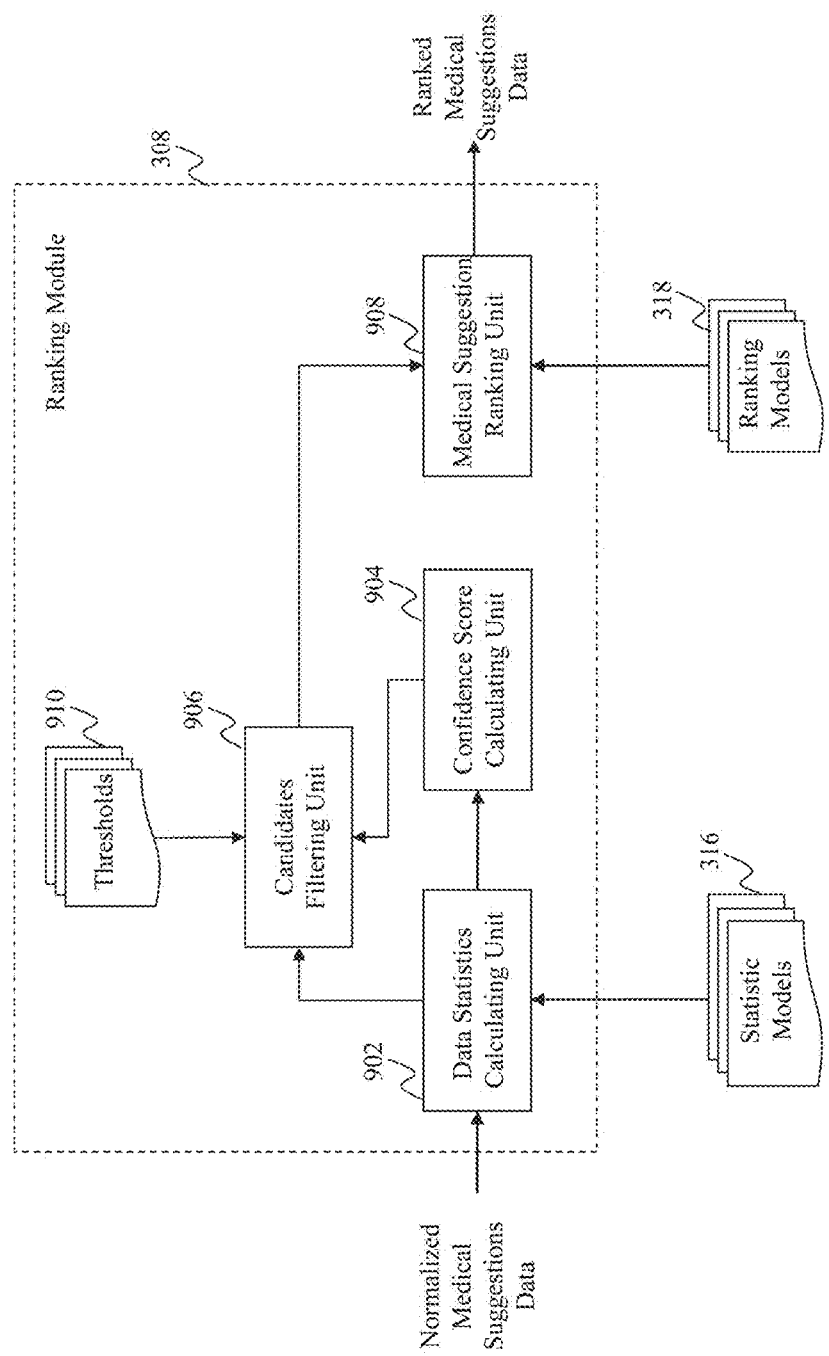
FIG. 9 illustrates an exemplary diagram of a ranking module in the analytic engine, according to an embodiment of the present teaching.

FIG. 9 illustrates an exemplary diagram of a ranking module 308 in an analytic engine, e.g. the analytic engine 118 in FIG. 3, according to an embodiment of the present teaching. The ranking module 308 in this example includes a data statistics calculating unit 902, a confidence score calculating unit 904, a candidate filtering unit 906, and a medical suggestion ranking unit 908.

The data statistics calculating unit 902 calculates statistic measures of a medical suggestion based on the desired statistic models 316. As mentioned above, based on the specific statistic model applied in an embodiment, one or more statistic measures, such as total occurrence, frequency of occurrence, or recency of occurrence, are calculated for a medical suggestion based on the normalized medical suggestion data with respect to each patient care dimension. The calculated statistic measures are provided to the confidence score calculating unit 904 for calculating confidence scores. The confidence score is indicative of a degree of match between the medical suggestion and the medical information of the dimension. The larger the confidence score is, the more likely that the corresponding medical suggestion matches with the medical information of the dimension. In one example, the values of some statistic measures, e.g., the total occurrence or the frequency of occurrence, may be used directly as the confidence score. For example, a popular drug that has been widely and frequency used by doctors in a particular specialty has a relatively high confidence score with respect to the doctor specialty, which indicates that it is likely that the same drug would be suggested by a doctor in the same specialty in the future. In another example, multiple statistic measures may be combined with respective weights. For example, the recency may be weighted by a time decay factor and used to adjust the total occurrence and/or frequency of occurrence when computing the confidence score.

The statistic measures and/or the confidence scores are sent to the candidate filtering unit 906 in this embodiment. It is understood that the total number of candidate medical suggestions in each dimension may be very large. Thus, candidate medical suggestions may be filtered in each dimension by comparing one or more statistic measures and/or the confidence score with thresholds 910. In one example, if the total occurrence of a medical suggestion in the existing medical suggestion data is less than a predefined threshold, then the medical suggestion is excluded from future consideration. In another example, the confidence score of a medical suggestion is compared with a threshold to determine whether the medical suggestion should be kept. Nevertheless, the remaining candidate medical suggestions are ranked by the medical suggestion ranking unit 908 based on their confidence scores and the ranking models 318. In some embodiments, a predefined number of entries in each dimension is used to further filter the ranked candidate medical suggestions. For example, after ranking, only the top 1,000 drugs in each dimension are kept for future use.

Figure 10:
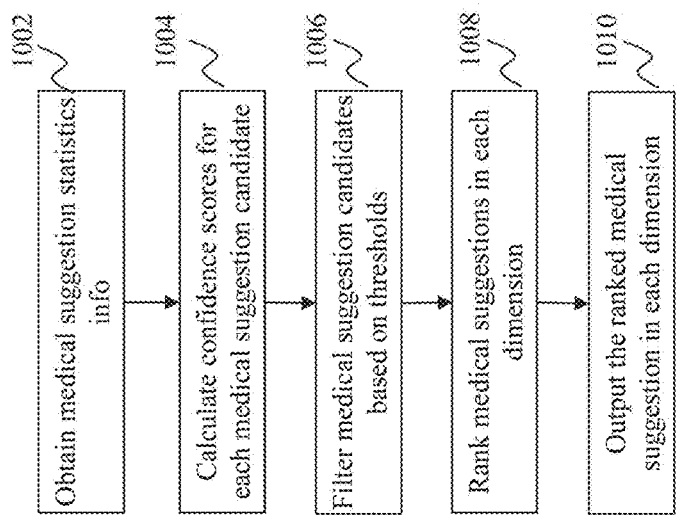
FIG. 10 is a flowchart of an exemplary process performed by the ranking module, according to an embodiment of the present teaching.

FIG. 10 is a flowchart of an exemplary process performed by a ranking module, e.g. the ranking module 308 in FIG. 9, according to an embodiment of the present teaching. Starting at 1002, medical suggestion statistic information (e.g., statistic measures) is obtained for each medical suggestion. At 1004, confidence scores are calculated for each candidate medical suggestion in each dimension. At 1006, candidate medical suggestions are filtered based on predefined thresholds. At 1008, the remaining medical suggestions are ranked based on their confidence scores in each dimension. At 1010, the ranked medical suggestions are outputted in each dimension.

Figure 11:
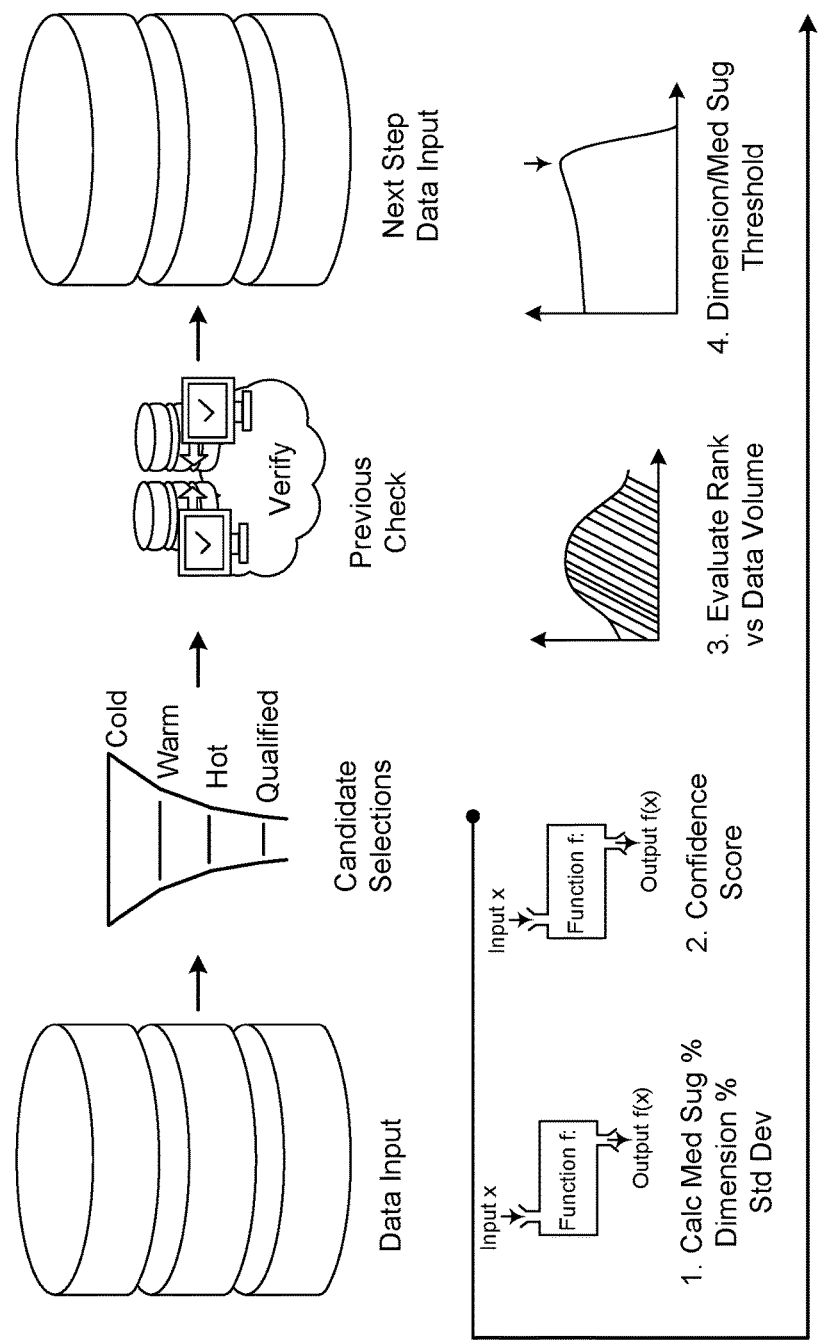
FIG. 11 illustrates exemplary functions performed by the ranking module, according to an embodiment of the present teaching.

FIG. 11 illustrates exemplary functions performed by the ranking module 308, according to an embodiment of the present teaching. As shown in FIG. 11, a plurality of functions related to candidate selection and ranking may be performed, e.g. by the ranking module 308. The first function relates to obtaining or calculating medical suggestion related statistics, e.g. the percentage of medical suggestions related to a given dimension, the standard deviation of number of medical suggestions related to each dimension, etc. The second function relates to obtaining confidence scores for each medical suggestion. The third function relates to evaluating rank versus data volume. The fourth function relates to determining a threshold based on the evaluation by the third function. A candidate medical suggestion is selected and stored, if the confidence score of the medical suggestion is above the determined threshold in a dimension.

Figure 12:
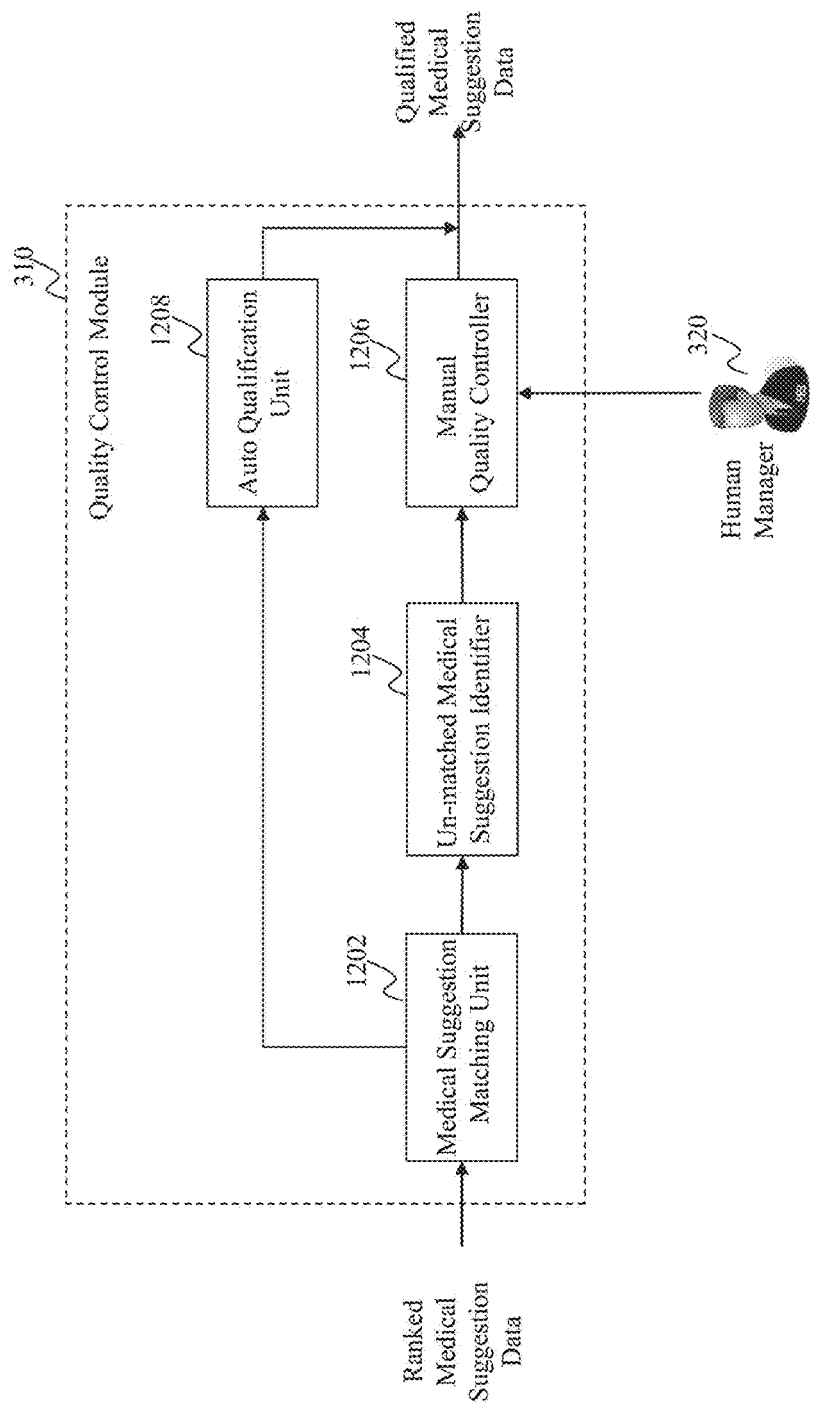
FIG. 12 illustrates an exemplary diagram of a quality control unit in the analytic engine, according to an embodiment of the present teaching.

FIG. 12 illustrates an exemplary diagram of a quality control module 310 in an analytic engine, e.g. the analytic engine 118 in FIG. 3, according to an embodiment of the present teaching. The quality control module 310 in this example includes a medical suggestion matching unit 1202, an un-matched medical suggestion identifier 1204, a manual quality controller 1206, and an auto qualification unit 1208.

The medical suggestion matching unit 1202 in this example may compare each candidate medical suggestion with pre-qualified medical suggestions and send the medical suggestion to either the un-matched medical suggestion identifier 1204 or the auto qualification unit 1208 based on the comparison result. If a match is found for the candidate medical suggestion based on the comparison result, the medical suggestion is sent to the auto qualification unit 1208 for auto qualification. Otherwise, if no match is found based on the comparison result, the candidate medical suggestion is sent to the un-matched medical suggestion identifier 1204. The un-matched medical suggestion identifier 1204 may identify the un-matched medical suggestions, i.e. un-validated medical suggestions, and may send them to the manual quality controller 1206 for human review. The manual quality controller 1206 may obtain human review from the human manager 320 regarding each un-matched medical suggestion and qualify some un-matched medical suggestions based on the human review. The auto qualification unit 1208 may automatically qualify medical suggestions that are matched with pre-qualified medical suggestions. The qualified medical suggestion data from the auto qualification unit 1208 and the manual quality controller 1206 are sent to the re-contextualizing module 312.

Figure 13:
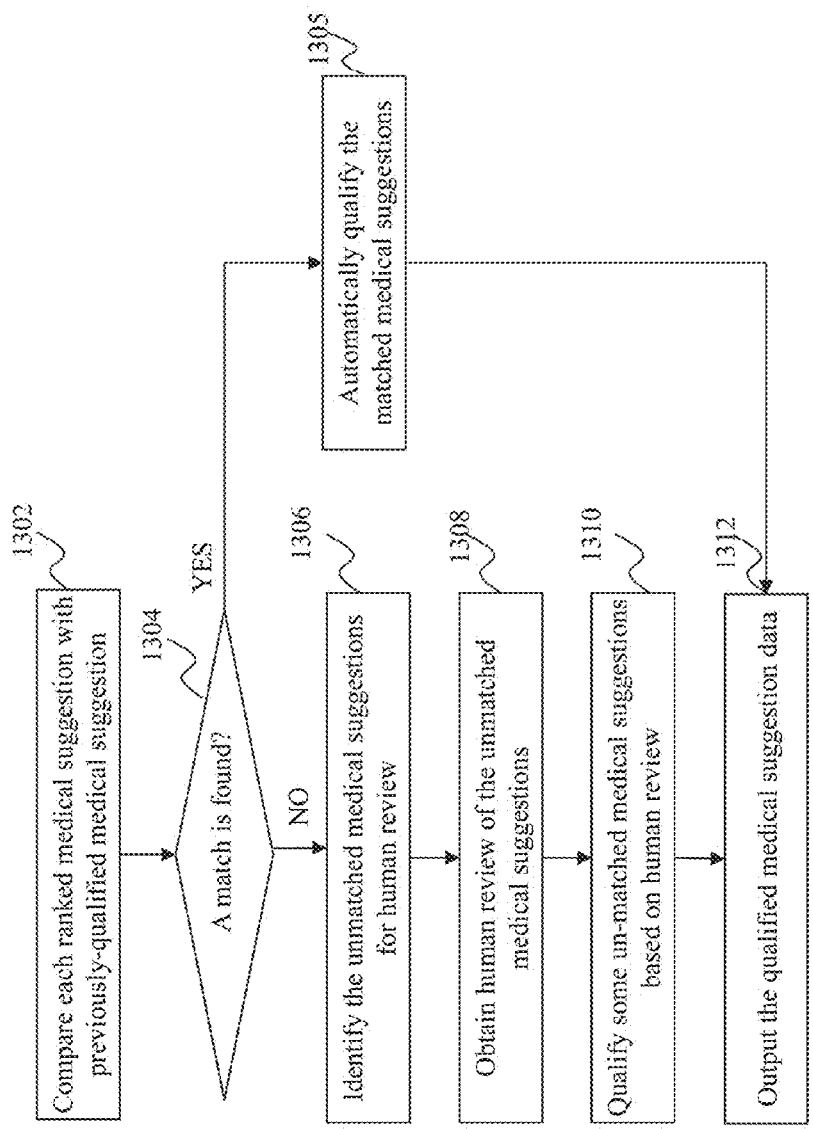
FIG. 13 is a flowchart of an exemplary process performed by the quality control unit, according to an embodiment of the present teaching.

FIG. 13 is a flowchart of an exemplary process performed by a quality control module, e.g. the quality control module 310 in FIG. 12, according to an embodiment of the present teaching. Starting at 1302, each candidate medical suggestion is compared with previously qualified medical suggestions. At 1304, it is determined whether a match is found for the medical suggestion based on the comparison result at 1302. If so, the process proceeds to 1305, where the matched medical suggestions are automatically qualified. If no match is found for the medical suggestion based on the comparison result at 1302, the process proceeds to 1306, where the un-matched medical suggestions are identified for human review. At 1308, human review is performed for each un-matched medical suggestion. At 1310, one or more un-matched medical suggestions are qualified based on the human review result. At 1312, the qualified medical suggestions are outputted, e.g., for re-contextualization.

Figure 14:
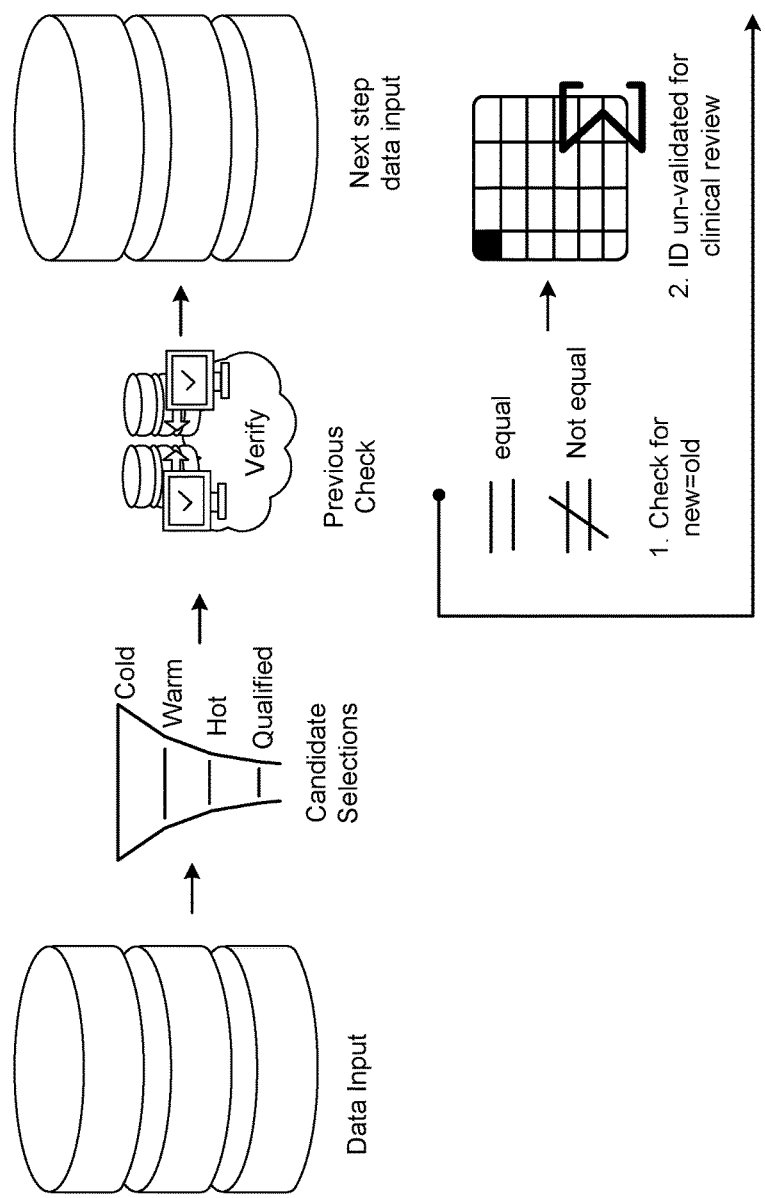
FIGS. 14-15 illustrate exemplary functions performed by the quality control unit, according to various embodiments of the present teaching.
Figure 15:
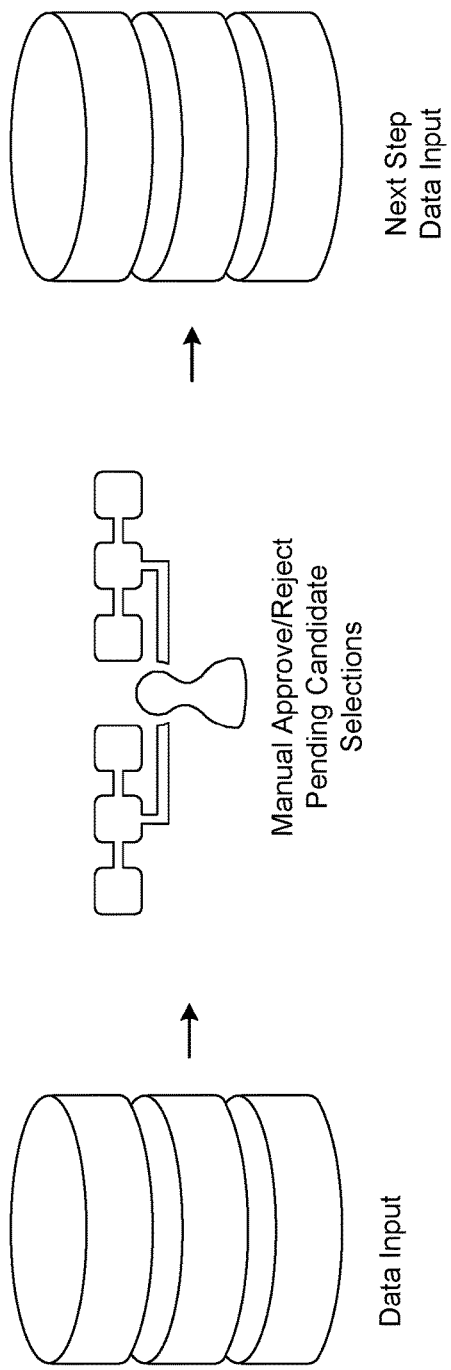

FIGS. 14-15 illustrate functions that can be performed by a quality control module in an analytic engine, e.g., the analytic engine 118 in FIG. 3, according to an embodiment of the present teaching. As shown in FIG. 14, a plurality of functions may be performed, e.g. by the quality control module 310. The first function relates to checking whether a new medical suggestion is equal to an existing pre-qualified medical suggestion. The second function relates to identifying the new medical suggestions that do not match any existing pre-qualified medical suggestions, i.e. the un-validated medical suggestions. The third function as shown in FIG. 15 relates to performing human review of the un-validated medical suggestions to determine a manual qualification for each un-validated medical suggestion. The first and second functions in FIG. 14 can be performed automatically by the quality control module 310; the third function in FIG. 15 can be performed by the quality control module 310 with human intervention, e.g., by the human manager 320 for manual approval or rejection of pending candidate selections.

Figure 16:
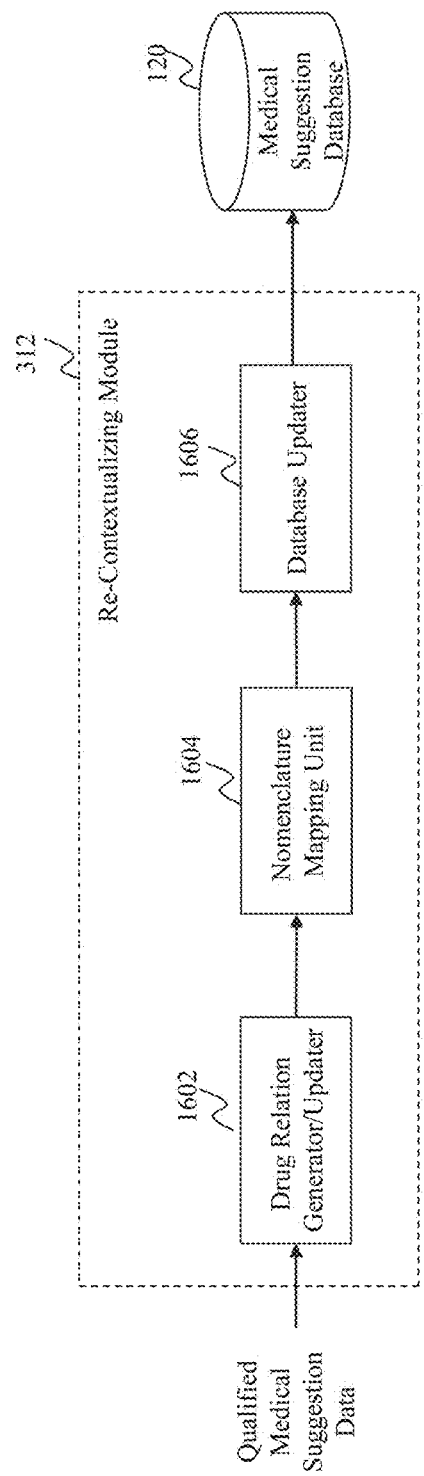
FIG. 16 illustrates an exemplary diagram of a re-contextualizing unit in the analytic engine, according to an embodiment of the present teaching.

FIG. 16 illustrates an exemplary diagram of a re-contextualizing module in an analytic engine, e.g. the analytic engine 118 in FIG. 3, according to an embodiment of the present teaching. The re-contextualizing module 312 in this example includes a drug relation generator/updater 1602, a nomenclature mapping unit 1604, and a database updater 1606. The re-contextualizing module 312 is described in this embodiment for performing drug re-contextualizing. It is understood that other types of medical suggestions, such as diets, physical therapies, etc., may be re-contextualized by the re-contextualizing module 312 in a similar manner. The drug relation generator/updater 1602 in this example may create or update drug relations by re-contextualizing each drug concept with one or more drug codes. The nomenclature mapping unit 1604 may generate nomenclature maps with the qualified medical suggestions, e.g., drugs, in each patient care dimension. The database updater 1606 in this example may update the medical suggestion database 120 by storing the re-contextualized drugs into the medical suggestion database 120.

Figure 17:
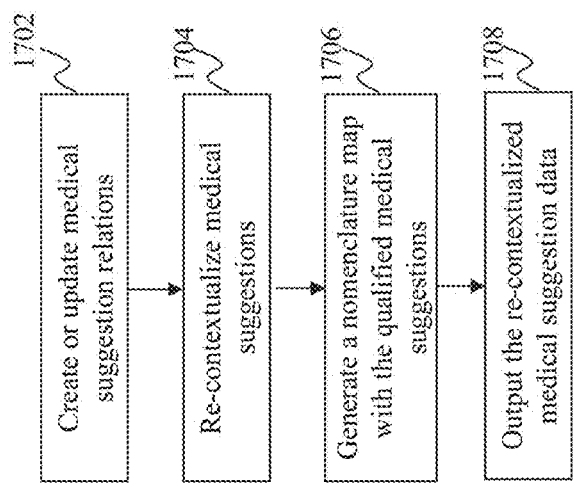
FIG. 17 is a flowchart of an exemplary process performed by the re-contextualizing unit, according to an embodiment of the present teaching.

FIG. 17 is a flowchart of an exemplary process performed by a re-contextualizing module, e.g. the re-contextualizing module 312 in FIG. 16, according to an embodiment of the present teaching. Starting at 1702, medical suggestion relations are created or updated. At 1704, medical suggestions are re-contextualized. For example, each medical suggestion may be mapped to Logical Observation Identifiers Names and Codes (LOINC), billing codes, etc. At 1706, nomenclature maps are generated with the qualified medical suggestions in each patient care dimension. At 1708, the re-contextualized medical suggestions are sent to the medical suggestion database 120.

Figure 18:
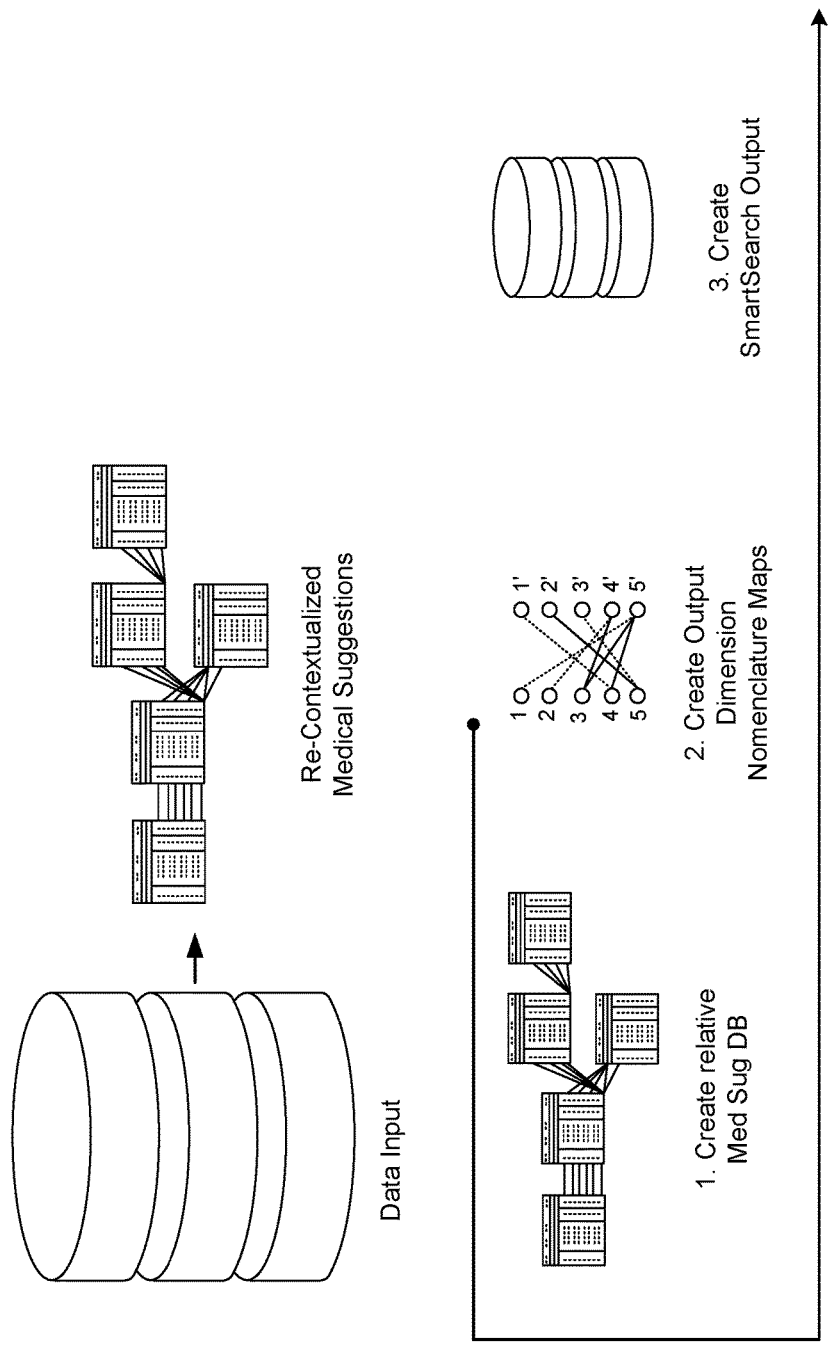
FIG. 18 illustrates exemplary functions performed by the re-contextualizing unit, according to an embodiment of the present teaching.

FIG. 18 illustrates functions that can be performed by a re-contextualizing module in an analytic engine, e.g. the analytic engine 118 in FIG. 3, according to an embodiment of the present teaching. As shown in FIG. 18, a plurality of functions may be performed, e.g. by the re-contextualizing module 312. The first function relates to creating a relative medical suggestion database. As mentioned above, medical suggestions may be re-contextualizing and mapped to LOINC codes, billing codes, etc.

Figure 19:
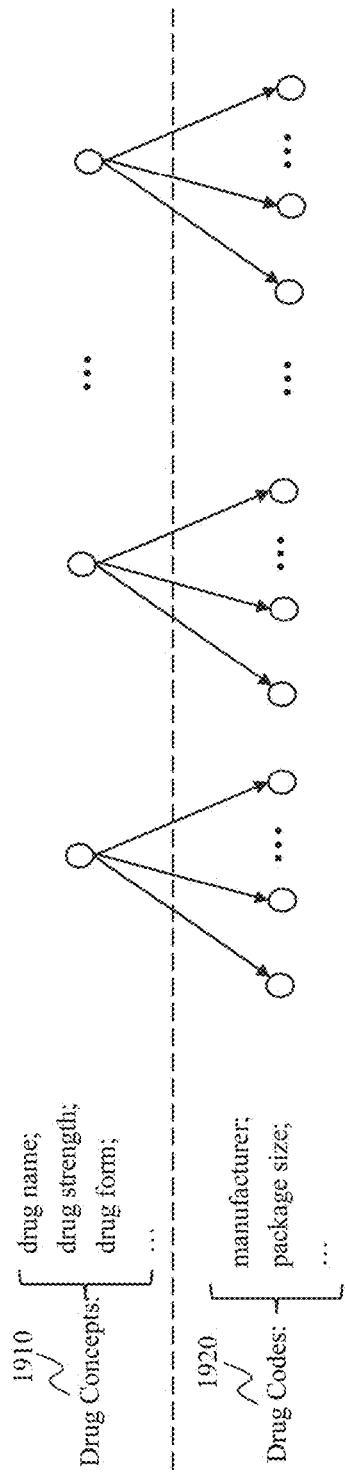
FIG. 19 illustrates re-contextualizing of medical suggestion data from drug concepts to drug codes, according to an embodiment of the present teaching.

FIG. 19 illustrates re-contextualizing drug data from drug concepts to drug codes, according to an embodiment of the present teaching. Each drug may have a plurality of drug concepts 1910. Each drug concept can specify some information related to the drug, including but not limited to, the drug name (e.g., Tylenol, Amoxicillin), drug strength (e.g., 500 mg, 300 mg), and drug form (e.g., tablet, capsule). Thus, a drug can be produced with different drug concepts, in accordance with different drug names, different drug strengths, and/or different drug forms. Each drug concept can be associated with a plurality of drug codes 1920. Each drug code can specify additional information related to the drug concept, including but not limited to, the manufacturer (e.g., CVS, Walgreen) and package size (e.g., 50 tablets, 200 tablets). Thus, a drug or drug concept can be sold in the market with different drug codes, in accordance with different manufacturers and/or different package sizes. In one example, the drug code can be the NDC.

Back to FIG. 18, the candidate drugs have been previously processed on the drug concept level. Thus, before the re-contextualization, the drugs have been ranked and/or qualified without taking into consideration of the information about the manufacturers and package sizes. By creating relative drug database and re-contextualizing the drugs, each drug is associated with one or more drug codes, in addition to the associated drug concepts. In one embodiment, after the drugs are ranked on the drug level and drug concept level, the drugs can be further ranked and qualified on the drug code level (e.g. by different NDCs). In this manner, each drug concept is re-contextualized with different drug codes.

As mentioned above, the medical suggestion modalities are not limited to drug and can include non-drug related medical suggestions, such as diet, physical therapies, lab tests, or radiology procedures, etc. Those medical modalities may be re-contextualized and mapped to other suitable medical suggestion codes, such as LOINC codes, billing codes, etc.

The second function in FIG. 18 relates to generating nomenclature maps in each patient dimension with the qualified medical suggestions. The third function in FIG. 18 relates to outputting the re-contextualized medical suggestions to, e.g., the medical suggestion database 120.

FIG. 20 illustrates an exemplary medical suggestion data map in one dimension, according to an embodiment of the present teaching. As mentioned above, qualified medical suggestions with their confidence scores may be stored in the medical suggestion database 120 in the form of nomenclature dimension maps. Each nomenclature dimension map may include one or more types of medical suggestions with their confidence scores with respect to a particular dimension. In this example, the map includes qualified medical suggestions with their confidence scores with respect to the "doctor specialty" dimension. Each of the qualified medical suggestions (medical suggestion 1, medical suggestion 2, . . . ) has confidence scores with respect to each doctor specialty (Cardiology, Neurosurgery, . . . ). For example, the confidence score of medical suggestion 1 with respect to Cardiology indicates a degree of match between medical suggestion 1 and Cardiology. In one example, such confidence score may be the number of total occurrence that cardiologists prescribed medical suggestion 1 determined based on data in the medical transaction database 116. Similarly, other nomenclature dimension maps may include qualified medical suggestions with their confidence scores with respect to other dimensions, e.g., patient age, gender, disease diagnosis, etc. The nomenclature dimension maps may also be organized based on the types of medical suggestions. That is, different types of medical suggestions may be arranged in different dimension maps. In other embodiments, multiple types of medical suggestions may be mixed up in the same dimension map.

Figure 21:
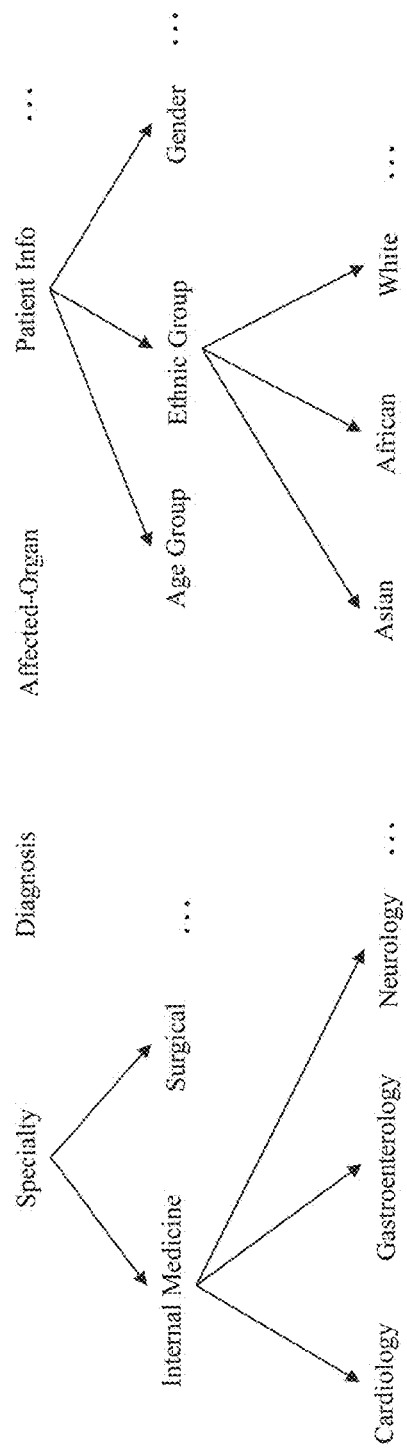
FIG. 21 illustrates an exemplary taxonomy of patient care dimensions used in medical suggestion searching, according to an embodiment of the present teaching.

FIG. 21 illustrates an exemplary taxonomy of dimensions used in medical suggestion searching, according to an embodiment of the present teaching. It is understood that the patient care dimensions may be specified at different granularities, which would in turn affect how the nomenclature dimension maps are organized. As one example shown in FIG. 21, at the roughest granularity level (highest level of the taxonomy), patient care dimensions include, for example, doctor specialty, diagnosis, affected-organ, patient profile, etc. Some of these high level dimensions may further include lower level dimensions. For example, doctor specialty may be divided into internal medicine, surgical, etc., and internal medicine may be further specified as including cardiology, gastroenterology, neurology, etc. Similarly, the patient profile dimension may be divided into age group, ethnic group, gender, etc. The taxonomy of dimensions may be used as guidance for building up the dimension maps of the medical suggestion data and for receiving user search terms (information of patient care dimensions received with each search request). It is understood that any other suitable taxonomy of dimensions may be applied as well.

Figure 22:
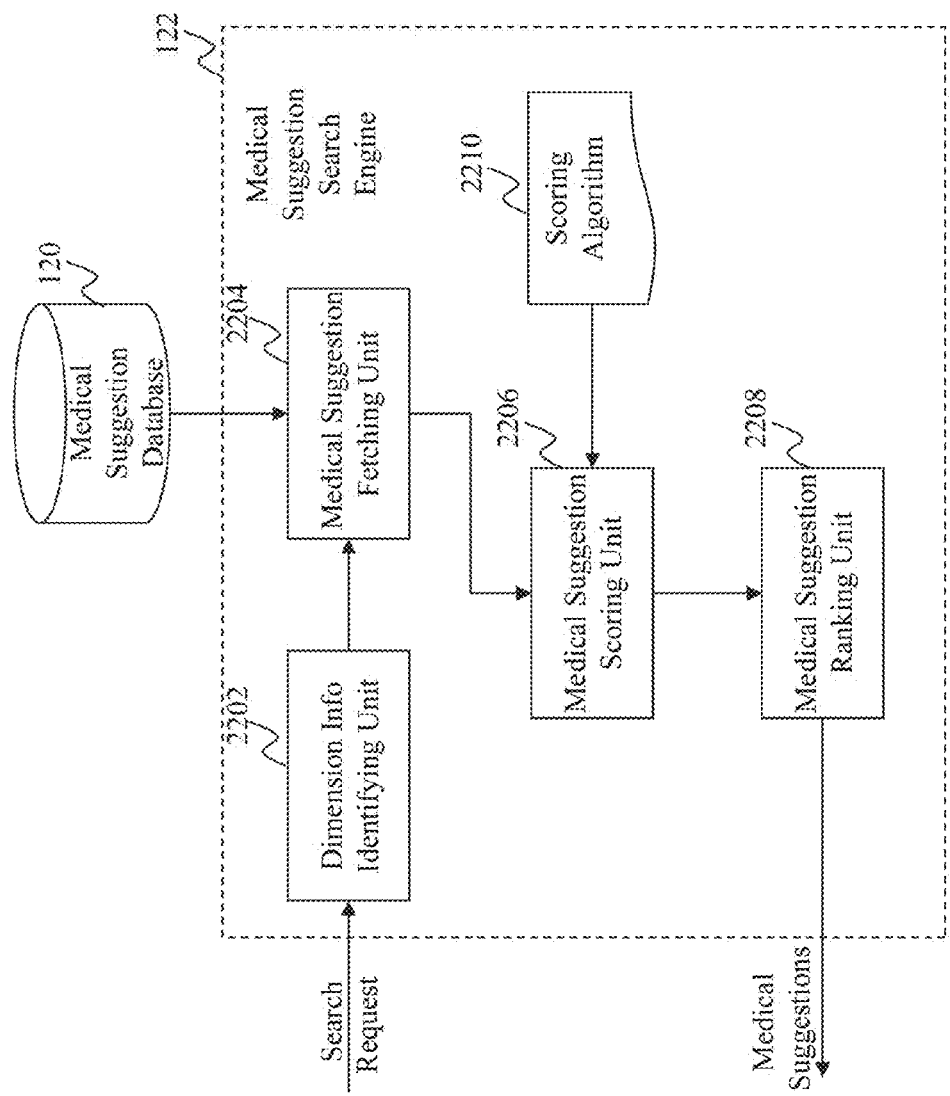
FIG. 22 illustrates an exemplary diagram of a medical suggestion search engine, according to an embodiment of the present teaching.

FIG. 22 illustrates an exemplary diagram of a medical suggestion search engine, according to an embodiment of the present teaching. The medical suggestion search engine 122 may receive a search request from users 102 with medical information of any patient care dimensions and return medical suggestions as search results to the users 102. The medical suggestion search engine 122 in this embodiment includes a dimension information identifying unit 2202, a medical suggestion fetching unit 2204, a medical suggestion scoring unit 2206, and a medical suggestion ranking unit 2208.

The dimension information identifying unit 2202 in this embodiment receives the search request and identifies relevant medical information in any patient care dimensions. In this embodiment, users 102 have the flexibility to provide any medical information of a patient to initiate the search. For example, users 102 may choose to provide limited information, such as just the doctor's specialty or the patient's diagnosis. In other examples, users 102 may have detailed information of a patient in various patient care dimensions. Nevertheless, the search can be initiated by receiving any information in any patient care dimensions. Predefined patient care dimensions (e.g., as designed based on a taxonomy of dimensions) that are available for users 102 to provide corresponding information may be designed as pull-down menu or any other suitable user interface elements and presented to the users 102. Based on the received information, the dimension information identifying unit 2202 extracts medical information and maps to its corresponding dimensions. For example, the dimension information identifying unit 2202 may inform the medical suggestion fetching unit 2204 that for the current search task, the doctor specialty dimension information is "cardiology," the patient age dimension information is "55 years old," and all other dimensions do not have corresponding information.

The medical suggestion fetching unit 2204 in this embodiment identifies medical suggestions based on to the received medical information of each dimension from the medical suggestion database 120 built and updated by the analytic engine 118. As each medical suggestion stored in the medical suggestion is associated with confidence scores with respect to the dimensions, the confidence scores of the identified medical suggestions are retrieved by the medical suggestion fetching unit 2204 as well. In the example shown in FIG. 20, if the dimension information identifying unit 2202 identifies that the only dimension information received with the search request is that the doctor specialty being cardiology, then the medical suggestion fetching unit 2204 may identify drugs under cardiology and obtain their confidence scores with respect to cardiology. In one example, the medical suggestions to be identified for each dimension may be limited to a predefined number, e.g., the top 100 entries ranked by their confidence scores. In another example, the identified medical suggestions may be limited by comparing their confidence scores with a threshold, e.g., only confidence scores above the threshold can be identified. In some embodiments, all the medical suggestions with confidence scores above zero may be identified.

In this embodiment, the medical suggestion fetching unit 2204 identifies separate set of medical suggestions and their confidence scores with respect to each dimension in which corresponding medical information is received in the search request. For example, based on the received information regarding doctor specialty, a first set of medical suggestions, e.g., drugs 1, 2, and 3, may be identified with their confidence scores with respect to the doctor specialty. In the same search request, if medical information in other dimensions is also available, for example, the patient's age, then another set of medical suggestions, e.g., drugs 2, 4, 5, and 6 may be identified as well with their confidence scores with respect to the patient's age.

The medical suggestion scoring unit 2206 in this embodiment automatically estimates an aggregated confidence score for each medical suggestion identified by the medical suggestion fetching unit 2204 based on each confidence score of the medical suggestion with respect to each dimension. Various scoring algorithms 2210 may be applied by the medical suggestion scoring unit 2206 in estimating the aggregated confidence score. In one example, a weighted summation algorithm is used for estimating the aggregated confidence score for a medical suggestion. That is, confidence scores with respect to different dimensions may be assigned with different weights and the weighted confidence scores with respect to each dimension are combined to generate the aggregated confidence score for the same medical suggestion. For example, assuming medical suggestion 1 is one of the medical suggestions identified for a search request with information in dimensions X, Y, and Z. The corresponding confidence scores associated with medical suggestion 1 with respect to dimensions X, Y, and Z are x, y, and z, respectively. Weights a, b, and c are predefined values for dimensions X, Y, and Z, respectively. Thus, in this example, the aggregated confidence scores for medical suggestion 1 in this search task may be estimated as ax+by+cz. The weights for each patient care dimension may be manually set based on knowledge and prior experience or automatically learned using any known machine learning approaches based on training data. In some embodiments, a simple summation algorithm may be applied. That is, no weights are applied to the confidence scores when they are combined.

The medical suggestion ranking unit 2208 in this embodiment ranks the medical suggestions based on their aggregated confidence scores. To limit the number of medical suggestions eventually returned to the users 102, in one example, only the top n ranked medical suggestions may be provided as search results. In another example, a threshold value of aggregated confidence score may be used to cut off medical suggestions with aggregated scores below the threshold. As the medical suggestions can be in different types, the medical suggestion ranking unit 2208 may rank and provide them separately in different types, e.g., a list of drugs, a list of diets, a list of physical therapies, etc. Or in some embodiments, all the medical suggestions regardless of their types may be ranked together based on their aggregated confidence scores and provided in a single list.

Figure 23:
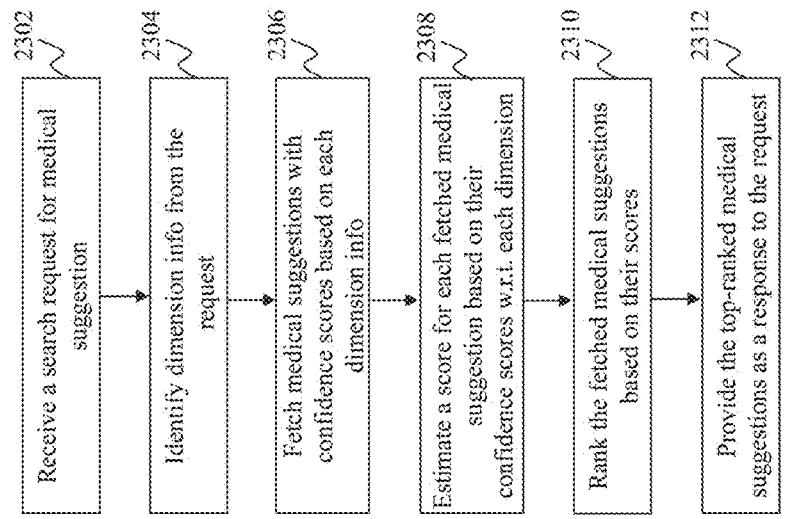
FIG. 23 is a flowchart of an exemplary process performed by the medical suggestion search engine, according to an embodiment of the present teaching.

FIG. 23 is a flowchart of an exemplary process performed by the medical suggestion search engine, according to an embodiment of the present teaching. Starting at 2302, a search request for medical suggestions is received from a user, e.g., a physician for his/her patient or a nurse for medication reconciliation. The request includes medical information in one or more patient care dimensions, such as the doctor specialty, the patient's age, gender, etc. At 2304, relevant patient care dimension information is identified. At 2306, based on the identified information in each dimension, matched medical suggestions are identified with their confidence scores with respect to the dimension. At 2308, an aggregate confidence score is estimated for each matched medical suggestion based on their confidence scores with respect to each dimension. For example, a weighted summation approach may be applied to combine the confidence scores with respect to each dimension. At 2310, the matched medical suggestions are ranked based on their aggregated confidence scores. At 2312, the top-ranked medical suggestions, either determined by the rankings or a cutoff threshold, are provided to the user as a response to the search request.

Figure 24:
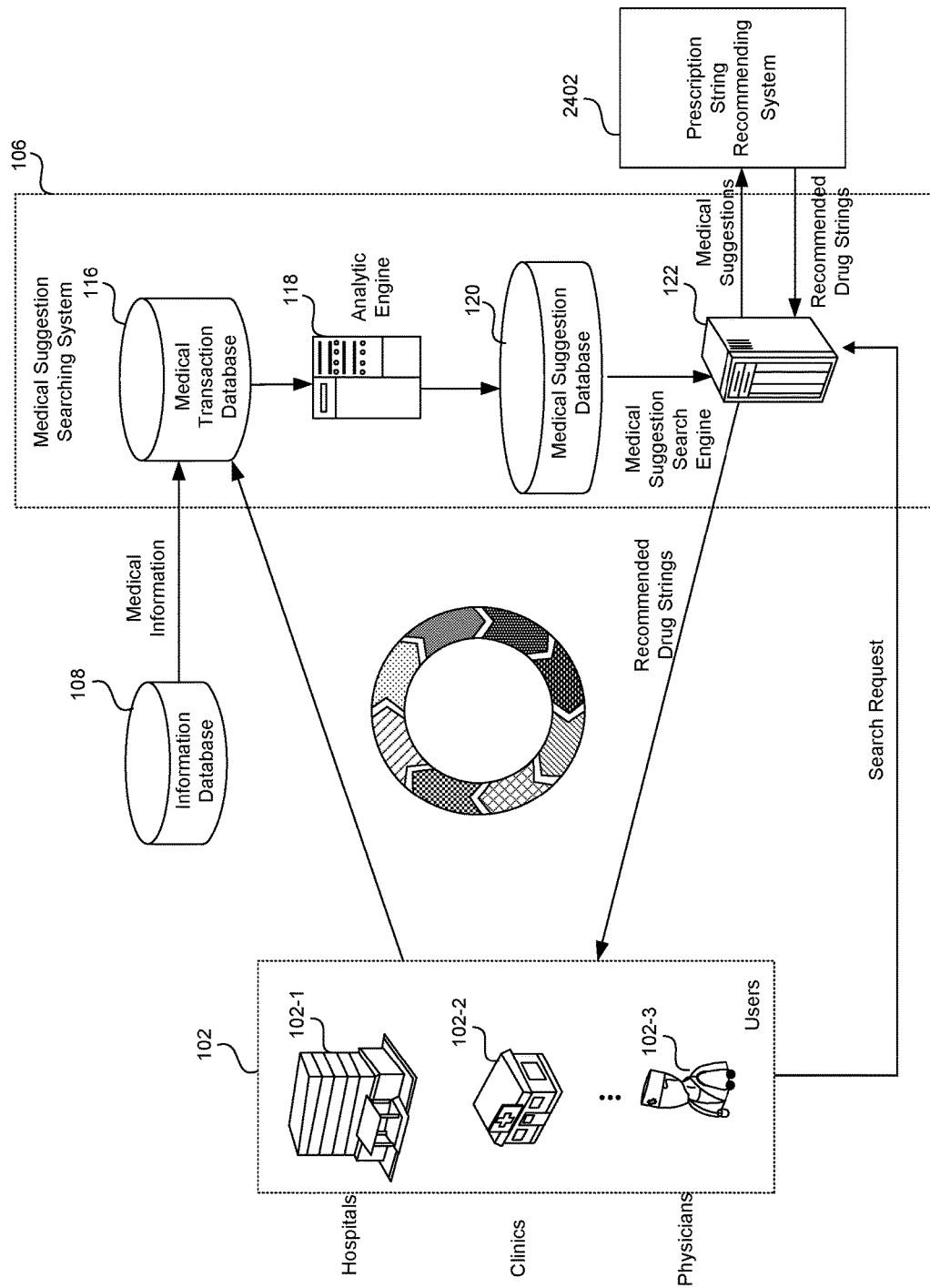
FIG. 24 illustrates an exemplary use case of the system for medical suggestion searching in prescription string recommendation, according to an embodiment of the present teaching.

FIG. 24 illustrates an exemplary use case of the system for medical suggestion searching in prescription string recommendation, according to an embodiment of the present teaching. In this embodiment, the medical suggestion searching system 106 is operatively coupled with a prescription string recommending system 2402 so that the combined system is capable of providing drug strings as medical suggestions to the users 102. As will be described later in detail, the prescription string recommending system 2402 can automatically return prescription strings based on the drugs identified by the medical suggestion searching system 106.

Figure 25:
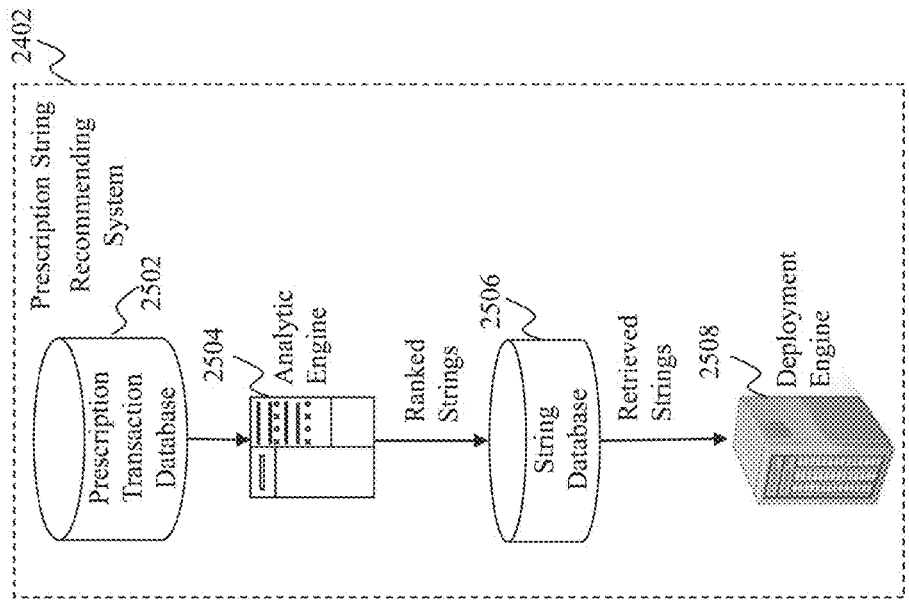
FIG. 25 illustrates an exemplary diagram of a prescription string recommending system, according to an embodiment of the present teaching.

FIG. 25 illustrates an exemplary diagram of a prescription string recommending system, according to an embodiment of the present teaching. The prescription string recommending system 2402 in this embodiment includes a prescription transaction database 2502, an analytic engine 2504, a string database 2506, and a deployment engine 2508.

The prescription string recommending system 2402 may provide different prescription strings to the medical suggestion searching system 106 or to the users 102 directly and collect feedbacks related to prescription transactions from the users 102. Prescription strings recommended by the prescription string recommending system 2402 are generated based on prescription transaction data in the prescription transaction database 2502. The prescription transaction database 2502 may store different types of information. For example, it may store information related to prescription transactions received from, e.g., the users 102. It may also store certain drug-related information, which may be retrieved from, e.g., the information database 108. It may also store information about prescriptions accumulated over time by the prescription string recommending system 2402. In some embodiments, prescription transactions from the users 102 and drug-related information from the information database 108 may be fed into the prescription transaction database 2502 within the prescription string recommending system 2402. This can be performed periodically according to a schedule, e.g. every night. The information stored in the prescription transaction database 2502 is retrieved by the analytic engine 2504 to generate ranked prescription strings to be stored in the string database 2506. At least some of the prescription strings stored in the string database 2506 can be retrieved by the deployment engine 2508 to form recommended prescription strings. The deployment engine 2508 sends the recommended prescription strings to the medical suggestion searching system 106 or the users 102 directly.

Figure 26:
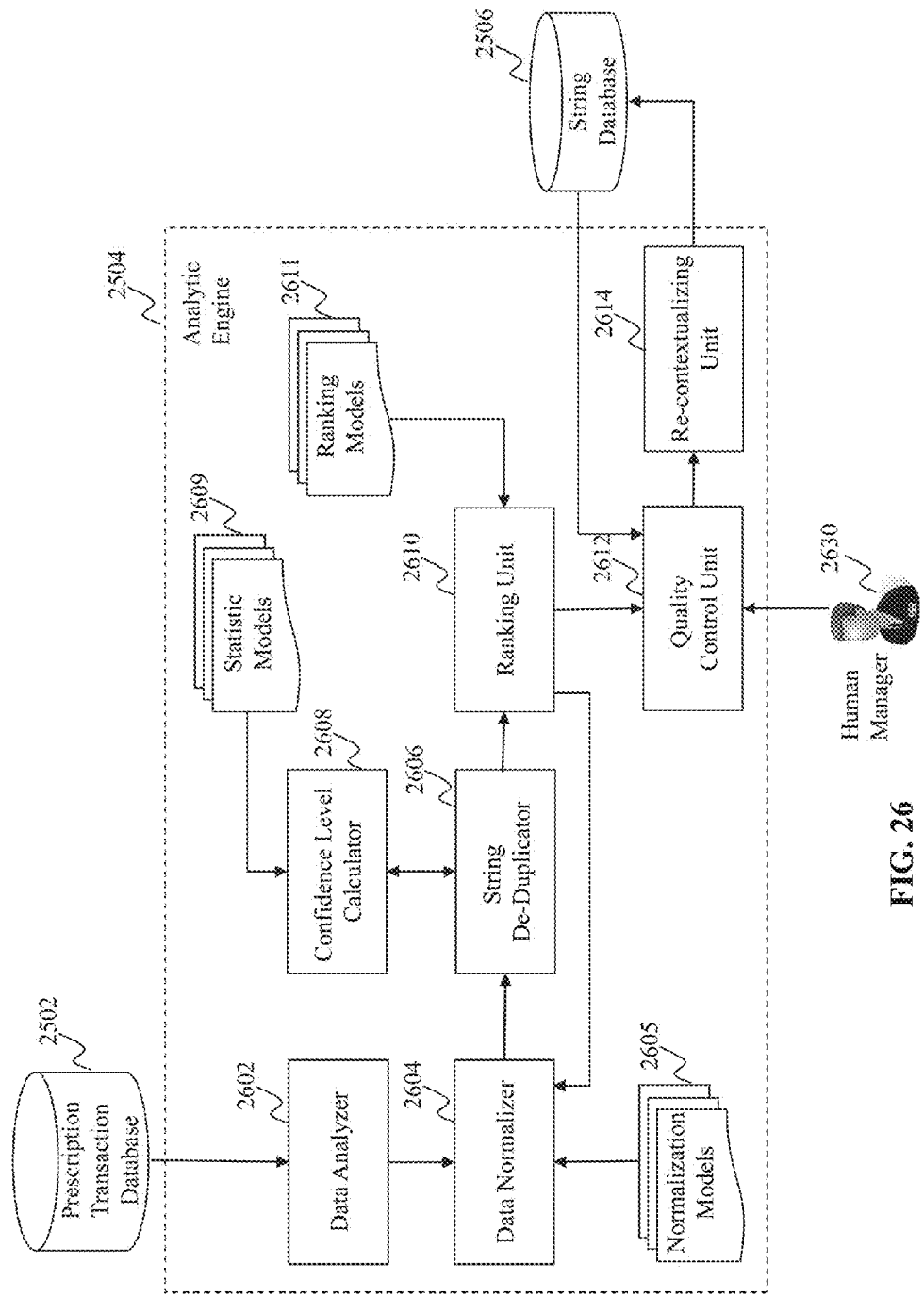
FIG. 26 illustrates an exemplary diagram of an analytic engine for prescription string generation, according to an embodiment of the present teaching.

FIG. 26 illustrates an exemplary diagram of an analytic engine 2504 for prescription string generation, according to an embodiment of the present teaching. The analytic engine 2504 is part of the prescription string recommending system 2402 (as shown in FIG. 25). In this exemplary embodiment, the analytic engine 2504 includes a data analyzer 2602, a data normalizer 2604, normalization models 2605, a string de-duplicator 2606, a confidence level calculator 2608, statistic models 2609, a ranking unit 2610, ranking models 2611, a quality control unit 2612, and a re-contextualizing unit 2614. The analytic engine 2504 in this example receives information about prescription transactions from the prescription transaction database 2502, generates ranked prescription strings and stores them into the string database 2506.

In this exemplary embodiment, the data analyzer 2602 may retrieve information from the prescription transaction database 2502. As discussed before, the information in the prescription transaction database 2502 may include data related to one or more medication drugs and/or information related to previous prescription transactions at one of the users 102. The data analyzer 2602 analyzes the retrieved information from the prescription transaction database 2502 to identify one or more candidate prescription strings. Each of the candidate prescription strings may be associated with a plurality of attributes. For example, the attributes can be represented by different fields in a prescription string, including action, dose, dose unit, route, timing, duration, quantity, dispense unit, refills, etc. The data analyzer 2602 sends the identified one or more candidate prescription strings to the data normalizer 2604 for processing.

In some embodiments, the data normalizer 2604 automatically processes each of the one or more candidate prescription strings based on some normalization models 2605. For example, based on some normalization model, the data normalizer 2604 may identify new entries from the candidate prescription strings and generate a fuzzy map to match new entries. Other normalization models may also be employed. For example, the data normalizer 2604 may identify drug strength and convert the drug strength to a normalized dose unit based on some conversion model. According to yet another normalization model, the data normalizer 2604 may obtain dose, frequency, and duration information from the candidate prescription strings and align quantity and duration of the prescription strings.

The normalization models 2605 may be pre-configured in the analytic engine 2504 for data normalization. Each configuration may also be dynamically adjusted, e.g. based on feedbacks from the users 102. The data normalizer 2604 may determine which data should be applied with what normalization scheme. For each prescription string to be normalized, appropriate normalization models are determined and applied accordingly. In some embodiments, the data normalizer 2604 may receive certain feedback from, e.g., the ranking unit 2610. The data normalizer 2604 may then carry out additional normalization processing based on the received feedback.

The string de-duplicator 2606 in this example removes duplicate strings from the candidate prescription strings. During the de-duplication process, the string de-duplicator 2606 may cooperate with the confidence level calculator 2608 to calculate a confidence level of a prescription string based on some given model, e.g., a statistic model. The statistic models 2609 may be selected or determined based on a variety of considerations, such as the source of each candidate prescription string, the feedbacks associated with each candidate prescription string, and the likelihood that each candidate prescription string will be recommended to a user. For example, a candidate prescription string generated based on data that was not converted may have a higher confidence level than another candidate prescription string generated based on data that was converted or back calculated. Confidence levels can also be higher when candidate prescription strings pass checks for factors of rationality from FDA. Based on feedbacks from the users 102 and/or predetermined configuration in the analytic engine 2504, the confidence level calculator 2608 may select a statistic model from the statistic models 2609 in the analytic engine 2504. Based on the statistic model, the confidence level calculator 2608 can calculate a confidence level associated with each candidate prescription string and send the confidence level to the string de-duplicator 2606. The string de-duplicator 2606 then sends the de-duplicated prescription strings with their confidence levels to the ranking unit 2610.

In some embodiments, the ranking unit 2610 may rank the prescription strings based on their confidence levels and a ranking model. The ranking model may be selected by the ranking unit 2610 from the ranking models 2611, e.g. based on feedbacks from users 102. For example, according to one ranking model, a prescription string that has been more frequently selected by users 102 than other prescription strings is ranked higher than other prescription strings. Alternatively, for a new candidate prescription string, if an existing prescription string similar to the candidate prescription string has been more frequently selected by users 102 than other candidate prescription strings, then the candidate prescription string should be ranked higher than other candidate prescription strings. Based on the ranking model, the ranking unit 2610 generates a list of ranked prescription strings.

In one embodiment, the ranking unit 2610 may send the ranked prescription strings back to the data normalizer 2604 to determine whether additional normalization is needed for the ranked prescription strings. In another embodiment, the ranking unit 2610 may send the ranked prescription strings back to the quality control unit 2612 for quality control.

The quality control unit 2612 may control quality of the prescription strings ranked by the ranking unit 2610 before they can be stored in the string database 2506. The quality control unit 2612 can automatically compare each prescription string with previously qualified prescription strings stored in the string database 2506. If a match can be found by the comparison, the matched prescription string is automatically qualified. Otherwise, a human review may be requested for the unmatched prescription string. As shown in FIG. 26, a human manager 2630 can perform a human review for each unmatched prescription string to determine whether the unmatched prescription string should be qualified. In one example, the human manager 2630 is an expert related to prescription strings and associated with the prescription string recommending system 2402. The quality control unit 2612 receives human reviews from the human manager 2630 and determines whether to qualify each unmatched prescription string based on the human review. The quality control unit 2612 then sends the qualified prescription strings to the re-contextualizing unit 2614.

The re-contextualizing unit 2614 in this example re-contextualizes the qualified prescription strings and saves the re-contextualized prescription strings into the string database 2506. The re-contextualization may include re-connecting each prescription string with a drug code, e.g. the NDC codes. The re-contextualization may also include generate a nomenclature map with the qualified prescription strings to be consistent with the stored prescription strings in the string database 2506.

Figure 27:
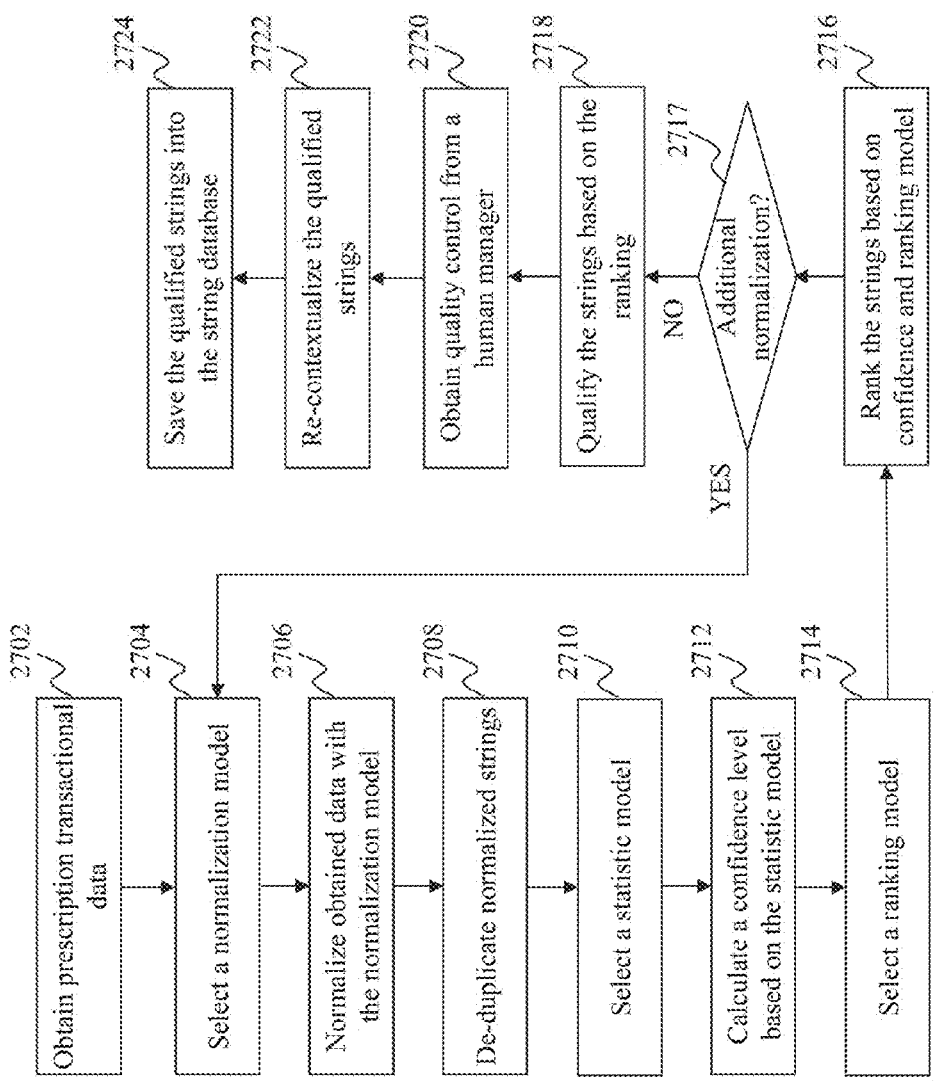
FIG. 27 is a flowchart of an exemplary process performed by an analytic engine for prescription string generation, according to an embodiment of the present teaching.

FIG. 27 is a flowchart of an exemplary process performed by an analytic engine, e.g. the analytic engine 2504 shown in FIG. 26, for prescription string generation, according to an embodiment of the present teaching. Starting at 2702, prescription transactional data are obtained. At 2704, a normalization model is selected. At 2706, the obtained data are normalized with the normalization model. At 2708, the normalized prescription strings are de-duplicated. At 2710, a statistic model is selected. At 2712, a confidence level is calculated for each prescription string based on the statistic model. At 2714, a ranking model is selected. At 2716, the prescription strings are ranked based on their confidence levels and the ranking model.

At 2717, it is checked whether additional normalization is needed. If so, the process goes back to 2704 to select a normalization model for additional normalization. Otherwise, the process goes to 2718, where the prescription strings are qualified based on their rankings and/or comparison between each prescription string and pre-qualified or pre-approved prescription strings. At 2720, quality control is obtained from a human manager, which may happen when some prescription strings cannot be matched with pre-qualified prescription strings based on the comparison at 2718. At 2722, the qualified prescription strings are re-contextualized. At 2724, the qualified and re-contextualized prescription strings are saved into the string database.

Figure 28:
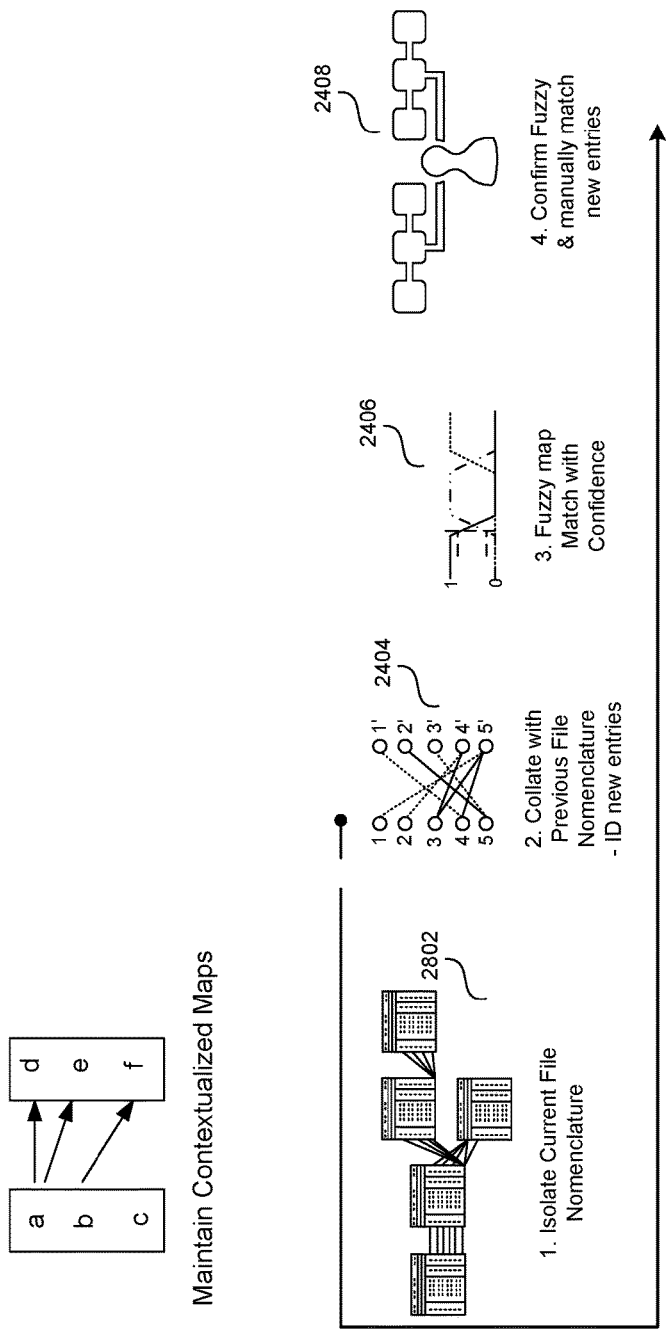
FIG. 28 illustrates an exemplary normalization model in an analytic engine, according to an embodiment of the present teaching.

FIG. 28 illustrates an exemplary normalization model in an analytic engine, according to an embodiment of the present teaching. As shown in FIG. 28, the normalization model in this example comprises a contextualized mapping model. According to the contextualized mapping model, a plurality of functions may be performed, e.g. by the data normalizer 2604. A first function 2802 is to isolate current file nomenclature from the candidate prescription strings. A second function 2804 is to collate the current file nomenclature with previous file nomenclature to identify new entries, i.e. the prescription strings that are not stored in the string database 2506. A third function 2806 is to generate a fuzzy map to characterize relations among the new entries and/or between the new entries and the existing prescription strings. Each relation may be associated with a confidence score representing a confidence about the relation. A fourth function 2808 is to confirm fuzzy relations generated by the third function 2806 and manually match the new entries based on the fuzzy map. The fourth function 708 may be performed together by the data normalizer 2604 and a human. In this example, the data normalizer 2604 may retrieve data from the string database 2506 directly.

Figure 29:
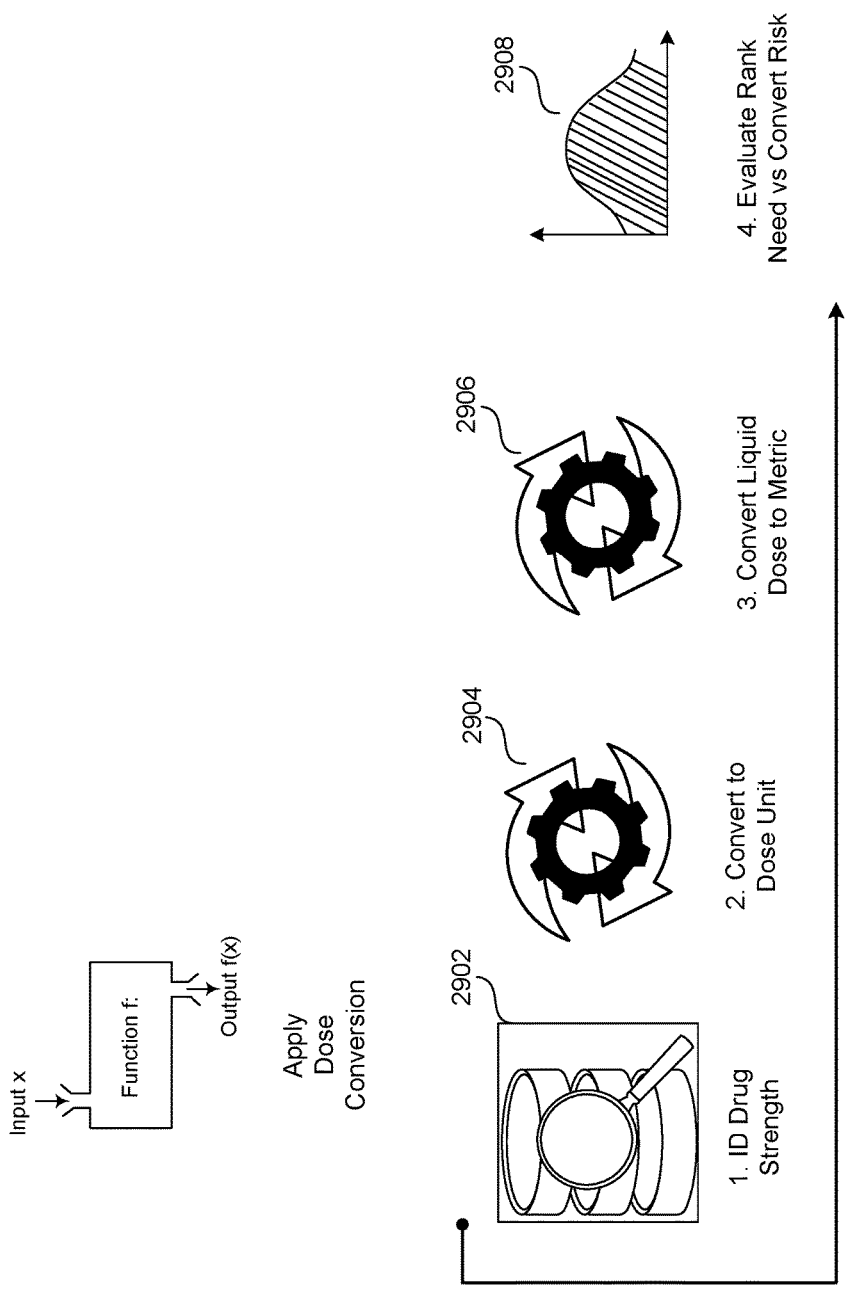
FIG. 29 illustrates another exemplary normalization model in an analytic engine, according to an embodiment of the present teaching.

FIG. 29 illustrates another exemplary normalization model in an analytic engine, according to an embodiment of the present teaching. As shown in FIG. 29, the normalization model in this example comprises a dose conversion model. According to the dose conversion model, a plurality of functions may be performed, e.g. by the data normalizer 2604. A first function 2902 is to identify drug strength. For example, the drug strength is 500 mg for a prescription string. A second function 2904 is to convert the drug dose when entered relative to strength to a normalized dose unit. For example, if the normalized dose unit for the medication is 500 mg, then the second function 2904 may convert the drug dose in to 1 Capsule. In this manner, whether the drug dose is input as 500 mg or 1 Capsule, the prescription string recommending system 2402 knows that this is the same drug dose.

A third function 2906 is to convert all liquid dose units into Metric. For example, a drug in a liquid form is commonly dispensed in teaspoon. In that situation, the third function 2906 will convert to a milliliter dose unit; so that the prescription string recommending system 2402 knows that a first prescription string for a medication with the teaspoon dose has the same drug dose as a second prescription string for the same medication with the milliliter dose unit. This information may be used for ranking and/or recommending the prescription strings. In that situation, the normalization model in this example can be referred to as a liquid dose conversion model. A fourth function 2908 is to evaluate rank need vs. the convert risk. There may be a tradeoff between the rank need and the convert risk. For example, when more and more prescription strings are converted to have a normalized dose unit, it is easier to rank the prescription strings but the risk of conversion error may increase as well. The fourth function 2908 may evaluate this tradeoff and find a good tradeoff point for the dose conversion.

Figure 30:
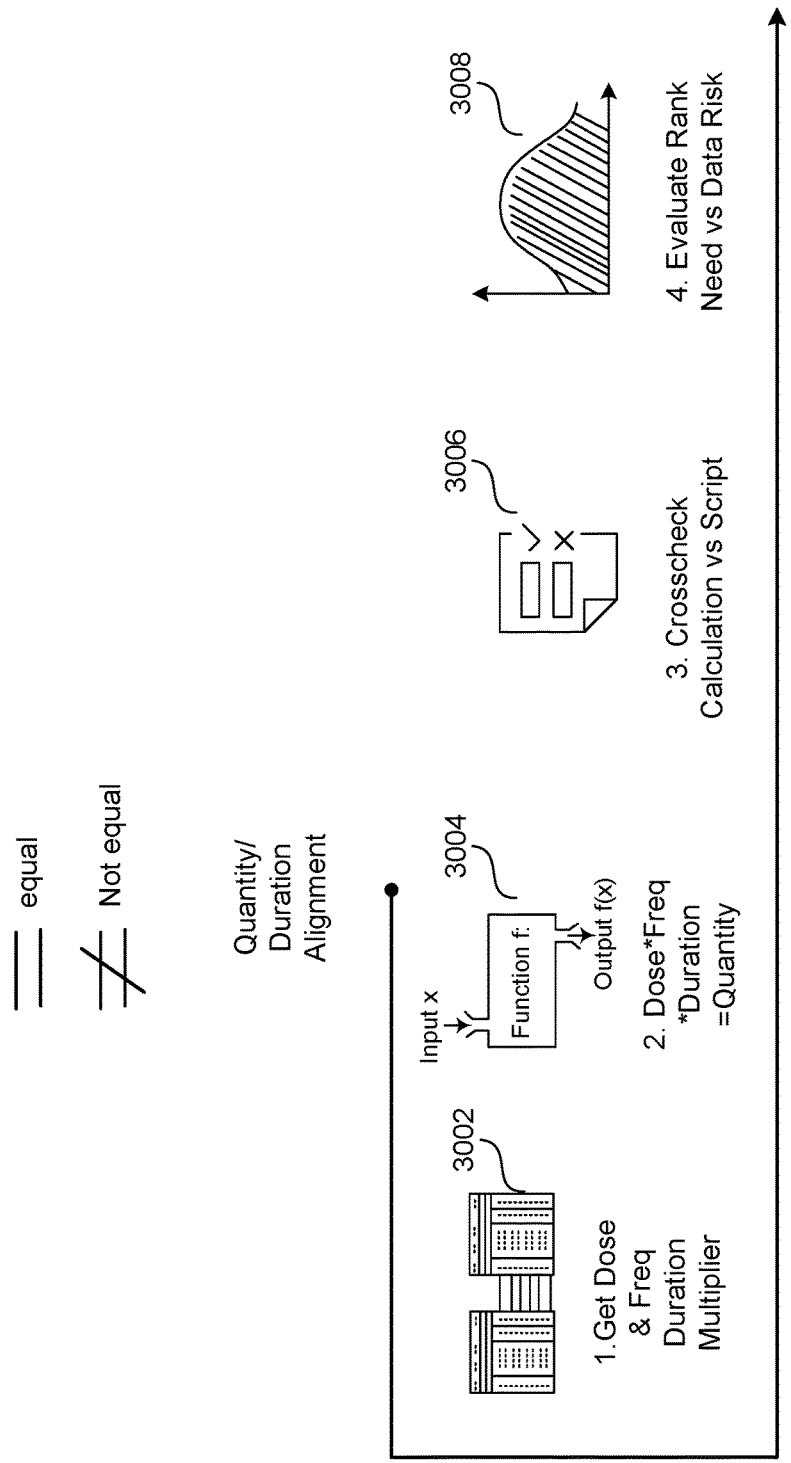
FIG. 30 illustrates yet another exemplary normalization model in an analytic engine, according to an embodiment of the present teaching.

FIG. 30 illustrates yet another exemplary normalization model in an analytic engine, according to an embodiment of the present teaching. As shown in FIG. 30, the normalization model in this example comprises a quantity/duration alignment model. According to the quantity/duration alignment model, a plurality of functions may be performed, e.g. by the data normalizer 2604. A first function 3002 is to get dose, frequency, and duration information from each prescription string. A second function 3004 is to calculate quantity for each prescription string by multiplying the dose, frequency and duration. A third function 3006 is to crosscheck the calculation of quantity vs. a script that may include the information about the quantity. In this manner, different prescription strings can be aligned by the calculated quantity and/or the duration. A fourth function 3008 is to evaluate rank need vs. data risk. There may be a tradeoff between the rank need and the data risk. For example, when more and more prescription strings are performed calculation of quantity following the second function 3004, it is easier to rank the prescription strings but the risk of data calculation error may increase as well. The fourth function 3008 may evaluate this tradeoff and find a good tradeoff point for the quantity/duration alignment.

Figure 31:
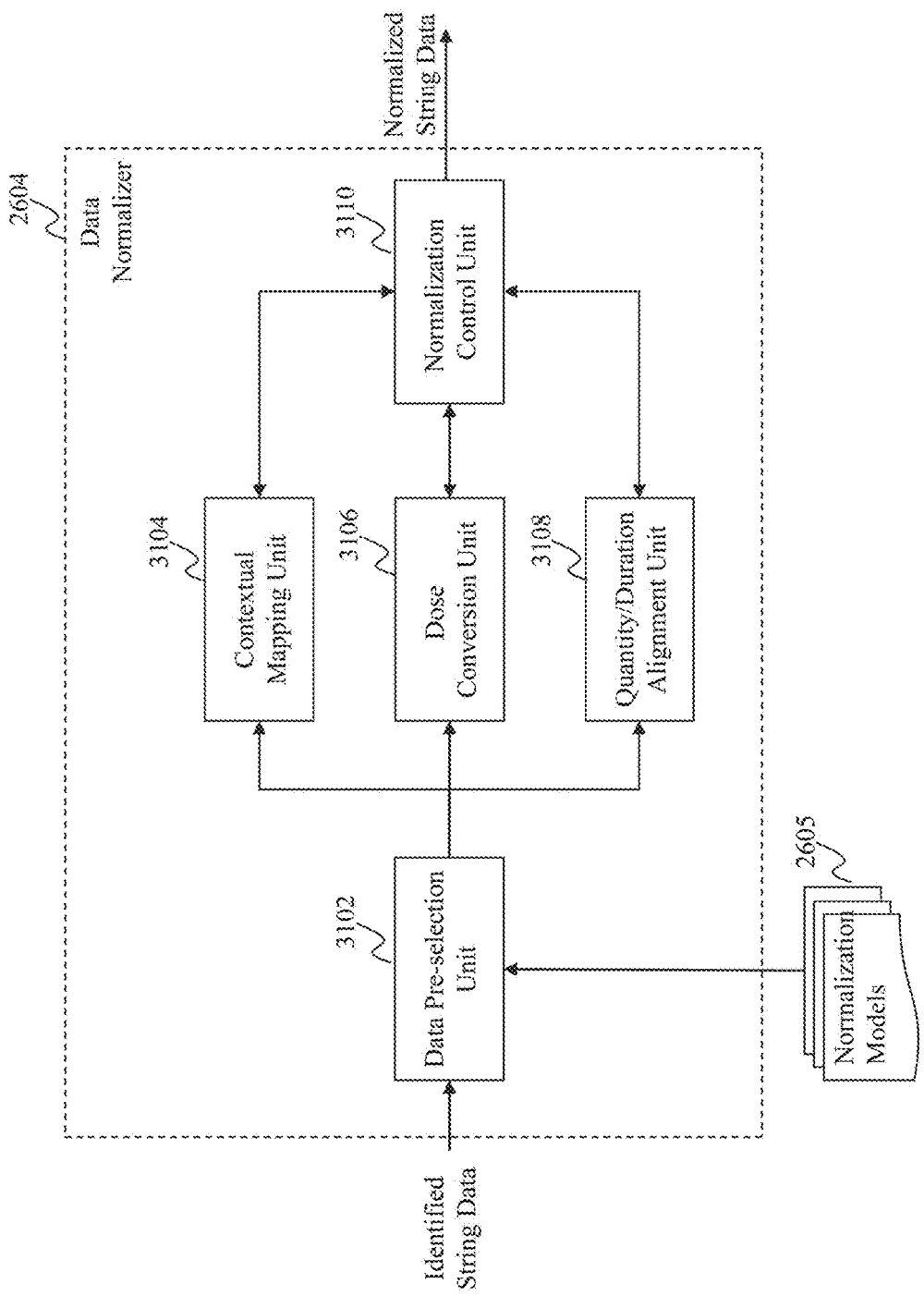
FIG. 31 illustrates an exemplary diagram of a data normalizer in an analytic engine, according to an embodiment of the present teaching.

FIG. 31 illustrates an exemplary diagram of the data normalizer 2604 in the analytic engine 2504 (in FIG. 26), according to an embodiment of the present teaching. The data normalizer 2604 in this example includes a data pre-selection unit 3102, a contextual mapping unit 3104, a dose conversion unit 3106, a quantity/duration alignment unit 3108, and a normalization control unit 3110.

The data pre-selection unit 3102 in this example receives identified prescription strings from the data analyzer 2602 and pre-select data for different normalizations based on normalization models 2605. The data pre-selection unit 3102 may select a normalization model and determine what data or which prescription strings should be normalized according to the selected normalization model. This may be performed for each normalization model in accordance with an embodiment. For each normalization model, the data pre-selection unit 3102 may send the pre-selected prescription strings data to one of the contextual mapping unit 3104, the dose conversion unit 3106, and the quantity/duration alignment unit 3108.

The contextual mapping unit 3104 in this example can perform the functions discussed before in FIG. 28. For example, the contextual mapping unit 3104 may identify new entries from the data and generate a fuzzy map to match the new entries. The dose conversion unit 3106 in this example can perform the functions discussed before in FIG. 29. For example, the dose conversion unit 3106 may identify drug strength from the data and convert the drug strength to a normalized dose unit. The quantity/duration alignment unit 3108 in this example can perform the functions discussed before in FIG. 30. For example, the quantity/duration alignment unit 3108 may obtain dose, frequency and duration information for each prescription string from the data and align the prescription strings with a calculated quantity based on the dose, frequency, and duration for each prescription string.

The normalization control unit 3110 in this example combines the normalized prescription strings data from the contextual mapping unit 3104, the dose conversion unit 3106, and the quantity/duration alignment unit 3108, and sends the combined data to the string de-duplicator 2606 for de-duplication. In one embodiment, the normalization control unit 3110 may help the contextual mapping unit 3104, the dose conversion unit 3106, and the quantity/duration alignment unit 3108 to exchange data to each other. For example, the contextual mapping unit 3104 may utilize converted dose unit from the dose conversion unit 3106 to identify whether a prescription string is a new entry or not.

Figure 32:
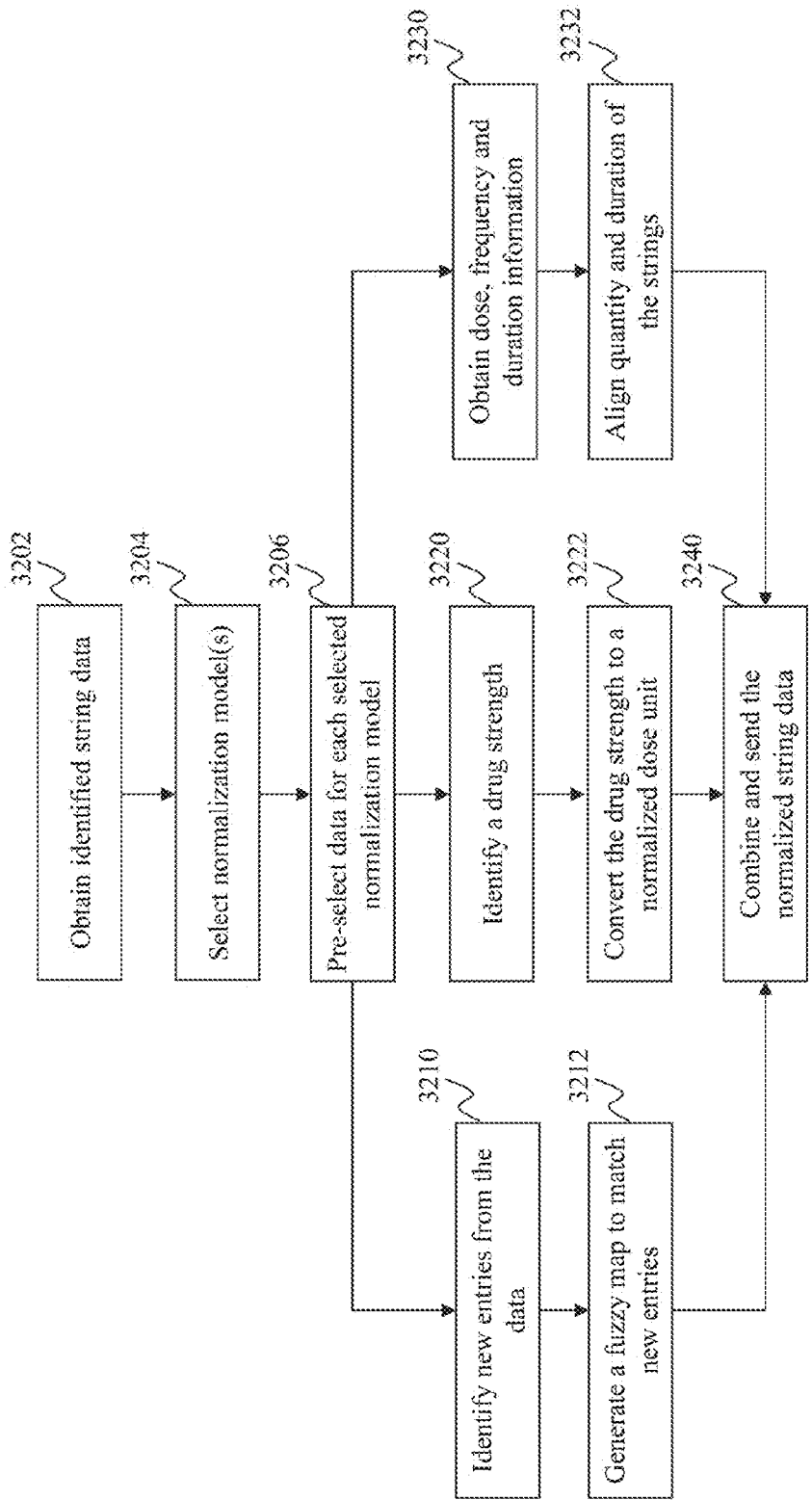
FIG. 32 is a flowchart of an exemplary process performed by a data normalizer, according to an embodiment of the present teaching.

FIG. 32 is a flowchart of an exemplary process performed by a data normalizer, e.g. the data normalizer 2604 in FIG. 31, according to an embodiment of the present teaching. Starting at 3202, identified prescription string data are obtained. At 3204, one or more normalization models are selected. At 3206, prescription string data are pre-selected for each of the selected normalization models. Depending on the selected normalization model, the process may go to 3210, 3220, and/or 3230 after 3206.

At 3210, new entries are identified from the prescription string data. At 3212, a fuzzy map is generated to match the new entries and the process goes to 3240. At 3220, drug strength is identified from the prescription string data. At 3222, the drug strength is converted to a normalized dose unit and the process goes to 3240. At 3230, information about dose, frequency, and duration is obtained. At 3232, quantity and duration of the prescription strings are utilized to align the prescription strings and the process goes to 3240. At 3240, the normalized prescription string data are combined and sent, e.g. to the string de-duplicator 2606.

Figure 33:
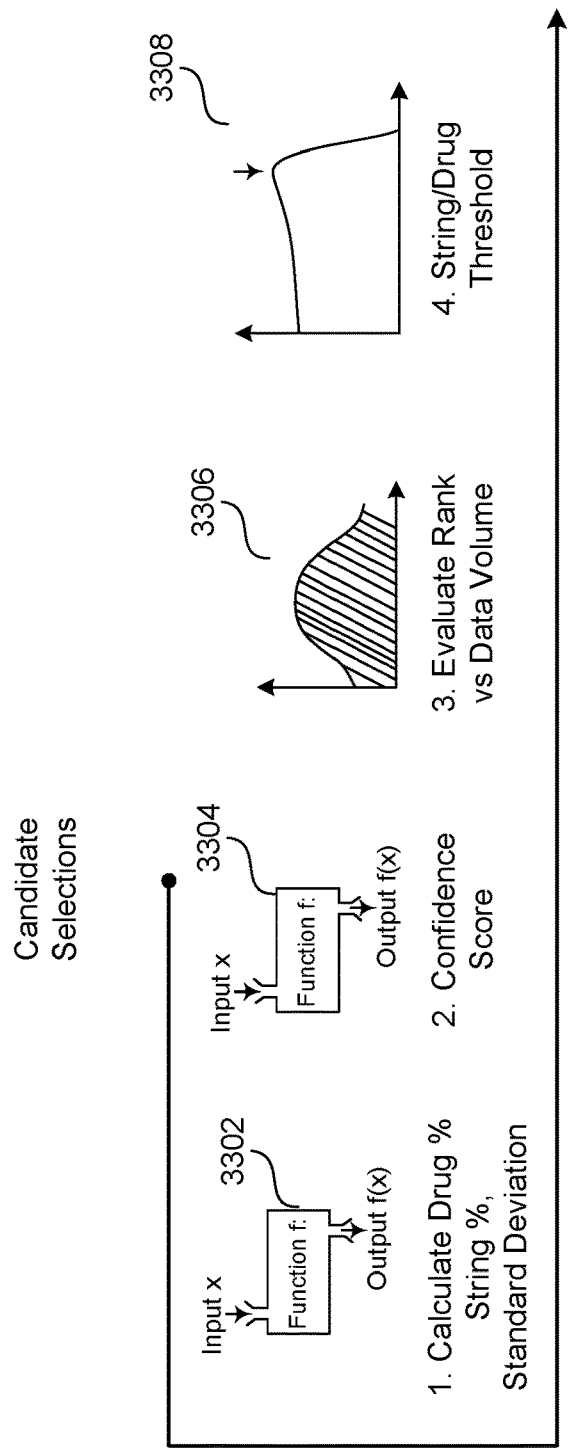
FIG. 33 illustrates an exemplary ranking model in an analytic engine, according to an embodiment of the present teaching.

FIG. 33 illustrates an exemplary ranking model in an analytic engine, according to an embodiment of the present teaching. As shown in FIG. 33, the ranking model in this example is utilized to rank and select candidate prescription strings. According to the ranking model, a plurality of functions may be performed, e.g. by the ranking unit 2610. A first function 3302 is to obtain or calculate drug and string related statistics, e.g. the percentage of drugs related to a given prescription string, the percentage of prescription strings related to a given drug, and standard deviation of number of prescription strings related to each drug, etc. A second function 3304 is to obtain a confidence score for each prescription string. In one embodiment, the confidence score can be identified from the de-duplicated string data. A third function 3306 is to evaluate rank vs. data volume. A rank for each prescription string can be determined based on its corresponding confidence score. But the candidate prescription strings are selected based on both their ranks and their frequency of which they are used by a user. The third function 3306 evaluates rank information of each prescription string vs. the data volume or frequency information associated with the prescription string. The fourth function 3308 is to determine a threshold based on the evaluation at the third function 3306. A candidate prescription string is selected as a prescription string to be qualified and stored in the string database 2506, if the prescription string has a high enough ranking and an associated frequency higher than the threshold.

Figure 34:
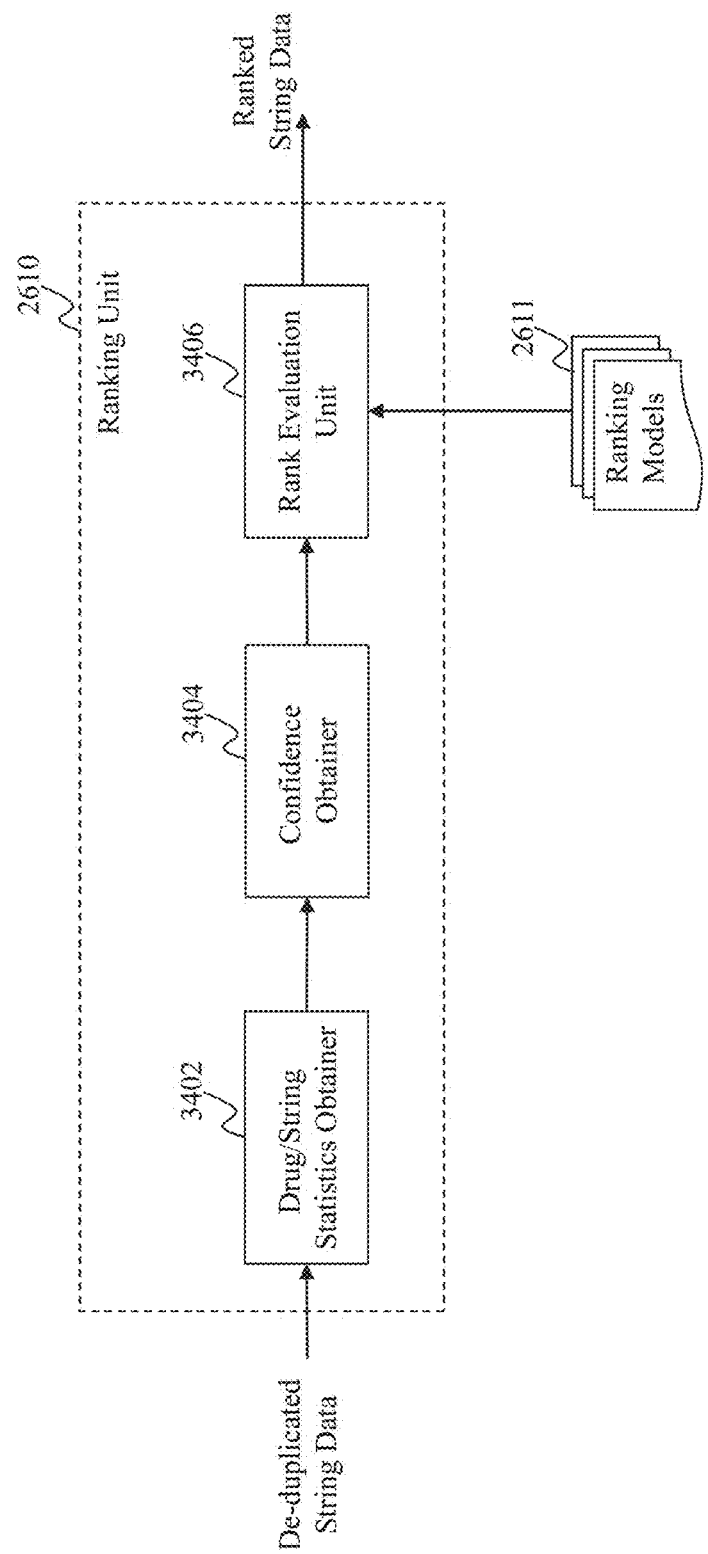
FIG. 34 illustrates an exemplary diagram of a ranking unit in an analytic engine, according to an embodiment of the present teaching.

FIG. 34 illustrates an exemplary diagram of a ranking unit 2610 in an analytic engine, e.g. the analytic engine 2504 in FIG. 26, according to an embodiment of the present teaching. The ranking unit 2610 in this example includes a drug/string statistics obtainer 3402, a confidence obtainer 3404, and a rank evaluation unit 3406.

The drug/string statistics obtainer 3402 in this example can perform the first function 3302 discussed before in FIG. 33. For example, the drug/string statistics obtainer 3402 may obtain drug and string related statistics. The confidence obtainer 3404 in this example can perform the second function 3304 discussed before in FIG. 33. For example, the confidence obtainer 3404 may obtain a confidence score for each drug and string. The rank evaluation unit 3406 in this example can perform the third function 3306 and the fourth function 3308 discussed before in FIG. 33. For example, the rank evaluation unit 3406 may evaluate rank vs. data volume to determine a string/drug threshold. The rank evaluation unit 3406 may also rank the prescription strings based on their confidence scores and a ranking model. The ranking model may specify the ranking be performed on the prescription strings passing the string/drug threshold, so that the rank evaluation unit 3406 sends the ranked prescription strings passing the threshold, e.g. to the quality control unit 2612 for quality control.

Figure 35:
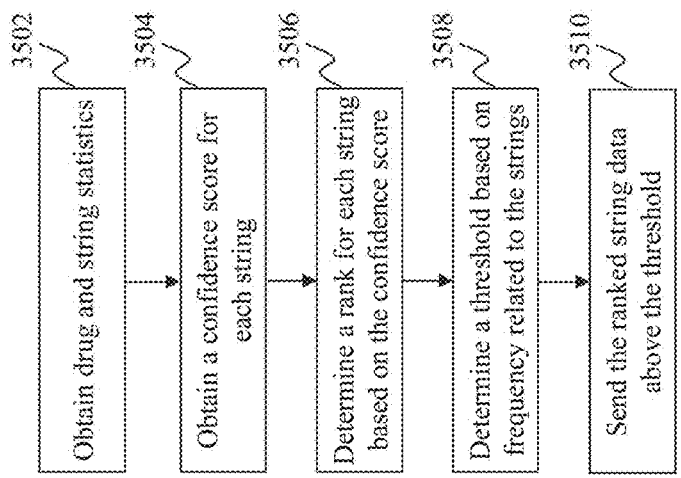
FIG. 35 is a flowchart of an exemplary process performed by a ranking unit, according to an embodiment of the present teaching.

FIG. 35 is a flowchart of an exemplary process performed by a ranking unit, e.g. the ranking unit 2610 in FIG. 34, according to an embodiment of the present teaching. Starting at 3502, drug and string statistics are obtained. At 3504, a confidence score is obtained for each prescription string. At 3506, a rank is determined for each prescription string based on the confidence score. At 3508, a threshold is determined based on frequency related to the prescription strings. At 3510, the ranked prescription strings that are above the threshold are sent, e.g. to the quality control unit 2612 for quality control.

Figure 36:
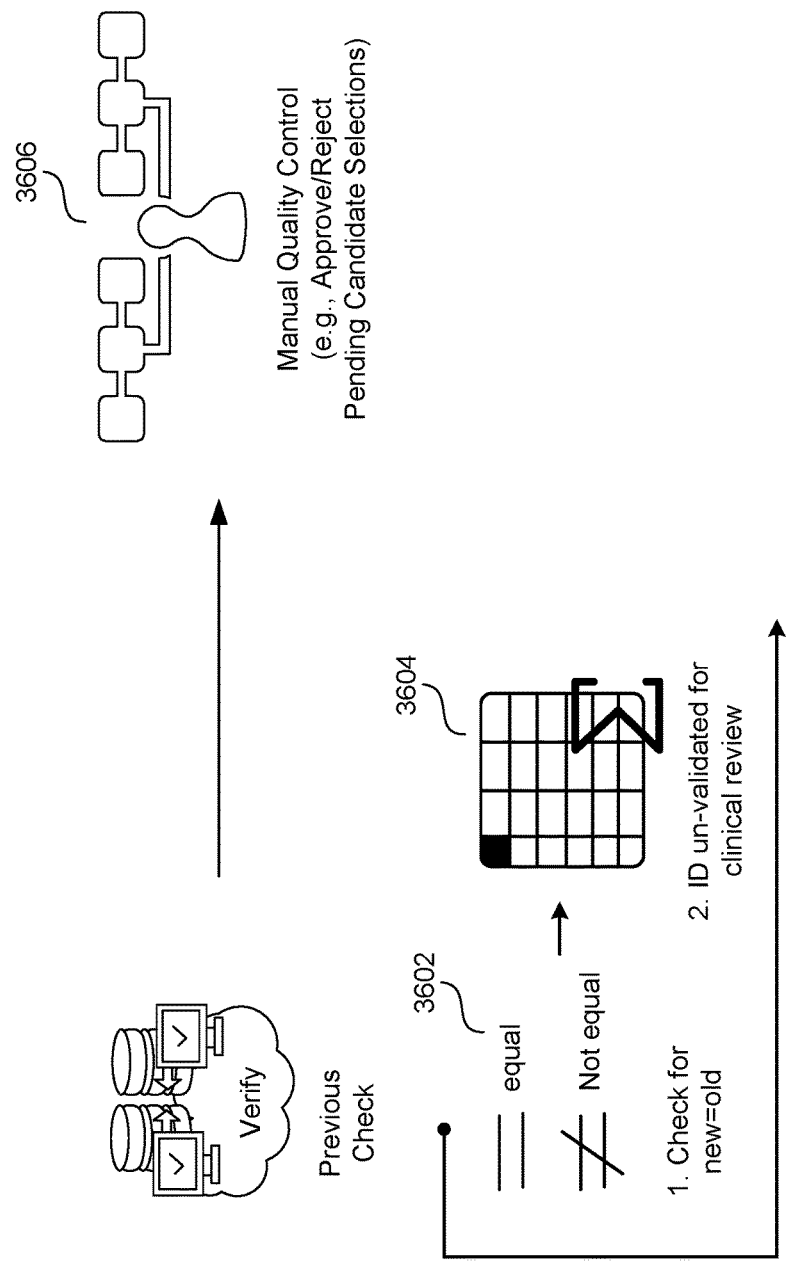
FIG. 36 illustrates exemplary functions performed by a quality control unit in an analytic engine, according to an embodiment of the present teaching.

FIG. 36 illustrates functions that can be performed by a quality control unit in an analytic engine, e.g. the analytic engine 2504 in FIG. 26, according to an embodiment of the present teaching. As shown in FIG. 36, a plurality of functions may be performed, e.g. by the quality control unit 2612. A first function 3602 is to check whether a new prescription string is equal to an existing pre-qualified prescription string or not. A second function 3604 is to identify the new prescription strings that do not match any existing pre-qualified prescription strings, i.e. the un-validated prescription strings. A third function 3606 is to obtain human review of the un-validated prescription strings to determine a manual qualification for each un-validated prescription string. While the first function 3602 and the second function 3604 can be performed automatically by the quality control unit 2612, the third function 3606 can be performed by the quality control unit 2612 with an involvement or interaction from a human, e.g. the human manager 2630 in FIG. 26.

Figure 37:
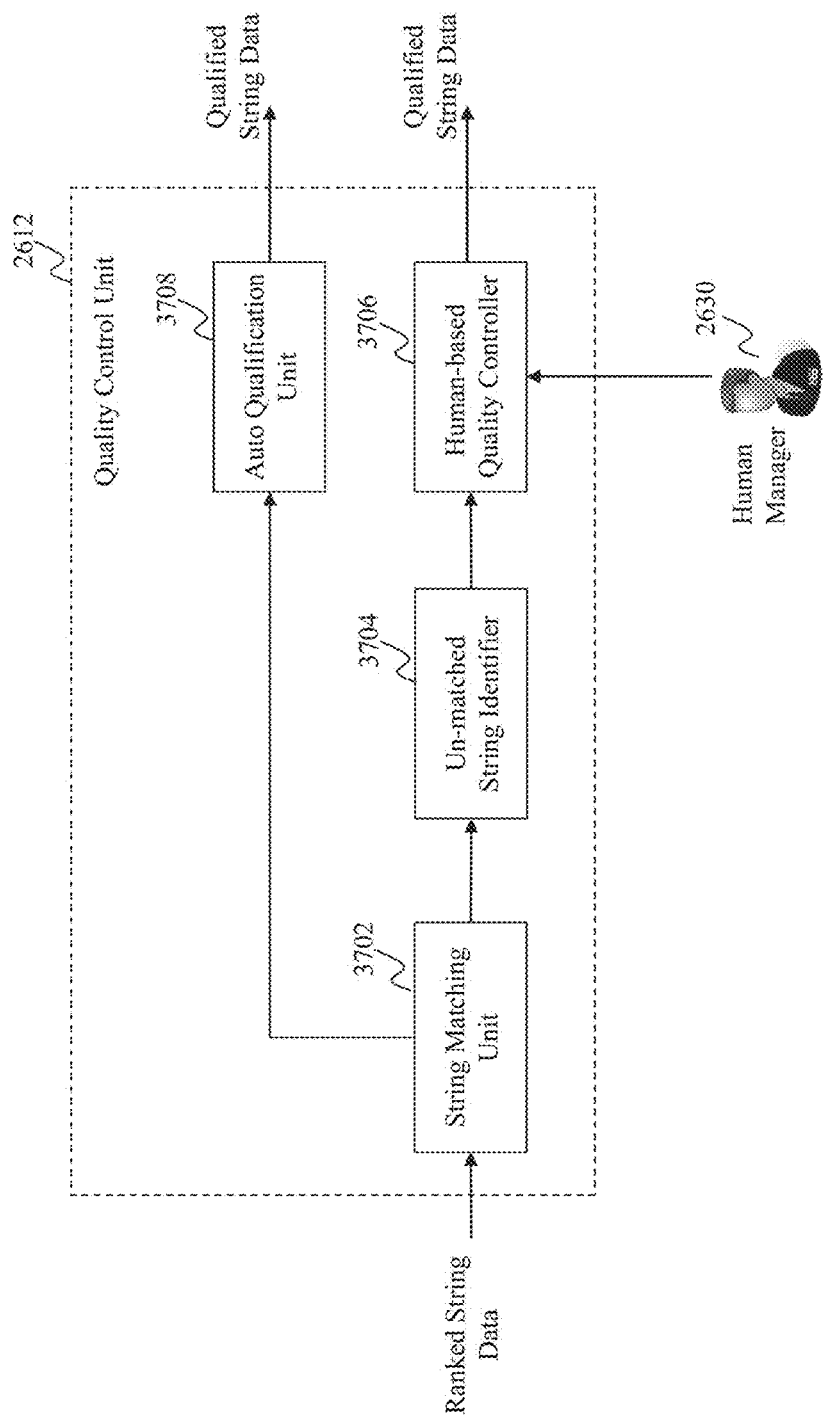
FIG. 37 illustrates an exemplary diagram of a quality control unit in an analytic engine, according to an embodiment of the present teaching.

FIG. 37 illustrates an exemplary diagram of a quality control unit 2612 in an analytic engine, e.g. the analytic engine 2504 in FIG. 26, according to an embodiment of the present teaching. The quality control unit 2612 in this example includes a string matching unit 3702, an un-matched string identifier 3704, a human-based quality controller 3706, and an auto qualification unit 3708.

The string matching unit 3702 in this example can perform the first function 3602 discussed before in FIG. 36. For example, the string matching unit 3702 may compare each ranked prescription string with pre-qualified prescription strings and sends each ranked prescription string to the un-matched string identifier 3704 or the auto qualification unit 3708 based on the comparison result. If a match is found for the prescription string based on the comparison result, the prescription string is sent to the auto qualification unit 3708 for auto qualification. Otherwise, if no match is found based on the comparison result, the prescription string is sent to the un-matched string identifier 3704. The un-matched string identifier 3704 in this example can perform the second function 3604 discussed before in FIG. 36. For example, the un-matched string identifier 3704 may identify the un-matched prescription strings, i.e. un-validated prescription strings, and may send them to the human-based quality controller 3706 for human review. The human-based quality controller 3706 in this example can perform the third function 3606 discussed before in FIG. 36. For example, the human-based quality controller 3706 may obtain human review from the human manager 2630 regarding each un-matched prescription string and qualify some un-matched prescription strings based on the human review. The auto qualification unit 3708 may automatically qualify prescription strings that are matched with pre-qualified prescription strings. The qualified string data from the auto qualification unit 3708 and the human-based quality controller 3706 are sent, e.g. to the re-contextualizing unit 2614.

Figure 38:
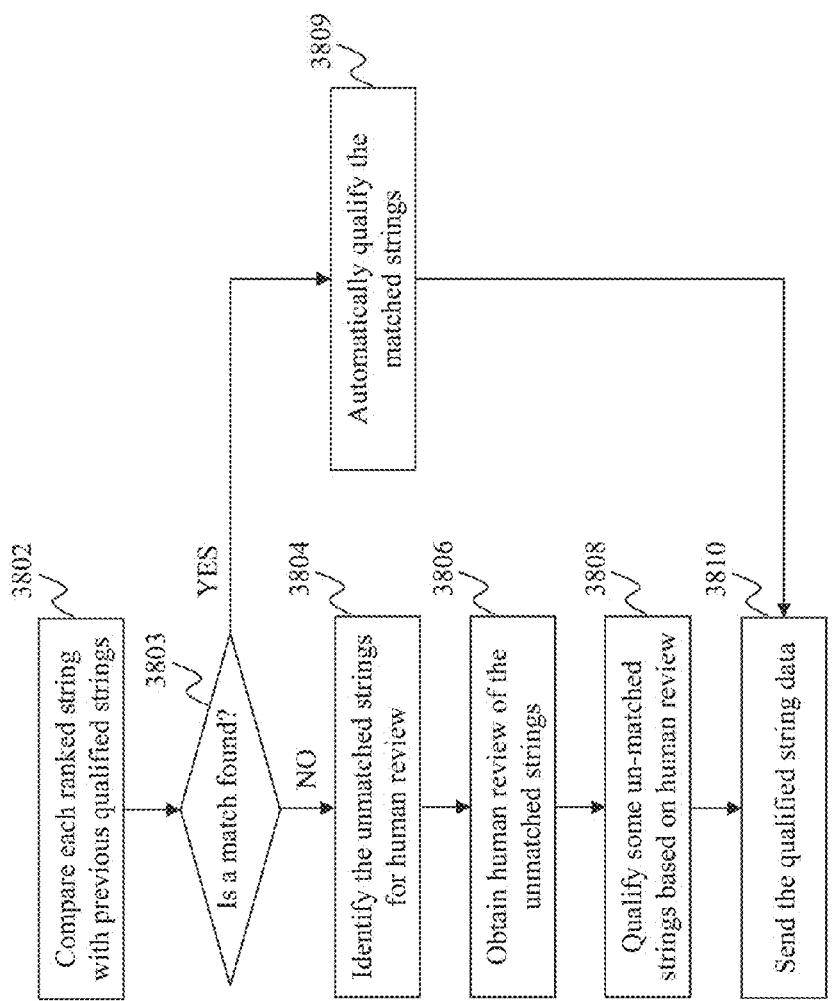
FIG. 38 is a flowchart of an exemplary process performed by a quality control unit, according to an embodiment of the present teaching.

FIG. 38 is a flowchart of an exemplary process performed by a quality control unit, e.g. the quality control unit 2612 in FIG. 37, according to an embodiment of the present teaching. Starting at 3802, each ranked prescription string is compared with previously qualified prescription strings. At 3803, it is determined whether a match is found for the prescription string based on the comparison result at 3802. If so, the process goes to 3809, where the matched prescription strings are automatically qualified and the process proceeds to 3810. Otherwise, if no match is found for the prescription string based on the comparison result at 3802, the process goes to 3804, where the un-matched prescription strings are identified for human review. At 3806, human review is obtained for each un-matched prescription string. At 3808, one or more un-matched prescription strings are qualified based on the human review. It can be understood that in one example all of the un-matched prescription strings are qualified based on the human review while in another example no un-matched prescription string is qualified based on the human review. At 3810, the qualified prescription strings are sent, e.g. to the re-contextualizing unit 2614 for re-contextualization.

Figure 39:
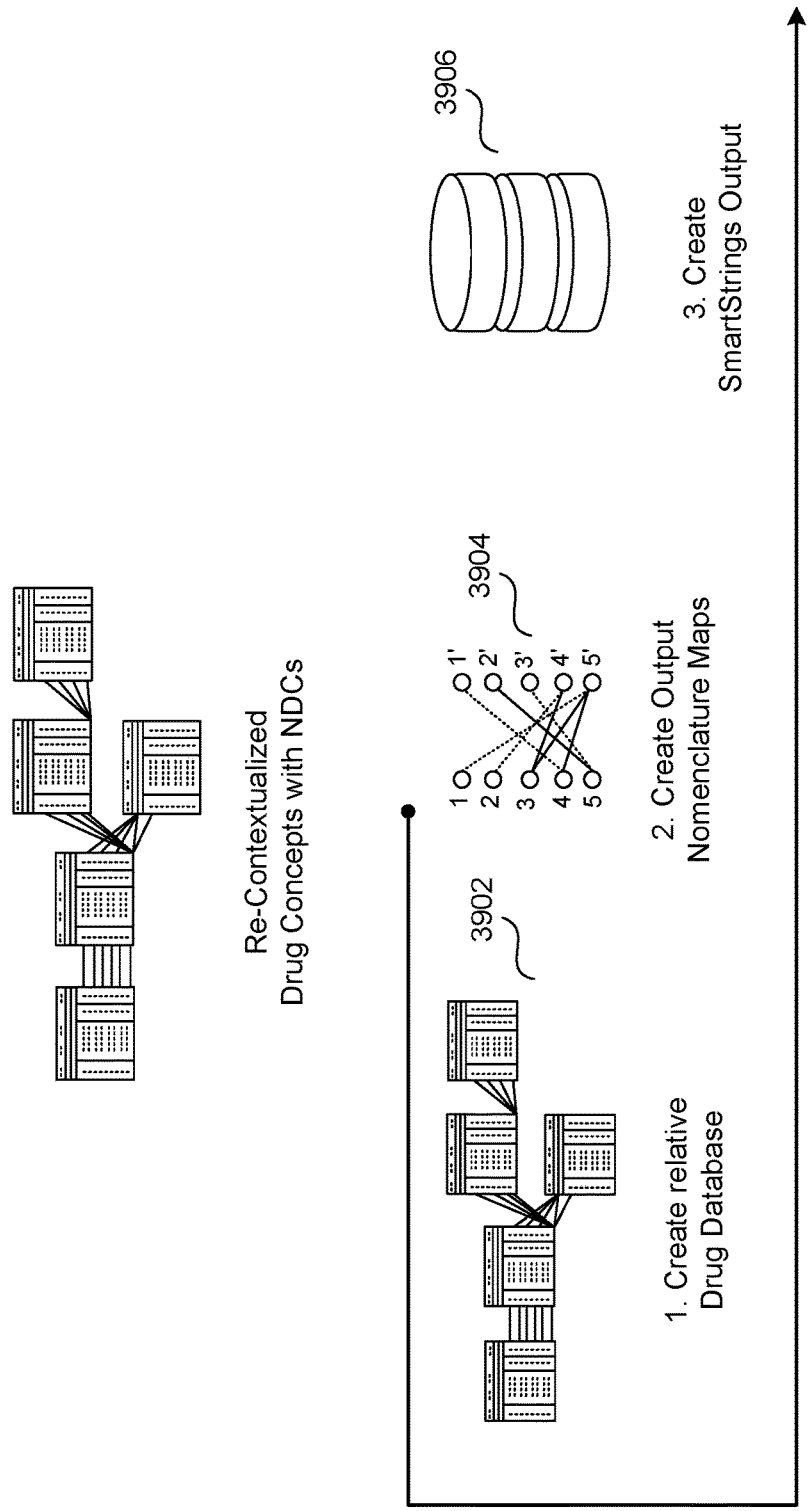
FIG. 39 illustrates exemplary functions performed by a re-contextualizing unit in an analytic engine, according to an embodiment of the present teaching.

FIG. 39 illustrates functions that can be performed by a re-contextualizing unit in an analytic engine, e.g. the analytic engine 2504 in FIG. 36, according to an embodiment of the present teaching. As shown in FIG. 39, a plurality of functions may be performed, e.g. by the re-contextualizing unit 2614. A first function 3902 is to create a relative drug database. The database comprises drug data in a hierarchical structure.

Figure 40:
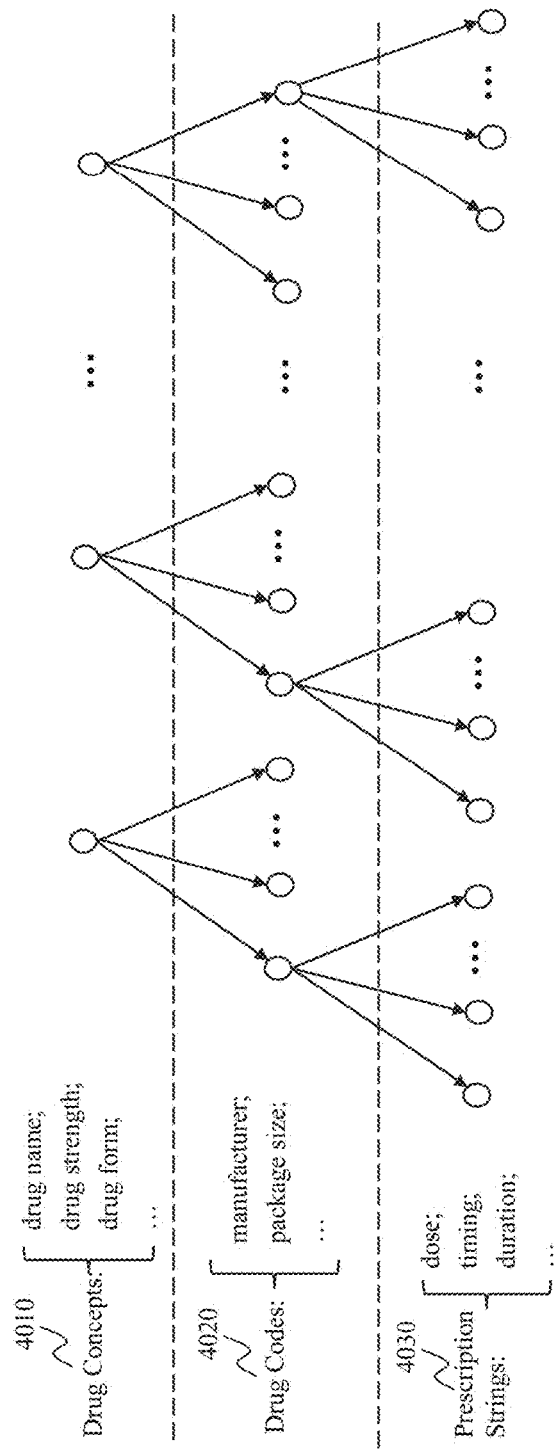
FIG. 40 illustrates re-contextualizing of drug data from a drug concept to a prescription string, according to an embodiment of the present teaching.

FIG. 40 illustrates an exemplary hierarchical structure for a drug from a drug concept to a prescription string, according to an embodiment of the present teaching. Each drug may have a plurality of drug concepts 4010. Each drug concept can specify some information related to the drug including but not limited to the drug name (e.g. Tylenol, Amoxicillin), drug strength (e.g. 500 mg, 300 mg), and drug form (e.g. tablet, capsule). Thus, a drug can be produced with different drug concepts, in accordance with different drug names, different drug strengths and/or different drug forms. Each drug concept can be associated with a plurality of drug codes 4020. Each drug code can specify additional information related to the drug concept including but not limited to the manufacturer (e.g. CVS, Walgreen) and package size (e.g. 50 tablets, 200 tablets). Thus, a drug or drug concept can be sold in the market with different drug codes, in accordance with different manufacturers and/or different package sizes. In practice, the drug code can be the NDC.

Each drug code can be associated with a plurality of prescription strings 4030. Each prescription string can specify additional information related to the drug code including but not limited to the dose (e.g. 1, 2), timing (e.g. once a day, twice a day), and duration (e.g. 5 days, 10 days). Thus, a drug with the same drug concept and the same drug code can be prescribed by a physician with different prescription strings, in accordance with different doses, different timings and/or different durations. In one embodiment, a prescription string is determined based on an associated drug code. For example, a physician may prescribe for a patient to take a drug for once a day if the drug is "sustained release" manufactured by CVS, while prescribing for the same patient to take the same drug twice a day if the drug is not sustained release manufactured by Walgreen. Thus, a complete prescription string may include information in each of the three levels: drug concept, drug code, and prescription string.

Back to FIG. 39, the candidate prescription strings were previously processed on the drug concept level. Thus, before the re-contextualization, the prescription strings were ranked and/or qualified without taking into consideration of the information about the manufacturers and package sizes. By creating relative drug database and re-contextualizing the prescription strings, each prescription string is associated with one or more drug codes, in addition to the associated drug concepts. In one embodiment, after the prescription strings are ranked on the drug level and drug concept level, the prescription strings can be further ranked and qualified on the drug code level (e.g. by different NDC codes) and/or on the prescription string level. In this manner, each drug concept is re-contextualized with different drug codes.

A second function 3904 in FIG. 39 is to generate a nomenclature map with the qualified prescription strings. A third function 3906 in FIG. 39 is to output the re-contextualized prescription strings to the string database 2506.

Figure 41:
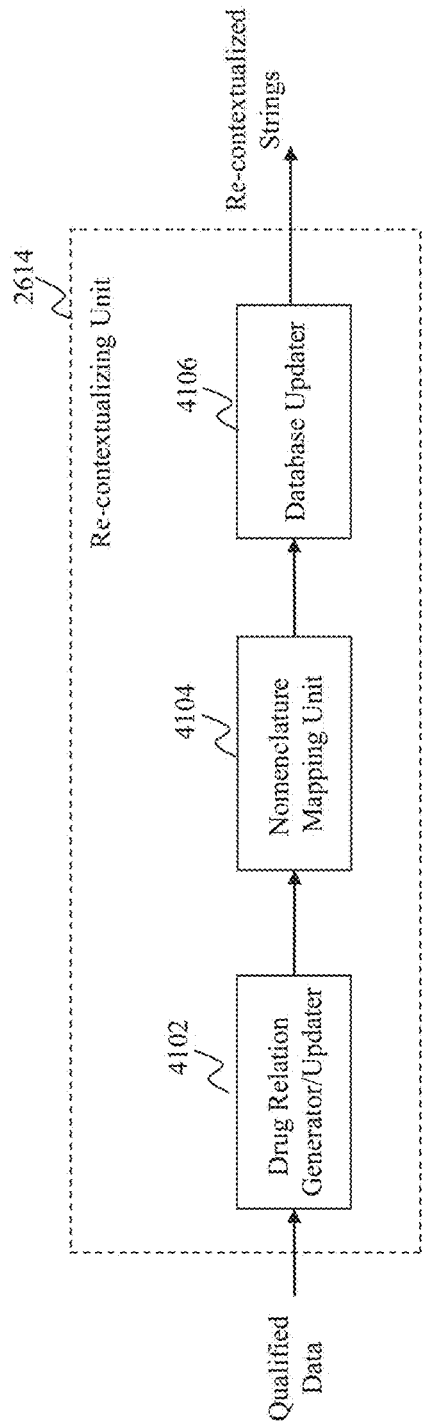
FIG. 41 illustrates an exemplary diagram of a re-contextualizing unit in an analytic engine, according to an embodiment of the present teaching.

FIG. 41 illustrates an exemplary diagram of a re-contextualizing unit 2614 in an analytic engine, e.g. the analytic engine 2504 in FIG. 26, according to an embodiment of the present teaching. The re-contextualizing unit 2614 in this example includes a drug relation generator/updater 4102, a nomenclature mapping unit 4104, and a database updater 4106.

The drug relation generator/updater 4102 in this example can perform the first function 3902 discussed before in FIG. 39. For example, the drug relation generator/updater 4102 may create or update drug/string relations by re-contextualizing each drug concept with one or more drug codes. The nomenclature mapping unit 4104 in this example can perform the second function 3904 discussed before in FIG. 39. For example, the nomenclature mapping unit 4104 may generate a nomenclature map with the qualified prescription strings. The database updater 4106 in this example can perform the third function 3906 discussed before in FIG. 39. For example, the database updater 4106 may update the string database 2506 by saving the re-contextualized strings into the string database 2506.

Figure 42:
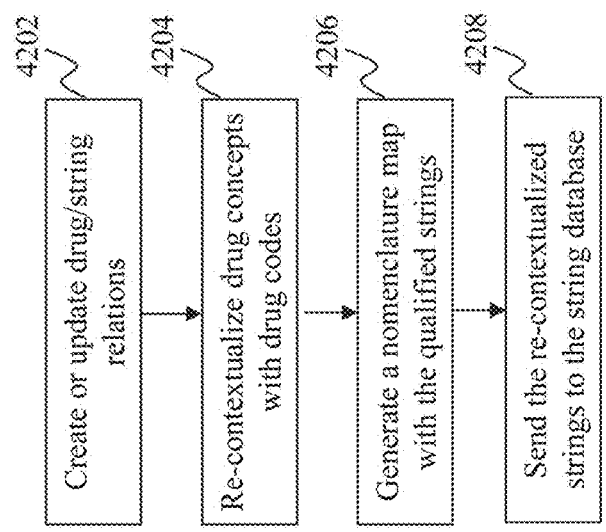
FIG. 42 is a flowchart of an exemplary process performed by a re-contextualizing unit, according to an embodiment of the present teaching.

FIG. 42 is a flowchart of an exemplary process performed by a re-contextualizing unit, e.g. the re-contextualizing unit 2614 in FIG. 41, according to an embodiment of the present teaching. Starting at 4202, drug/string relations are created or updated. At 4204, drug concepts are re-contextualized with drug codes, e.g. NDC codes. At 4206, a nomenclature map is generated with the qualified strings. At 4208, the re-contextualized prescription strings are sent to the string database 2506.

Figure 43:
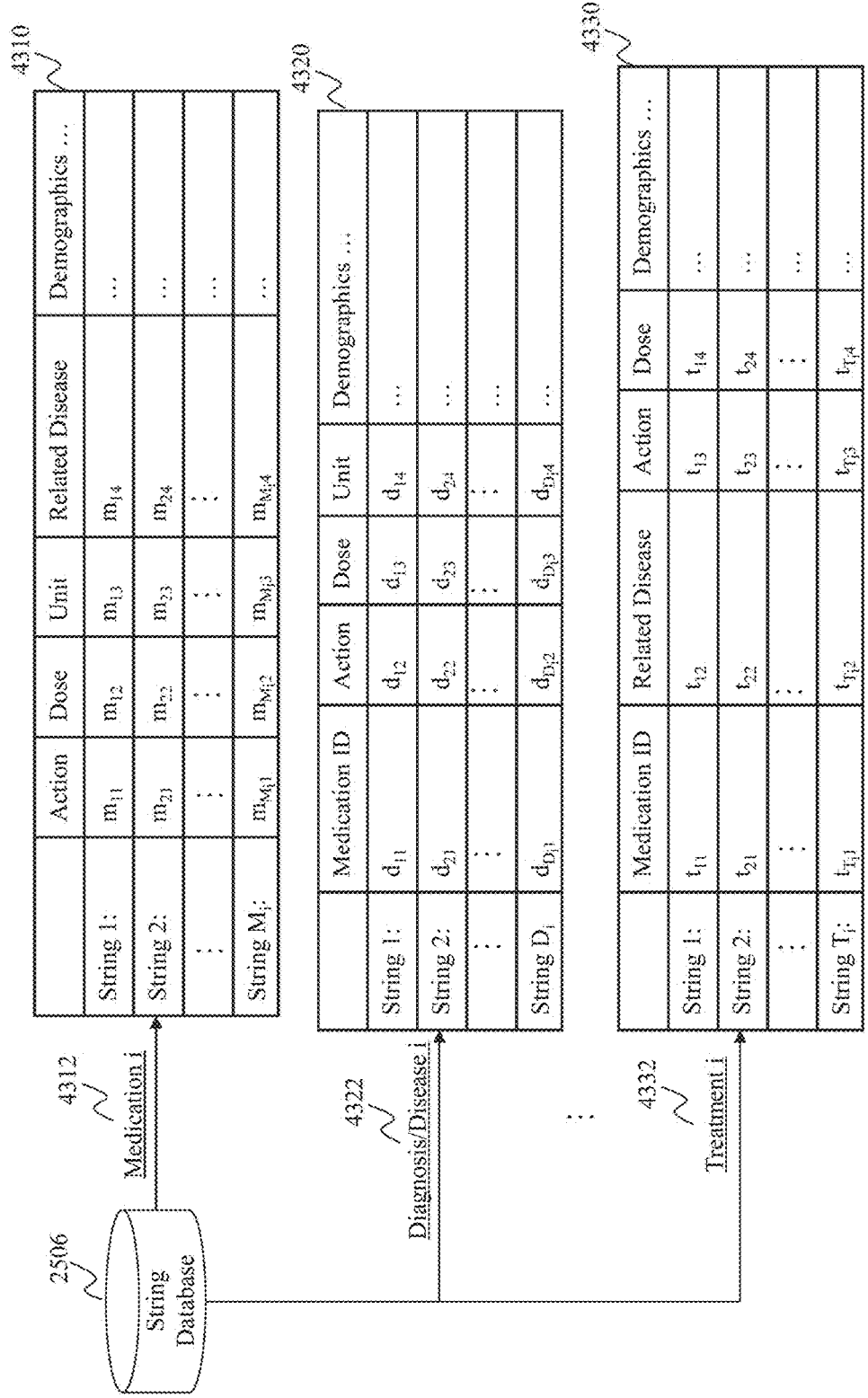
FIG. 43 illustrates different methods for retrieving prescription strings, according to various embodiments of the present teaching.

FIG. 43 illustrates different methods for retrieving prescription strings, according to various embodiments of the present teaching. As shown in FIG. 43, the prescription strings in the string database 2506 can be retrieved by a medication. For example, based on medication i 4312, $M_i$ prescription strings 4310 associated with the medication i are retrieved. Each of the $M_i$ prescription strings 4310 may include different fields/attributes including but not limited to action, dose, unit, related disease, and demographics. In one embodiment, the demographics include information like age and gender related to patients regarding whom the prescription strings were ordered. In another embodiment, the demographics do not include personal information of these patients.

As shown in FIG. 43, the prescription strings in the string database 2506 can also be retrieved by a diagnosis, a disease, and/or a treatment. For example, based on a diagnosis/disease i 4322, $D_i$ prescription strings 4320 associated with the diagnosis/disease i are retrieved. Each of the $D_i$ prescription strings 4320 may include different fields including but not limited to medication ID, action, dose, unit, and demographics. In another example, based on a treatment i 4332, $T_i$ prescription strings 4330 associated with the treatment i are retrieved. Each of the $T_i$ prescription strings 4330 may include different fields/attributes including but not limited to medication ID, action, dose, unit, related disease, and demographics.

FIG. 44 illustrates an exemplary prescription string 4400, according to an embodiment of the present teaching. As shown in FIG. 44, the prescription string 4400 includes eleven fields: drug ID 4402, action 4404, dose 4406, unit 4408, route 4410, timing 4412, duration 4414, dispense 4416, dispense quantity 4418, related disease 4420, and others 4422.

Figure 45:
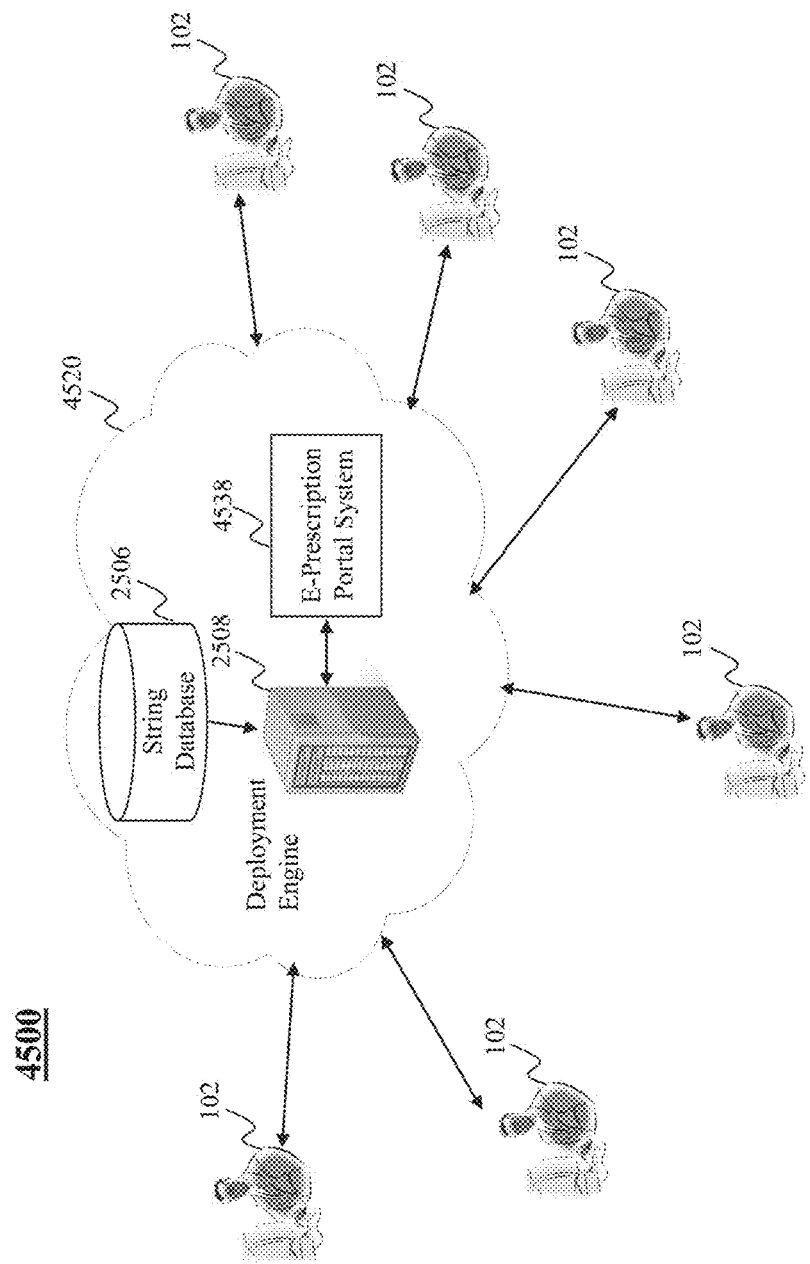
FIG. 45 illustrates a cloud-based network environment for a deployment engine, according to an embodiment of the present teaching.

FIG. 45 illustrates a cloud based network environment 4500 for a deployment engine 2508, according to an embodiment of the present teaching. The cloud based network environment 4500 includes a cloud 4520 and a plurality of users 102. The cloud 4520 includes the string database 2506, the deployment engine 2508, and an e-prescription portal system 4538. The e-prescription portal system 4538 may serve as a portal-based interface between the deployment engine 2508 and the users 102 connecting to the cloud 4520. In embodiment, the e-prescription portal system 4538 is located outside the deployment engine 2508 as shown in FIG. 45. In another embodiment, the e-prescription portal system 4538 is located inside the deployment engine 2508. In this cloud based network environment 4500, each user 102 may log in to the e-prescription portal system 4538 to request prescription strings from the deployment engine 2508.

Figure 46:
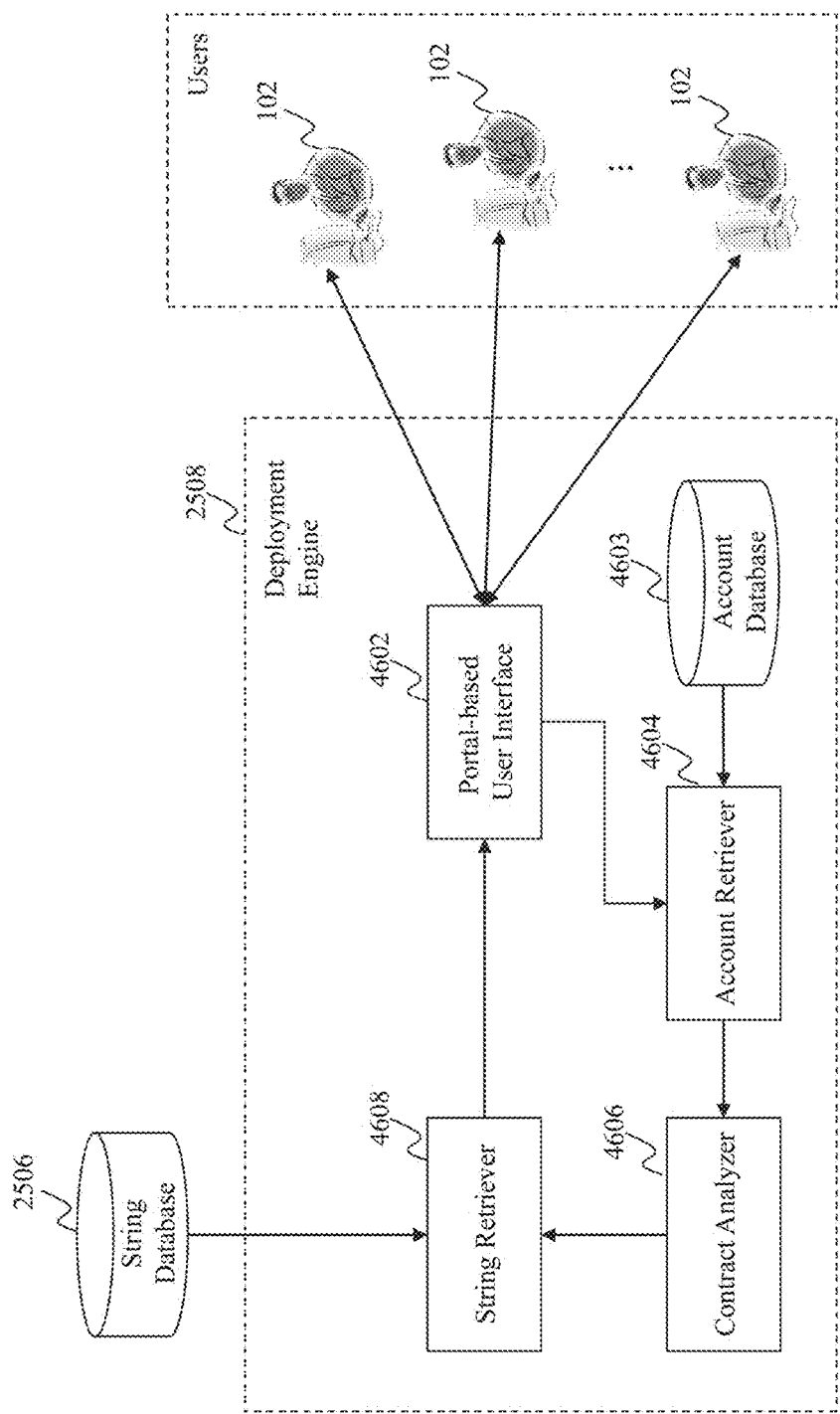
FIG. 46 illustrates an exemplary diagram of a deployment engine, according to an embodiment of the present teaching.

FIG. 46 illustrates an exemplary diagram of a deployment engine, e.g. the deployment engine 2508 in FIG. 45, according to an embodiment of the present teaching. The deployment engine 2508 in this example includes a portal-based user interface 4602, an account retriever 4604, an account database 4603, a contract analyzer 4606, and a string retriever 4608.

The portal-based user interface 4602 in this example receives log-in information and/or a request for prescription strings from one of the users 102. As discussed before, the users 102 may include hospitals, clinics, and/or physicians. The account retriever 4604 in this example retrieves an account from the account database 4603 based on the log-in information received by the portal-based user interface 4602. The account retriever 4604 may send information related to the account to the contract analyzer 4606. The contract analyzer 4606 in this example analyzes contract information associated with the account. For example, a contract associated with the account may specify whether the user associated with the account has authorization to access the prescription strings in the string database 2506, and if so, under what conditions.

The contract analyzer 4606 may determine whether the account information meets the required conditions to obtain the requested prescription strings based on the contract analysis. If so, the string retriever 4608 may retrieve the requested prescription strings from the string database 2506 and send the retrieved prescription strings to the user via the portal-based user interface 4602. Otherwise, the string retriever 4608 may send an error message to the user to indicate an error.

Figure 47:
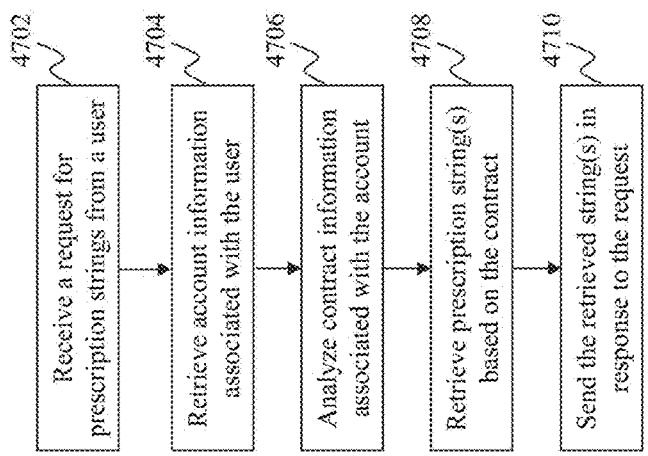
FIG. 47 is a flowchart of an exemplary process performed by a deployment engine, according to an embodiment of the present teaching.

FIG. 47 is a flowchart of an exemplary process performed by a deployment engine, e.g. the deployment engine 2508 in FIG. 2546 according to an embodiment of the present teaching. Starting at 4702, a request for prescription strings is received from a user. At 4704, account information associated with the user is retrieved. At 4706, contract information associated with the account is analyzed. At 4708, one or more prescription strings are retrieved based on the contract. At 4710, the one or more prescription strings are sent in response to the request.

Figure 48:
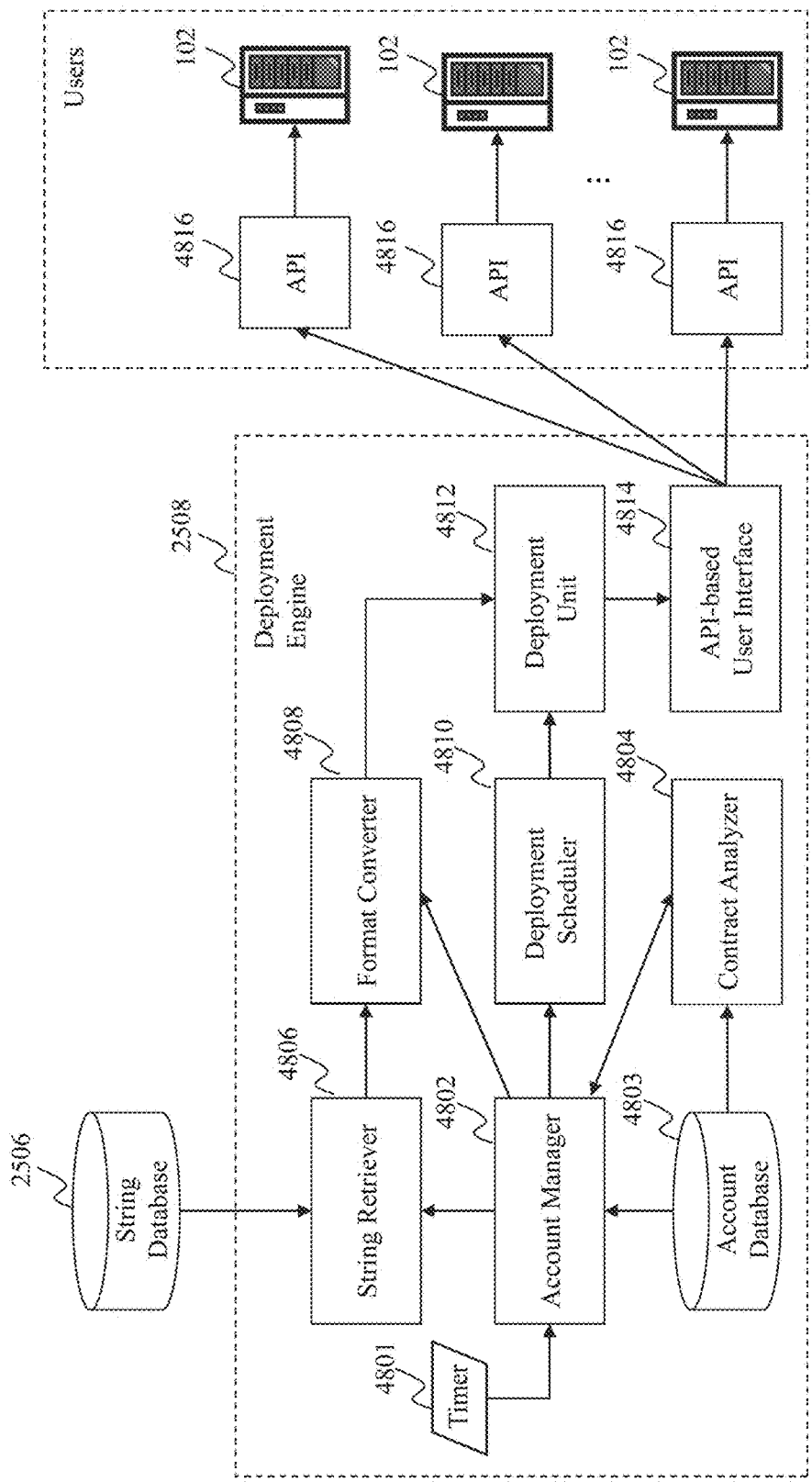
FIG. 48 illustrates another exemplary diagram of a deployment engine, according to another embodiment of the present teaching.

FIG. 48 illustrates another exemplary diagram of a deployment engine, e.g. the deployment engine 2508 in FIG. 25, according to another embodiment of the present teaching. The deployment engine 2508 in this example includes a timer 4801, an account manager 4802, an account database 4803, a contract analyzer 4804, a string retriever 4806, a format converter 4808, a deployment scheduler 4810, a deployment unit 4812, and an API-based user interface 4814.

The account manager 4802 in this example can determine whether it is time to manage an account for deploying prescription strings to a user 102 based on information from the timer 4801. If so, the account manager 4802 may retrieve account information related to the user from the account database 4803 and trigger the contract analyzer 4804 to analyze a contract associated with the account. The contract analyzer 4804 in this example analyzes contract information associated with the account to determine whether the user associated with the account has met the conditions required to obtain the prescription strings from the string database 2506. If so, the account manager 4802 sends information to the string retriever 4806, the format converter 4808 and the deployment scheduler 4810.

The string retriever 4806 in this example retrieves prescription strings from the string database 2506 based on information received from the account manager 4802 and sends the prescription strings to the format converter 4808. The format converter 4808 receives information from the account manager 4802 to determine a format that can be compatible with application programming interface (API) 4816 of the user 102. The format converter 4808 then converts the prescription strings from the string retriever 4806 to the format. The deployment scheduler 4810 in this example determines a schedule for deploying the prescription strings based on the information from the account manager 4802. For example, when deployment for multiple accounts is due within a same time period, deployment for an account associated with a higher priority based on contract information may be scheduled earlier than deployment for another account associated with a lower priority based on contract information.

The deployment unit 4812 in this example receives schedule information for each account and retrieved prescription strings for each account with corresponding formats. The deployment unit 4812 then sends the prescription strings to the users according to the schedule information via the API-based user interface 4814.

Figure 49:
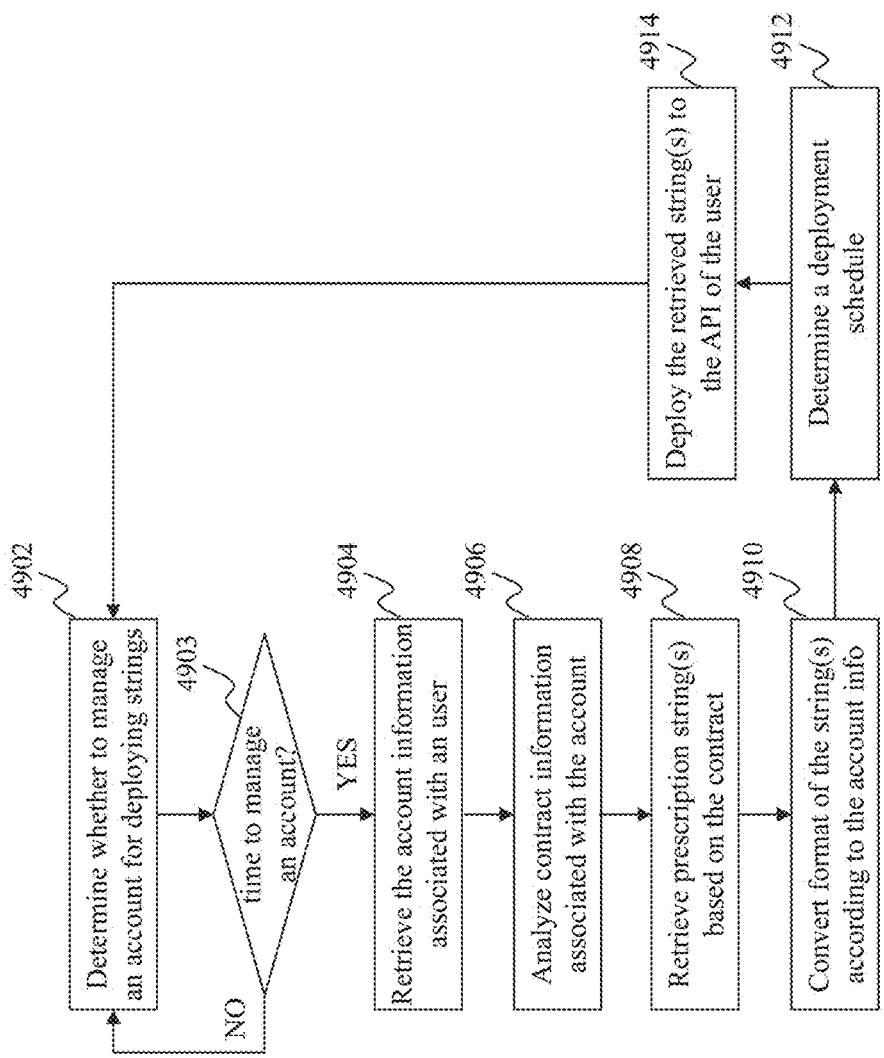
FIG. 49 is a flowchart of another exemplary process performed by a deployment engine, according to another embodiment of the present teaching.

FIG. 49 is a flowchart of another exemplary process performed by a deployment engine, e.g. the deployment engine 2508 in FIG. 48, according to an embodiment of the present teaching. Starting at 4902, it is determined whether it is time to manage an account for deploying strings to a user. At 4903, the result of determination of 4902 is checked. If it is not yet time to manage an account, the process goes back to 4902 to continue monitoring the time and account information. Otherwise, if it is time to manage an account associated with a user, the process goes to 4904, where the account information associated with the user is retrieved. At 4906, contract information associated with the account is analyzed. At 4908, one or more prescription strings are retrieved based on the contract.

At 4910, the one or more prescription strings are converted to a format that is compatible with API of the user, according to the account information. At 4912, a deployment schedule is determined based on the account information and other accounts having deployment tasks in the same time period. At 4914, the retrieved prescription strings are deployed to the API of the user, and the process goes back to 4902 to manage other accounts.

Figure 50:
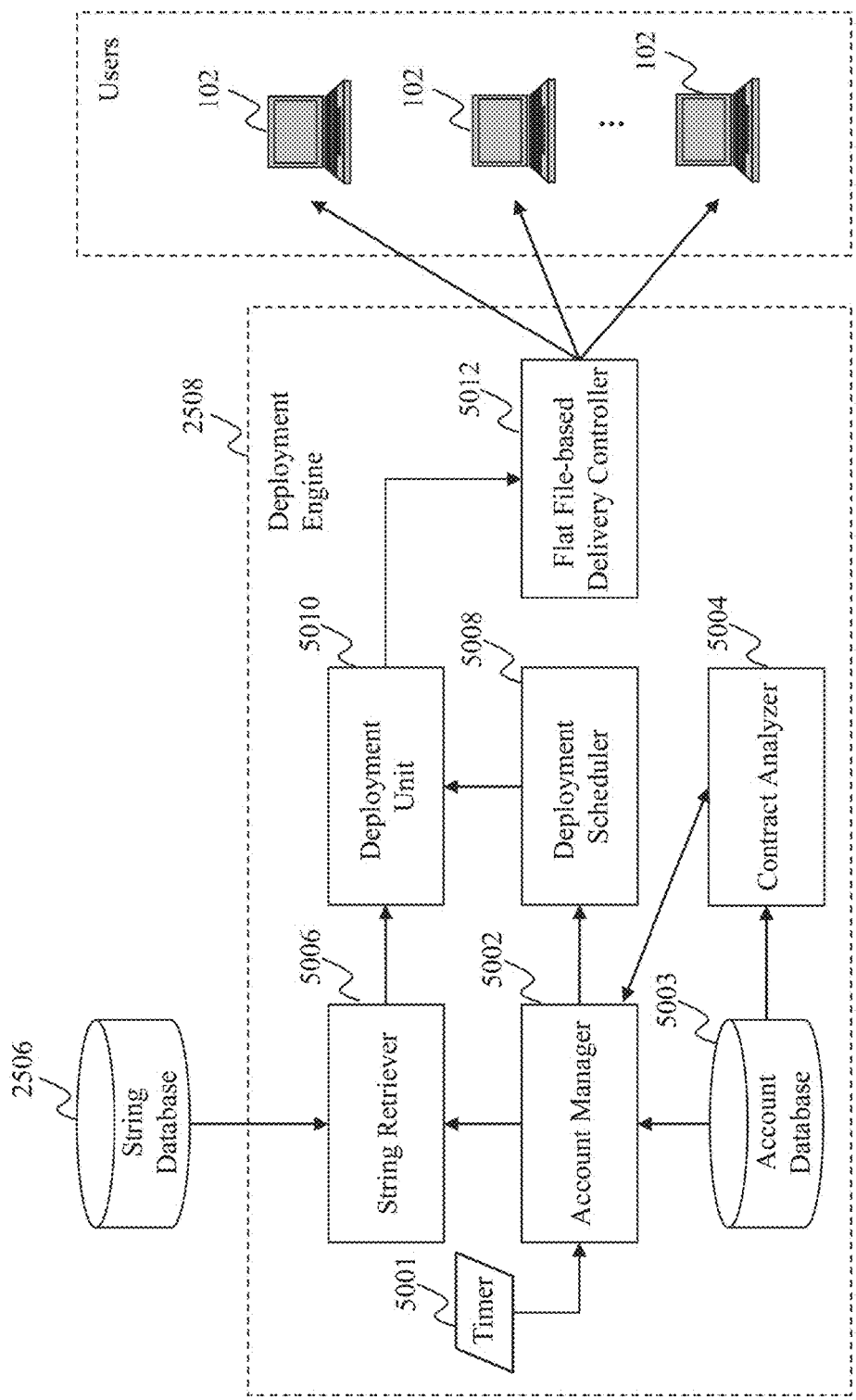
FIG. 50 illustrates yet another exemplary diagram of a deployment engine, according to another embodiment of the present teaching.

FIG. 50 illustrates yet another exemplary diagram of a deployment engine, e.g. the deployment engine 2508 in FIG. 25, according to another embodiment of the present teaching. The deployment engine 2508 in this example includes a timer 5001, an account manager 5002, an account database 5003, a contract analyzer 5004, a string retriever 5006, a deployment scheduler 5008, a deployment unit 5010, and a flat file-based delivery controller 5012.

The account manager 5002 in this example can determine whether it is time to manage an account for deploying prescription strings to a user 102 based on information from the timer 5001. If so, the account manager 5002 may retrieve account information related to the user from the account database 5003 and trigger the contract analyzer 5004 to analyze a contract associated with the account. The contract analyzer 5004 in this example analyzes contract information associated with the account to determine whether the user associated with the account has met the conditions required to obtain the prescription strings from the string database 2506. If so, the account manager 5002 sends information to the string retriever 5006.

The string retriever 5006 in this example retrieves prescription strings from the string database 2506 based on information received from the account manager 5002 and sends the prescription strings to the deployment unit 5010. The deployment scheduler 5008 in this example determines a schedule for deploying or delivering the prescription strings based on the information from the account manager 5002. For example, when delivery for multiple accounts is due within a same time period, delivery for an account associated with a higher priority based on contract information may be scheduled earlier than delivery for another account associated with a lower priority based on contract information.

The deployment unit 5010 in this example receives schedule information for each account and retrieved prescription strings for each account. The deployment unit 5010 generates a flat file for each account based on the retrieved prescription strings, where the flat file is compatible with any user 102 so that the user 102 can obtain the data in the flat file and convert to any format if the user 102 wants. The flat file-based delivery controller 5012 in this example controls delivery of the flat files to the users 102. For example, a flat file can be delivered via an email, via an electronic message, via an online platform, or by a person.

Figure 51:
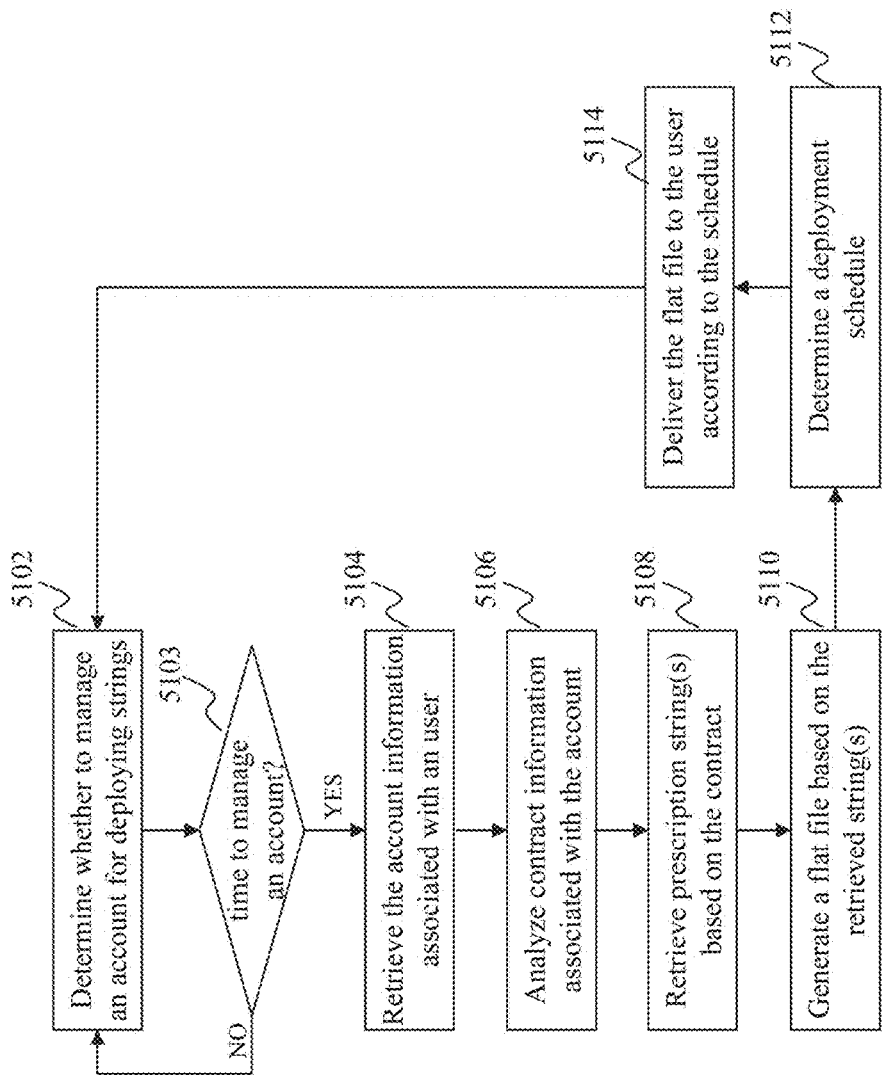
FIG. 51 is a flowchart of yet another exemplary process performed by a deployment engine, according to another embodiment of the present teaching.

FIG. 51 is a flowchart of yet another exemplary process performed by a deployment engine, e.g. the deployment engine 2508 in FIG. 50, according to another embodiment of the present teaching. Starting at 5102, it is determined whether it is time to manage an account for deploying strings to a user. At 5103, the result of determination of 5102 is checked. If it is not yet time to manage an account, the process goes back to 5102 to continue monitoring the time and account information. Otherwise, if it is time to manage an account associated with a user, the process goes to 5104, where the account information associated with the user is retrieved. At 5106, contract information associated with the account is analyzed. At 5108, one or more prescription strings are retrieved based on the contract.

At 5110, a flat file is generated based on the one or more prescription strings. At 5112, a deployment schedule is determined based on the account information and other accounts having deployment tasks in the same time period. At 5114, the flat file is delivered to the user according to the schedule, and the process goes back to 5102 to manage other accounts.

Figure 52:
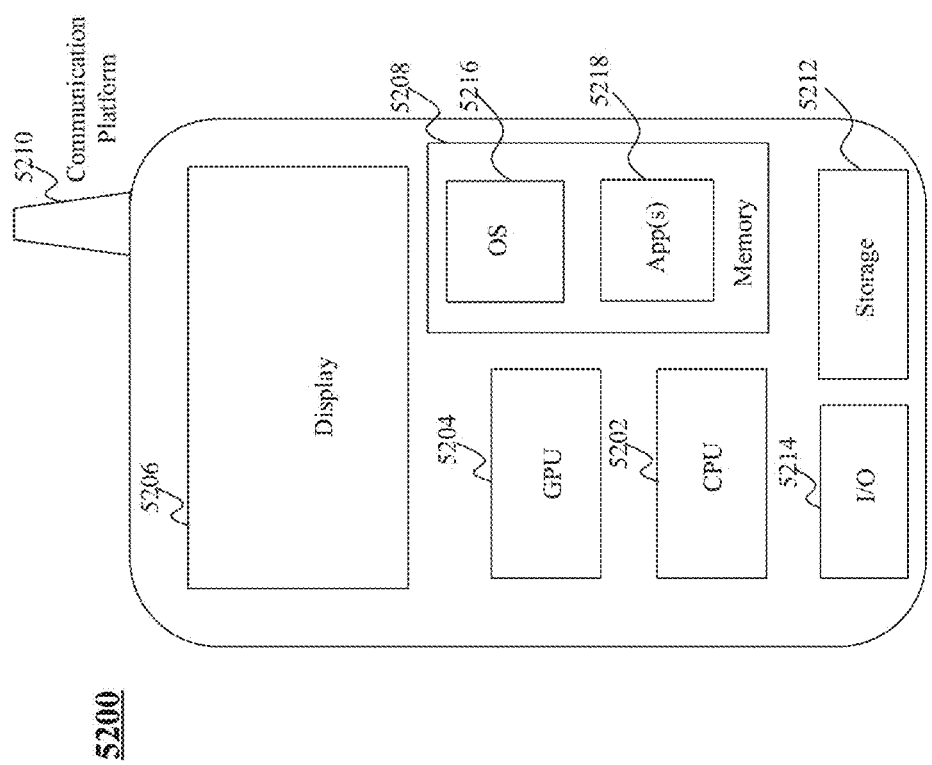
FIG. 52 depicts the architecture of a mobile device which can be used to implement a specialized system incorporating the present teaching.

FIG. 52 depicts the architecture of a mobile device which can be used to realize a specialized system implementing the present teaching. In this example, a device of the user 102 used for receiving and presenting recommended prescription string may be a mobile device 3100, including, but is not limited to, a smart phone, a tablet, a music player, a hand-held gaming console, a global positioning system (GPS) receiver, and a wearable computing device (e.g., eyeglasses, wrist watch, etc.), or in any other form. The mobile device 5200 in this example includes one or more central processing units (CPUs) 5202, one or more graphic processing units (GPUs) 5204, a display 5206, a memory 5208, a communication platform 5210, such as a wireless communication module, storage 5212, and one or more input/output (I/O) devices 5214. Any other suitable component, such as but not limited to a system bus or a controller (not shown), may also be included in the mobile device 5200. As shown in FIG. 52, a mobile operating system 5216, e.g., iOS, Android, Windows Phone, etc., and one or more applications 5218 may be loaded into the memory 5208 from the storage 5212 in order to be executed by the CPU 5202. The applications 5218 may include a web browser or any other suitable mobile apps used for electronic prescriptions. Execution of the applications 5218 may cause the mobile device 5200 to perform some processing as being described in the present teaching. For example, user inputs may be received via the I/O devices 5214 and sent to the medical suggestion searching system 106 via the communication platform 5210. Presentation of the search results to the user may be made by the GPU 5204 in conjunction with the display 5206.

To implement the present teaching, computer hardware platforms may be used as the hardware platform(s) for one or more of the elements described herein. The hardware elements, operating systems, and programming languages of such computers are conventional in nature, and it is presumed that those skilled in the art are adequately familiar therewith to adapt those technologies to implement the processing essentially as described herein. A computer with user interface elements may be used to implement a personal computer (PC) or other type of work station or terminal device, although a computer may also act as a server if appropriately programmed. It is believed that those skilled in the art are familiar with the structure, programming, and general operation of such computer equipment and as a result the drawings should be self-explanatory.

Figure 53:
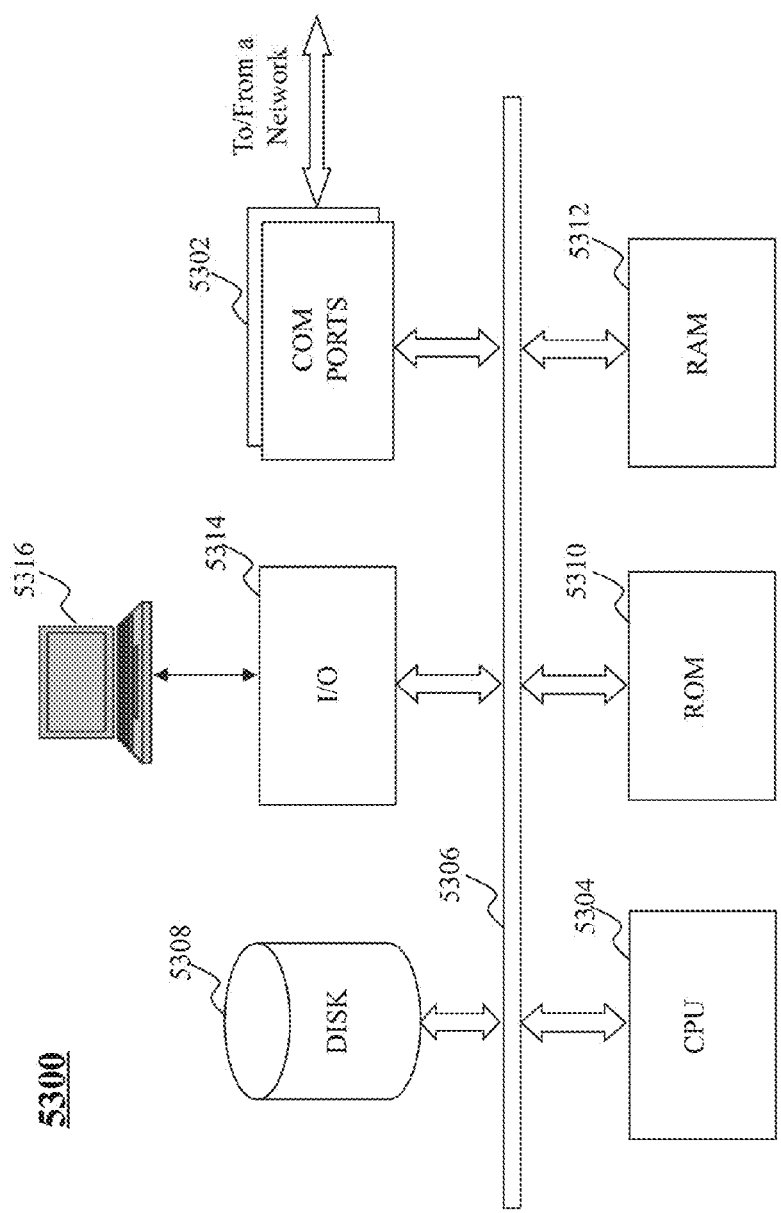
FIG. 53 depicts the architecture of a computer which can be used to implement a specialized system incorporating the present teaching.

FIG. 53 depicts the architecture of a computing device which can be used to realize a specialized system implementing the present teaching. The computer may be a general-purpose computer or a special purpose computer. This computer 5300 can be used to implement any components of the medical suggestion searching architecture as described herein. Different components of the system, e.g., as depicted in FIG. 1, can all be implemented on one or more computers such as computer 5300, via its hardware, software program, firmware, or a combination thereof. Although only one such computer is shown, for convenience, the computer functions relating to medical suggestion searching may be implemented in a distributed fashion on a number of similar platforms, to distribute the processing load.

The computer 5300, for example, includes COM ports 5302 connected to and from a network connected thereto to facilitate data communications. The computer 5300 also includes a CPU 5304, in the form of one or more processors, for executing program instructions. The exemplary computer platform includes an internal communication bus 5306, program storage and data storage of different forms, e.g., disk 5308, read only memory (ROM) 5310, or random access memory (RAM) 5312, for various data files to be processed and/or communicated by the computer, as well as possibly program instructions to be executed by the CPU 5304. The computer 5300 also includes an I/O component 5314, supporting input/output flows between the computer and other components therein such as user interface elements 5316. The computer 5300 may also receive programming and data via network communications.

Hence, aspects of the method of medical suggestion searching, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Those skilled in the art will recognize that the present teachings are amenable to a variety of modifications and/or enhancements. For example, although the implementation of various components described above may be embodied in a hardware device, it can also be implemented as a software only solution—e.g., an installation on an existing server. In addition, the medical suggestion searching system and its components as disclosed herein can be implemented as a firmware, firmware/software combination, firmware/hardware combination, or a hardware/firmware/software combination.

While the foregoing has described what are considered to constitute the present teachings and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

I claim:

1. A method, implemented on at least one computing device having at least one processor, storage, and a communication platform connected to a network for providing medical suggestion, the method comprising:
   receiving one or more dimensions, each of the one or more dimensions relating to an attribute of a patient or an attribute of a physician;
   identifying, for each of the one or more dimensions, at least one medical suggestion from a data map associating medical suggestions with dimensions, wherein each dimension-medical suggestion pair in the data map has an associated confidence score indicative of a degree of match between the medical suggestion and the dimension, the degree of match being based on statistical analysis of medical transaction data identified as relevant to the dimension-medical suggestion pair;
   calculating, for each medical suggestion, an aggregated confidence score based on an aggregation of the associated confidence scores for the medical suggestion with respect to each of the one or more dimensions;
   providing, for selection, at least some of the medical suggestions based on the aggregated confidence score of each medical suggestion;
   receiving a selection of a first medical suggestion at at least some of the medical suggestions provided; and
   boosting confidence scores for the dimension-medical suggestion pairs associated with the one or more dimensions and the first medical suggestion responsive to the selection, the boosted confidence score of a dimension-medical suggestion pair being used in calculating the aggregated confidence score for the medical suggestion responsive to a subsequent receipt of the dimension.

2. The method of claim 1, wherein medical suggestion includes at least one of:
   a medication drug;
   a physical therapy;
   a diet;
   a lab test; or
   a radiology test.

3. The method of claim 1, wherein the one or more dimensions include:
   doctor specialty;
   disease diagnosis;
   synonyms; or
   patient profile.

4. The method of claim 1, where the statistical analysis is performed by a statistic model applied to a medical transaction database.

5. The method of claim 4, wherein the statistic model considers at least one of:
   number of occurrence of the medical suggestion in data related to medical transactions in the medical transaction database;
   frequency of occurrence of the medical suggestion in data related to medical transactions in the medical transaction database; or
   recency of occurrence of the medical suggestion in data related to medical transactions in the medical transaction database.

6. The method of claim 1, wherein the aggregated confidence score for each medical suggestion is calculated by weighted summation of each confidence score of the medical suggestion with respect to each dimension.

7. The method of claim 1, wherein the medical suggestions are ranked based on the aggregated confidence score of each medical suggestion.

8. The method of claim 1, wherein the medical suggestion includes a medication drug and the method further comprises:
   identifying at least one prescription string stored previously, each of which matches the medication drugs; and
   providing the at least one prescription string as a recommendation.

9. The method of claim 1, further comprising:
   obtaining data related to medical transactions;
   mapping the obtained data into one or more dimensions;
   identifying one or more candidate medical suggestions from the mapped data in each dimension;
   in each dimension, automatically processing the mapped data based on at least one model to generate confidence scores for each of the candidate medical suggestions; and
   storing, in the data map, at least some of the candidate medical suggestions and the confidence scores thereof in each dimension.

10. A system for providing medical suggestion, comprising:
   a dimension information identifying unit configured to receive one or more dimensions, each of the one or more dimensions relating to an attribute of a patient or an attribute of a physician;
   a medical suggestion fetching unit configured to identify, for each of the one or more dimensions, at least one medical suggestion from a data map associating medical suggestions with dimensions, wherein each dimension-medical suggestion pair in the data map has an associated confidence score indicative of a degree of match between the medical suggestion and the dimension the degree of match based on statistical analysis of medical transaction data identified as relevant to the dimension-medical suggestion pair;
   a medical suggestion scoring unit configured to automatically calculate, for each medical suggestion, an aggregated confidence score based on an aggregation of the associated confidence scores for the medical suggestion with respect to each of the one or more dimensions; and
   a medical suggestion ranking unit configured to provide at least some of the identified medical suggestions based on the aggregated confidence score of each medical suggestion, to receive a selection of a first medical suggestion of the at least some of the medical suggestions provided, and to boost the confidence scores for the dimension-medical suggestion pairs associated with the one or more dimensions and the first medical suggestion, the boosted confidence score of a dimension-medical suggestion pair being used in calculating the aggregated confidence score for the medical suggestion responsive to a subsequent receipt of the dimension.

11. The system of claim 10, wherein medical suggestion includes at least one of:
   a medication drug;
   a physical therapy;
   a diet;
   a lab test; or
   a radiology test.

12. The system of claim 10, wherein the one or more dimensions include:
   doctor specialty;
   disease diagnosis;
   synonyms; or
   patient profile.

13. The system of claim 10, where the statistical analysis is performed by a statistic model applied to a medical transaction database.

14. The system of claim 13, wherein the statistic model considers at least one of:
   number of occurrence of the medical suggestion in data related to medical transactions in the medical transaction database;
   frequency of occurrence of the medical suggestion in data related to medical transactions in the medical transaction database; and
   recency of occurrence of the medical suggestion in data related to medical transactions in the medical transaction database.

15. The system of claim 10, wherein the aggregated confidence score for each medical suggestion is calculated by weighted summation of each confidence score of the medical suggestion with respect to each dimension.

16. The system of claim 10, wherein the identified medical suggestions are ranked based on the aggregated confidence score of each medical suggestion.

17. The system of claim 10, wherein the at least one medical suggestion is a medication drug and the system further comprises a prescription string recommending module configured to:
   identify at least one prescription string stored previously, each of which matches the medication drug; and
   provide the at least one prescription string as recommendation.

18. The system of claim 10, further comprising an analytic engine configured to:
obtain data related to medical transactions;
map the obtained data into one or more dimensions;
identify one or more candidate medical suggestions from the mapped data in each dimension;
in each dimension, automatically process the mapped data based on at least one model to generate confidence scores for each of the candidate medical suggestions; and
store at least some of the candidate medical suggestions and the confidence scores thereof in each dimension.

19. A non-transitory machine readable medium having information recorded thereon for providing medical suggestion, wherein the information, when read by a machine, causes the machine to perform the steps of:
receiving one or more dimensions, each of the one or more dimensions relating to an attribute of a patient or an attribute of a physician;
identifying, for each of the one or more dimensions, at least one medical suggestion from a data map associating medical suggestions with dimensions, wherein each dimension-medical suggestion pair in the data map has an associated confidence score indicative of a degree of match between the medical suggestion and the dimension, the degree of match being based on statistical analysis of medical transaction data identified as relevant to the dimension-medical suggestion pair;
calculating, for each of the at least one medical suggestion, an aggregated confidence score based on an aggregation of the associated confidence scores for the medical suggestion with respect to each of the one or more dimensions; and
providing at least some of the identified medical suggestions based on the aggregated confidence score of each medical suggestion;
receiving a selection of a first medical suggestion of the at least some of the medical suggestions provided; and
boosting confidence scores for the dimension-medical suggestion pairs associated with the one or more dimensions and the first medical suggestion responsive to the selection, the boosted confidence score of a dimension-medical suggestion pair being used in calculating the aggregated confidence score for the medical suggestion responsive to a subsequent receipt of the dimension.

20. A method, implemented on at least one computing device having at least one processor, storage, and a communication platform connected to a network for generating medical suggestion, the method comprising:
obtaining data related to medical transactions;
mapping the obtained data into one or more dimensions, each of the one or more dimensions relating to an attribute of a patient or an attribute of a physician;
identifying one or more medical suggestions from the mapped data;
pairing each of the one or more dimensions with each of the one or more medical suggestions;
for each dimension-medical suggestion pair, generating a confidence score representing a degree of match based on statistical analysis of the medical suggestion in medical transaction data;
storing at least some of the dimension-medical suggestion pairs with respective confidence scores in a data map;
providing a first medical suggestion from the data map in response to a query that specifies one or more dimensions based on the respective confidence scores;
receiving a selection of the first medical suggestion of the at least some of the medical suggestions provided; and
boosting confidence scores for the dimension-medical suggestion pairs associated with the one or more dimensions and the first medical suggestion responsive to the selection, the boosted confidence score of a dimension-medical suggestion pair being used in calculating the aggregated confidence score for the medical suggestion responsive to a subsequent receipt of the dimension.

* * * * *

UNITED STATES PATENT AND TRADEMARK OFFICE
CERTIFICATE OF CORRECTION

PATENT NO.         : 10,192,639 B2
APPLICATION NO.    : 14/613174
DATED              : January 29, 2019
INVENTOR(S)        : David Andrew Sellars Page 1 of 1

It is certified that error appears in the above-identified patent and that said Letters Patent is hereby corrected as shown below:

In the Claims

In Column 33, Claim 8, Line 44, delete "drugs; and" and insert --drug; and--, therefor.

In Column 35, Claim 19, Line 35, delete "dimensions; and" and insert --dimensions;--, therefor.

Signed and Sealed this
Thirtieth Day of April, 2019

Andrei Iancu
*Director of the United States Patent and Trademark Office*